US008143048B2

(12) United States Patent
Kragh et al.

(10) Patent No.: US 8,143,048 B2
(45) Date of Patent: *Mar. 27, 2012

(54) EXO-SPECIFIC AMYLASE POLYPEPTIDES, NUCLEIC ACIDS ENCODING THOSE POLYPEPTIDES AND USES THEREOF

(75) Inventors: Karsten Matthias Kragh, Viby J (DK); Kirsten Bojsen, Hellerup (DK); Casper Tune Berg, Vedbaek (DK); Patrick M. F. Derkx, Tikoeb (DK); Anja H. Kellett-Smith, Arhus C (DK); Charlotte Refdahl Thoudahl, Greve (DK); Carol Fioresi, Redwood City, CA (US); Wei Liu, Hayward, CA (US); Andrew Shaw, San Francisco, CA (US); Gijsbert Gerritse, Heerjansdam (NL)

(73) Assignee: Danisco A/S, Copenhagen (DK)

(*) Notice: Subject to any disclaimer, the term of this patent is extended or adjusted under 35 U.S.C. 154(b) by 0 days.

This patent is subject to a terminal disclaimer.

(21) Appl. No.: 10/886,903

(22) Filed: Jul. 7, 2004

(65) Prior Publication Data
US 2005/0136524 A1 Jun. 23, 2005

Related U.S. Application Data

(60) Provisional application No. 60/485,616, filed on Jul. 7, 2003, provisional application No. 60/485,413, filed on Jul. 7, 2003.

(51) Int. Cl.
C12N 9/28 (2006.01)
C12N 15/00 (2006.01)
C12N 9/88 (2006.01)
(52) U.S. Cl. ........ 435/202; 435/200; 435/204; 435/69.1
(58) Field of Classification Search .................. 435/201, 435/252.2
See application file for complete search history.

(56) References Cited

U.S. PATENT DOCUMENTS

| 4,683,202 | A | 7/1987 | Mullis |
| 4,946,779 | A | 8/1990 | Kameda et al. |
| 5,204,254 | A | 4/1993 | Schmid et al. |
| 5,958,749 | A | 9/1999 | Kubota et al. |
| 5,989,169 | A | 11/1999 | Svendsen et al. |
| 6,162,628 | A | 12/2000 | Cherry et al. |
| 6,242,224 | B1 | 6/2001 | Nakano et al. |
| 6,667,065 | B1 | 12/2003 | Kragh et al. |
| 7,166,453 | B2 | 1/2007 | Kragh et al. |
| 7,371,552 | B2 | 5/2008 | Kragh et al. |
| 2003/0134395 | A1 | 7/2003 | Shetty et al. |
| 2005/0059131 | A1 | 3/2005 | Bisgard-Frantzen et al. |
| 2005/0112237 | A1 | 5/2005 | Kragh et al. |
| 2005/0136524 | A1 | 6/2005 | Kragh et al. |
| 2005/0137111 | A1 | 6/2005 | Kragh et al. |
| 2006/0008888 | A1 | 1/2006 | Kragh et al. |
| 2006/0008890 | A1 | 1/2006 | Kragh et al. |
| 2006/0018997 | A1 | 1/2006 | Kragh et al. |
| 2006/0073583 | A1 | 4/2006 | Kragh et al. |
| 2007/0020727 | A1 | 1/2007 | Berg et al. |
| 2007/0020731 | A1 | 1/2007 | Kragh et al. |
| 2007/0072270 | A1 | 3/2007 | Kragh et al. |
| 2007/0141693 | A1 | 6/2007 | Berg et al. |
| 2008/0107773 | A1 | 5/2008 | Kragh et al. |
| 2008/0227173 | A1 | 9/2008 | Berg et al. |
| 2008/0274531 | A1 | 11/2008 | Berg et al. |
| 2008/0292747 | A1 | 11/2008 | Berg et al. |

FOREIGN PATENT DOCUMENTS

| EP | 0120693 | 10/1984 |
| EP | 0 298 645 | 1/1989 |
| EP | 0412607 | 2/1991 |
| EP | 0 494 233 | 7/1992 |
| JP | 6-279745 | 10/1994 |
| JP | 6-279746 | 10/1994 |
| JP | 8-205865 | 8/1996 |
| JP | 2000-245466 | 9/2000 |
| WO | WO 91/04669 | 4/1991 |
| WO | WO99/23211 | 5/1999 |
| WO | WO 99/50399 | 10/1999 |
| WO | WO 00/58447 | 10/2000 |
| WO | WO 01/04273 | 1/2001 |
| WO | WO 02/068589 | 9/2002 |
| WO | WO 2004/111217 | 12/2004 |
| WO | WO2005/003339 | 1/2005 |
| WO | WO2005/007818 | 1/2005 |
| WO | WO2005/007867 | 1/2005 |
| WO | WO2006/003461 | 1/2006 |

OTHER PUBLICATIONS

Fujita et al. J. Bactrol. 1989, 171, 1333-1339.*
UniProt database Accession No. P22963, Glucan 1,4-alpha-maltotetraohydrolase, Aug. 1, 1991.
U.S. Appl. No. 11/887,977, filed Oct. 5, 2007, Berg et al.
U.S. Appl. No. 12/339,718, filed Dec. 19, 2008, Derkx et al.
Takasaki, Y. et. al. (1982). Production of Maltohexaose by a-Amylase from *Bacillus circulans* G-6. Agricultural and Biological Chemistry, vol. 46, No. 6, p. 1539-1547.
Taniguchi, H. et. al. (1983). Purification of *Bacillus circulans* F-2 Amylase and its general properties. Agricultural and Biological Chemistry, vol. 47, No. 3, p. 511-519.
Bealin-Kelly, F. et. al. (1990). The a-amylase of the caldoactive bacterium *Bacillus caldovelox*. Biochemical Society Transactions, vol. 18, No. 2, p. 310-311.
Fogarty, W. et. al. (1991). A novel maltohexaose-forming a-amylase from *Bacillus caldovelox*: patterns and mechanisms of actions. Applied Microbiology and Biotechnology, vol. 36, p. 184-189.
Saito, N. et. al. (1973). A Thermophilic extracellular a-Amylase from *Bacillus licheniformis*. Archives of Biochemistry and Biophysics, vol. 155, p. 290-298.
Crabtree, R. et. al. (1996). Current Protocols in molecular biology. John Wiley and Sons, New York, NY, ch. 9, 13, and 16.

(Continued)

Primary Examiner — Tekchand Saidha
Assistant Examiner — Younus Meah
(74) Attorney, Agent, or Firm — Vedder Price P.C.; Thomas J. Kowalski; Smitha B. Uthaman

(57) ABSTRACT

This invention relates to amylase polypeptides, and nucleic acids encoding the polpypeptides and uses thereof. The amylases of the present invention have been engineered to have more beneficial qualities. Specifically, the amylases of the current invention show an altered exospecifity.

13 Claims, 20 Drawing Sheets

OTHER PUBLICATIONS

Okemoto, H. et. al. (1986). Isolation and cultivation of a novel microorganism producing a maltopentaose-forming enzyme. Applied Microbiology and Biotechnology, vol. 25, p. 137-142.

Zhou J. et. al. (1989). Nucleotide sequence of the maltrotetrahydrolase gene from *Pseudomonas sacchrophila*. FEBS Letters September, vol. 255, p. 37-41.

Taniguchi, H. (1991). Maltohexaose-producing amylase from *Bacillus circulans* F-2. National Food Research Institute, p. 111-124.

Sakano, Y. et. al. (1982). Purification and properties of an exo-a-amylase from *Pseudomonas stutzer*. Agricultural and Biological Chemistry, vol. 46, No. 3, p. 639-646.

Takasaki, Y. et. al. (1991). Maltotetraose-producing Amylase from *Bacillus* sp. MG-4. Agricultural and Biological Chemistry, vol. 55, No. 7, p. 1715-1720.

Database Geneseq, Apr. 7, 2005, XP002470354, retrieved from EBI accession No. GSP: ADW75735 abstract.

Database Geneseq, Apr. 7, 2005, "*P saccharophilia* variant maltotetrahydrolase protein SeqID5." XP002470355 retrieved from EBI accession No. GSP: ADW75733.

Database Geneseq, Apr. 7, 2005, "*P stutzeri* maltotetrahydrolase gene SeqID12." XP002470356 retrieved from EBI accession No. GSP: ADW73063 abstract.

Fogarty, W. et. al. (1979). Starch-degrading enzymes of microbial origin. Progress in Industrial Microbiology, vol. 15, M.J. Bell (ed), Elsevier Scientific, p. 87-150.

Kainuma, K. et. al. (1975). Purification and some properties of a novel Maltohexaose-Producing Exo-Amylase from aerobacter aerogenes. Biochimica et Biophysica Acta, p. 333-346.

Shida, O. et. al. (1992). Cloning and nucleotide sequence of the maltopentaose-forming amylase gene from *Pseudomonas* sp. KO-8940. Bioscience, Biotechnology, and Biochemistry, vol. 56, No. 1, p. 76-80.

Van der Maarel M. et. al. (2002). Properties and applications of starch-converting enzymesof the amylase family. Journal of Biotechnology, vol. 94, p. 137-155.

Ausubel et. al., (1999). Hemology Searching. Short Protocols in Molecular Biology, John Wiley and Sons, Inc., 4$^{th}$ edition, Unit 7.7, p. 7-58-7-60.

Roskams, J. et. al. (2002). Lab Ref: A handbook of recipes, reagents, and other references tools for use at the bench. Cold Spring Harbor Laboratory Press, ISBN 0-87969-630-3.

Seethala, R. et. al. (2001). Handbook of Drug Screening. Drugs and the Pharmaceutical Sciences, vol. 114, p. 1-596.

Lane, D. et. al. (1998). Using Antibodies: A Laboratory Manual: Protable Protocol No. 1. Cold Spring Harbor Laboratory Press.

Gait, M.J. (1984). Oligonucleutide Synthesis: A Practical Approach. Published in The Practical Approach Series. IRL Press. Oxford University Press, p. 1-217.

Polak, J.M. et. al. (1990). In Situ Hybridization: Principle and Practice. Ocford University Press, p. 1-247.

Chandra, A.K. et. al. (1980). Production of extracellular thermostable a-Amylase by *Bacillus licheniformis*. Journal of Fermentation Technology, vol. 58, No. 1, p. 1-10.

Srivastava, R. et. al. (1986). Culture conditions for production of thermostable amylase by *Bacillus stearothermophilus*. Applied and Environmental Microbiology, July, p. 179-184.

Planchot, V. et. al. (1995). Purification and characterization of extracellular alpha-amylase from *Aspergillus fumigatus*. Carbohydrate Research vol. 272, p. 97-109.

Ohnishi et. al. (1988). General consideration for conditions and metods of amylase assay. Handbook of Amylases and Related Enzymes. The Amylase Research Society of Japan, p. 10-14.

Larsen, K. et. al. (1998). Purification and characterization of cyclodextrin glycosyltransferase from *Paenibacillus* sp. F8. Carbohydrate Research, vol. 310, p. 211-219.

Blum, H. et. al. (1987). Improved silver staining of plant proteins, RNA and DNA in polyacrylamide gels. Electrophoresis, vol. 8, p. 93-99.

Fuwa, H. et. al. (1954). A new method for microdetermination of amylase activity by the use of amylase as the substrate. The Journal of Biochemistry, vol. 41, No. 5, p. 583-603.

Tsukamoto, A. et. al. (1988). Nucleotide sequence of the maltohexaose-producing amylase gene from an alkalophilic *Bacillus* sp. #707 and structural similarity to liquefying type a-amylase. Biochemical and Biophysical Research Communications, vol. 151, No. 1 Feburary, p. 25-31.

Lee, Y.C. et al. (1996). Carbohydrate analyses with high-performance anion-exchange chromatography. Journal of Chromatography, vol. 720, p. 137-149.

Ammeraal, R. et. al. (1991). High-performance anion-exchange chromatography with pulsed amperometric detection of linear and branched glucose oligosaccharides. Carbohydrate Research, vol. 215, p. 179-192.

Winter, G. et. al. (1991). Man-made Antibodies. Nature, vol. 349, p. 293-299.

Orlandi, R. et. al. (1989). Cloning immunoglobulin variable domains for expression by the polymerase chain reaction.. Proceedings of National Academy of Science, vol. 86, p. 3833-3837.

Takeda, S. et. al. (1985). Construction of chimaeric processed immunoglobulin genes containing mouse variable and human constant region sequences. Nature, vol. 314, p. 452-454.

Neuberger, M. et. al. (1984). Recombinant antibodies possessing novel effector functions. Nature, vol. 312, p. 604-608.

Morrison, S. et. al. (1984). Chimeric human antibodies molecules: Mouse antigen-binding domains domains with human constant region domains. Proceedings of National Academy of Sciences, vol. 81, November, p. 6851-6855.

Kennedy, J.F. et. al. (1979). Characteristics of alpha-Amylase K, a Novel amylase from a strain of *Bacillus subtilis*. Starch-Stark, vol. 31, No. 3, p. 93-99.

Cole, S.P.C. et. al. (1985). The EBV-Hybridoma technique and its application to human lung cancer. Monclonial Antibodies and Cancer Therapy, p. 77-96.

Cote, R. et. al. (1983). Generation of human monoclonal antibodies reactive with cellular antigens. Proceedings of National Academy of Sciences, vol. 80, April, p. 2026-2030.

Kozbor, D. et. al. (1983). The production of monoclonal antibodies from human lymphocytes. Immunology Today, vol. 4, No. 3, p. 72-79.

Koehler et. al. (1975). Continuous cultures of fused cells secreting antibody of predefined specificity. Nature, vol. 256, p. 495-497.

McTigue et. al. (1995). The alkaline amylase of the alkalophilic *Bacillus*. Department of Industrial Microbiology, vol. 17, p. 570-573.

Hayashi, T. et. al. (1988). Properties of new alkaline maltohexaose-forming amylases. Applied Microbiology and Biotechnology, vol. 28, p. 281-285.

Kim, T. et. al. (1995). Purification and Characterization of a Maltotetraose-forming alkaline a-amylase from an alkalophilic *Bacillus* strain, GH8901. Applied and Environmental Microbiology, August, p. 3105-3112.

Kainuma, K. et. al. (1972). Isolation and action pattern of maltohexaose producing amylase from aerobacter aerogenes. FEBS Letters, vol. 26, No. 1, p. 281-285.

Fogarty, W. et. al. (1983). Microbial Amylases. Department of Industrial Microbiology. Microbial Enzymes and Biotechnology, Applied Sciences, p. 1-92.

Min, B. et. al. (1998). Cloning of novel maltiooligosaccharide-producing amylases as antistalling agents for bread. Journal of Agricultural and Food Chemistry, vol. 46, p. 779-782.

Jakubczyk, T et. al. (1973). Scientific transactions of the academy of agriculture in Warsaw. Agriculture and Food Technology, vol. 8, p. 223-235.

Zhou, J. et. al. (1992). Properties of the enzymes expressed by the *Pseudomonas saccharophila* maltotetraohydrolase gene (mta) in *Escherichia coli*. Carbohydrate Research, vol. 223, p. 255-261.

Monma, M. et. al. (1983). Formation and Hydrolysis of Maltohexaose by an extracellular exomaltohexaohydrolase. Agricultural and Biological Chemistry, vol. 47, No. 8, p. 1769-1774.

Fogarty, W. et. al. (1994). Extracellular maltotetraose-forming amylase of *Pseudomonas* sp. Biotechnology Letters, vol. 16, No. 5, p. 473-478.

Wako, K. et. al. (1979). Purification and some properties of a maltotriose-producing amylase. Journal of the Japanese Society of Starch Science, vol. 26, No. 3, p. 175-181.

Takasaki, Y. et. al. (1985). An amylase producing maltotriose from *Bacillus subtilis*. Agricultural and Biological Chemistry, vol. 49, No. 4, p. 1091-1097.

MacGregor, E. et. al. (2001). Relationship of sequence and structure to specificity in the a-amylase family Enzymes. Biochimica et Biophysica Acta, vol. 1546, p. 1-20.

GenomeNet 1GCY, Aug. 14, 2000, High Resolution Crystal Structure of Maltotetraose-Forming Exo-Amylase.

Damien Devos, et al., Practical Limits of Function Prediction, Proteins: Structure, Function, and Genetics (2000) vol. 41, p. 98-107.

S. Sen, et al., Developments in Directed Evolution for Improving Enzyme Functions, Applied Biochemistry and Biotechnology (2007) vol. 143, p. 212-223.

James C. Whisstock, et al., Prediction of Protein Function From Protein Sequence and Structure, Quarterly Reviews of Biophysics (2003) vol. 36, No. 3, p. 307-340.

Mosimann et al., "A Critical Assessment of Comparative Molecular Modeling of Pertiary Structures of Proteins", Proteins: Structure, Function and Genetics, 1995, vol. 23, pp. 301-317.

Altschul et al., "Basic Local Alignment Search Tool", J. Mol. Biol., 1990, vol. 215, pp. 403-410.

Bernfeld, "Amylases, α and β", 1954, vol. 1, pp. 149-158.

S.L. Beaucage et al., "Deoxynucleoside Phosphoramidites—A New Class of Key Intermediates for Deoxypolynucleotide Synthesis", Tetrahedron Letters, 1981, vol. 22, No. 20, pp. 1859-1862.

Marion M. Bradford, "A Rapid and Sensitive Method for the Quantitation of Microgram Quantities of Protein Utilizing the Principle of Protein-Dye Binding", Analytical Biochemistry, 1976, vol. 72, pp. 248-254.

M.H. Caruthers et al., "New Chemical Methods for Synthesizing Polynucleotides", Nucleic Acids Research, Symposium Series No. 7, 1980, pp. 215-223.

Claus Christophersen et al., "Enzymatic Characterisation of Novamyl®, a Thermostable α-Amylase", Starch, 1997, vol. 50, No. 1, pp. 39-45.

Devereux et al., "A comprehensive set of sequence analysis programs for the VAX", Nucleic Acids Research, 1984, vol. 12, No. 1, pp. 387-395.

B. Henrissat et al., "Updating the sequence-based classification of glycosyl hydrolases", Biochem J., 1996, vol. 316, pp. 695-696.

Desmond G. Higgins et al., "CLUSTAL: a package for performing multiple sequence alignment on a microcomputer", Gene, 1988, vol. 73, No. 1, pp. 237-244.

Thomas Horn et al., "Synthesis of Oligonucleotides on Cellulose", Nucleic Acids Research, 1980, pp. 225-232.

David C. Horwell, "The 'peptoid' approach to the design of non-peptide, small molecule agonists and antagonists of neuropeptides", Trends Biotechnology, 1995, vol. 13, No. 4, pp. 132-134.

Hans W.D. Matthes, et al., "Simultaneous rapid chemical synthesis of over one hundred oligonucleotides on a microscale", The EMBO Journal, 1984, vol. 3, pp. 801-805.

Yasushi Morinaga et al., "Improvement of Oligonucleotide-Directed Site-Specific Mutagenesis Using Double-Stranded Plasmid DNA", Biotechnology, 1984, vol. 2, pp. 636-639.

Richard M. Nelson et al., "A General Method of Site-Specific Mutagenesis Using a Modification of the *Thermus aquaticus* Polymerase", Analytical Biochemistry, 1989, vol. 180, pp. 147-151.

R.K. Saiki et al., "Primer-Directed Enzymatic Amplification of DNA with a Thermostable DNA Polymerase", Science, 1988, vol. 239, pp. 487-491.

Gobinda Sarkar et al., "The "Megaprimer" Method of Site-Directed Mutagenesis", Biotechniques, 1990, vol. 8, pp. 404-407.

R.J. Simon et al., "Peptoids: a modular approach to drug discovery", PNAS, 1992, vol. 89, No. 20, pp. 9367-9371.

Hide Smith et al., "Characterization of signal-sequence-coding regions selected from the *Bacillus subtilis* chromosome", Gene, 1988, vol. 70, pp. 351-361.

T. Tatusova et al., "BLAST 2 Sequences, a new tool for comparing protein and nucleotide sequences", FEMS Microbiology Letters, 1999, vol. 174, pp. 247-250.

T. Tatusova et al., "Erratum to BLAST 2 Sequences, a new tool for comparing protein and nucleotide sequences", FEMS Microbiology Letters, 1999, vol. 177, pp. 187-188.

William Ramsay Taylor, "The Classification of Amino Acid Conservation", J. Theor. Biol., 1986, vol. 119, pp. 205-218.

\* cited by examiner

FIGURE 5

SEQ ID NO: 1

PS4 reference sequence, derived from *Pseudomonas saccharophila* maltotetrahydrolase amino acid sequence.

```
  1 DQAGKSPAGV RYHGGDEIIL QGFHWNVVRE APNDWYNILR QQASTIAADG FSAIWMPVPW
 61 RDFSSWTDGG KSGGGEGYFW HDFNKNGRYG SDAQLRQAAG ALGGAGVKVL YDVVPNHMNR
121 GYPDKEINLP AGQGFWRNDC ADPGNYPNDC DDGDRFIGGE SDLNTGHPQI YGMFRDELAN
181 LRSGYGAGGF RFDFVRGYAP ERVDSWMSDS ADSSFCVGEL WKGPSEYPSW DWRNTASWQQ
241 IIKDWSDRAK CPVFDFALKE RMQNGSVADW KHGLNGNPDP RWREVAVTFV DNHDTGYSPG
301 QNGGQHHWAL QDGLIRQAYA YILTSPGTPV VYWSHMYDWG YGDFIRQLIQ VRRTAGVRAD
361 SAISFHSGYS GLVATVSGSQ QTLVVALNSD LANPGQVASG SFSEAVNASN GQVRVWRSGS
421 GDGGGNDGGE GGLVNVNFRC DNGVTQMGDS VYAVGNVSQL GNWSPASAVR LTDTSSYPTW
481 KGSIALPDGQ NVEWKCLIRN EADATLVRQW QSGGNNQVQA AAGASTSGSF
```

FIGURE 6

SEQ ID NO: 2

PSac-D34 sequence; *Pseudomonas saccharophila* maltotetrahydrolase amino acid sequence with 10 substitutions.

```
  1 DQAGKSPAGV RYHGGDEIIL QGFHWNVVRE APYNWYNILR QQASTIAADG FSAIWMPVPW
 61 RDFSSWTDPG KSGGGEGYFW HDFNKNGRYG SDAQLRQAAG ALGGAGVKVL YDVVPNHMNR
121 GYPDKEINLP AGQRFWRNDC PDPGNYPNDC DDGDRFLGGE SDLNTGHPQI YGMFRDEFTN
181 LRSGYGAGGF RFDFVRGYAP ERVDSWMSDS ADSSFCVGEL WKAPSEYPSW DWRNTASWQQ
241 IIKDWSDRAK CPVFDFALKE RMQNGSVADW KHGLNGNPDP RWREVAVTFV DNHDTGYSPG
301 QNGGQHLWAL QDGLIRQAYA YILTSPGTPV VYWPHMYDWG YGDFIRQLIQ VRRTAGVRAD
361 SAISFHSGYS GLVATVSGSQ QTLVVALNSD LANPGQVASG SFSEAVNASN GQVRVWRSGS
421 GDGGGNDGGE GGLVNVNFRC DNGVTQMGDS VYAVGNVSQL GNWSPASAVR LTDTSSYPTW
481 KGSIALPDGQ NVEWKCLIRN EADATLVRQW QSGGNNQVQA AAGASTSGSF
```

FIGURE 7

SEQ ID NO: 3

PSac-D20 sequence; *Pseudomonas saccharophila* maltotetrahydrolase amino acid sequence with 11 substitutions.

```
  1 DQAGKSPAGV RYHGGDEIIL QGFHWNVVRE APYNWYNILR QQASTIAADG FSAIWMPVPW
 61 RDFSSWTDPG KSGGGEGYFW HDFNKNGRYG SDAQLRQAAG ALGGAGVKVL YDVVPNHMNR
121 DYPDKEINLP AGQRFWRNDC PDPGNYPNDC DDGDRFLGGE SDLNTGHPQI YGMFRDEFTN
181 LRSGYGAGGF RFDFVRGYAP ERVDSWMSDS ADSSFCVGEL WKAPSEYPSW DWRNTASWQQ
241 IIKDWSDRAK CPVFDFALKE RMQNGSVADW KHGLNGNPDP RWREVAVTFV DNHDTGYSPG
301 QNGGQHLWAL QDGLIRQAYA YILTSPGTPV VYWPHMYDWG YGDFIRQLIQ VRRTAGVRAD
361 SAISFHSGYS GLVATVSGSQ QTLVVALNSD LANPGQVASG SFSEAVNASN GQVRVWRSGS
421 GDGGGNDGGE GGLVNVNFRC DNGVTQMGDS VYAVGNVSQL GNWSPASAVR LTDTSSYPTW
```

FIGURE 8A

SEQ ID NO: 4

PSac-D14 sequence; *Pseudomonas saccharophila* maltotetrahydrolase amino acid sequence with 12 substitutions.

```
  1 DQAGKSPAGV RYHGGDEIIL QGFHWNVVRE APYNWYNILR QQASTIAADG FSAIWMPVPW
 61 RDFSSWTDPG KSGGGEGYFW HDFNKNSRYG SDAQLRQAAG ALGGAGVKVL YDVVPNHMNR
121 DYPDKEINLP AGQRFWRNDC PDPGNYPNDC DDGDRFLGGE SDLNTGHPQI YGMFRDEFTN
181 LRSGYGAGGF RFDFVRGYAP ERVDSWMSDS ADSSFCVGEL WKAPSEYPSW DWRNTASWQQ
241 IIKDWSDRAK CPVFDFALKE RMQNGSVADW KHGLNGNPDP RWREVAVTFV DNHDTGYSPG
301 QNGGQHLWAL QDGLIRQAYA YILTSPGTPV VYWPHMYDWG YGDFIRQLIQ VRRTAGVRAD
361 SAISFHSGYS GLVATVSGSQ QTLVVALNSD LANPGQVASG SFSEAVNASN GQVRVWRSGS
421 GDGGGNDGGE GGLVNVNFRC DNGVTQMGDS VYAVGNVSQL GNWSPASAVR LTDTSSYPTW
```

FIGURE 8B

SEQ ID NO: 4a

PSac-D20 sequence; *Pseudomonas saccharophila* maltotetrahydrolase amino acid sequence with 13 substitutions and deletion of the starch binding domain.

```
  1 DQAGKSPAGV RYHGGDEIIL QGFHWNVVRE APYNWYNILR QQASTIAADG FSAIWMPVPW
 61 RDFSSWTDPG RSGGGEGYFW HDFNKNGRYG SDAQLRQAAG ALGGAGVKVL YDVVPNHMNR
121 DYPDKEINLP AGQRFWRNDC PDPGNYPNDC DDGDRFLGGE SDLNTGHPQI YGMFRDEFTN
181 LRSGYGAGGF RFDFVRGYAP ERVDSWMSDS ADSSFCVGEL WKAPSEYPSW DWRNTASWQQ
241 IIKDWSDRAK CPVFDFALKE RMQNGSVADW KHGLNGNPDP RWREVAVTFV DNHDTGYSPG
301 QNGGQHLWAL QDGLIRQAYA YILTSPGTPV VYWPHMYDWG YGEFIRQLIQ VRRTAGVRAD
361 SAISFHSGYS GLVATVSGSQ QTLVVALNSD LANPGQVASG SFSEAVNASN GQVRVWRSGS
421 GDGGGNDGG
```

FIGURE 8C

SEQ ID NO: 4b

PSac–D14 sequence; *Pseudomonas saccharophila* maltotetrahydrolase amino acid sequence with 14 substitutions and deletion of the starch binding domain.

```
  1 DQAGKSPAGV RYHGGDEIIL QGFHWNVVRE APYNWYNILR QQASTIAADG FSAIWMPVPW
 61 RDFSSWTDPG RSGGGEGYFW HDFNKNSRYG SDAQLRQAAG ALGGAGVKVL YDVVPNHMNR
121 DYPDKEINLP AGQRFWRNDC PDPGNYPNDC DDGDRFLGGE SDLNTGHPQI YGMFRDEFTN
181 LRSGYGAGGF RFDFVRGYAP ERVDSWMSDS ADSSFCVGEL WKAPSEYPSW DWRNTASWQQ
241 IIKDWSDRAK CPVFDFALKE RMQNGSVADW KHGLNGNPDP RWREVAVTFV DNHDTGYSPG
301 QNGGQHLWAL QDGLIRQAYA YILTSPGTPV VYWPHMYDWG YGEFIRQLIQ VRRTAGVRAD
361 SAISFHSGYS GLVATVSGSQ QTLVVALNSD LANPGQVASG SFSEAVNASN GQVRVWRSGS
421 GDGGGNDGG
```

FIGURE 8D

SEQ ID NO: 4c

Psac-D34 sequence; *Pseudomonas saccharophila* maltotetrahydrolase amino acid sequence with 11 substitutions and deletion of the starch binding domain.

```
  1 DQAGKSPAGV RYHGGDEIIL QGFHWNVVRE APYNWYNILR QQASTIAADG FSAIWMPVPW
 61 RDFSSWTDPG KSGGGEGYFW HDFNKNGRYG SDAQLRQAAG ALGGAGVKVL YDVVPNHMNR
121 DYPDKEINLP AGQRFWRNDC PDPGNYPNDC DDGDRFLGGE SDLNTGHPQI YGMFRDEFTN
181 LRSGYGAGGF RFDFVRGYAP ERVDSWMSDS ADSSFCVGEL WKAPSEYPSW DWRNTASWQQ
241 IIKDWSDRAK CPVFDFALKE RMQNGSVADW KHGLNGNPDP RWREVAVTFV DNHDTGYSPG
301 QNGGQHLWAL QDGLIRQAYA YILTSPGTPV VYWPHMYDWG YGDFIRQLIQ VRRTAGVRAD
361 SAISFHSGYS GLVATVSGSQ QTLVVALNSD LANPGQVASG SFSEAVNASN GQVRVWRSGS
421 GDGGGNDGG
```

FIGURE 9

SEQ ID NO: 5

*Pseudomonas saccharophila* Glucan 1,4-alpha-maltotetrahydrolase precursor (EC 3.2.1.60) (G4-amylase) (Maltotetraose-forming amylase) (Exo-maltotetraohydrolase) (Maltotetraose-forming exo-amylase) SWISS-PROT accession number P22963

```
MSHILRAAVL AAVLLPFPAL ADQAGKSPAG VRYHGGDEII LQGFHWNVVR EAPNDWYNIL
RQQASTIAAD GFSAIWMPVP WRDFSSWTDG GKSGGGEGYF WHDFNKNGRY GSDAQLRQAA
GALGGAGVKV LYDVVPNHMN RGYPDKEINL PAGQGFWRND CADPGNYPND CDDGDRFIGG
ESDLNTGHPQ IYGMFRDELA NLRSGYGAGG FRFDFVRGYA PERVDSWMSD SADSSFCVGE
LWKGPSEYPS WDWRNTASWQ QIIKDWSDRA KCPVFDFALK ERMQNGSVAD WKHGLNGNPD
PRWREVAVTF VDNHDTGYSP GQNGGQHHWA LQDGLIRQAY AYILTSPGTP VVYWSHMYDW
GYGDFIRQLI QVRRTAGVRA DSAISFHSGY SGLVATVSGS QQTLVVALNS DLANPGQVAS
GSFSEAVNAS NGQVRVWRSG SGDGGGNDGG EGGLVNVNFR CDNGVTQMGD SVYAVGNVSQ
LGNWSPASAV RLTDTSSYPT WKGSIALPDG QNVEWKCLIR NEADATLVRQ WQSGGNNQVQ
AAAGASTSGS F
```

FIGURE 10A

SEQ ID NO: 6

*P. saccharophila* mta gene encoding maltotetraohydrolase (EC number = 3.2.1.60). GenBank accession number X16732.

```
gatcggcgta ggtttcgcat tcgttgccca ggcgatattt cgccggtgcg ccagcagcct
ggaagcaggc ctggtcgccg ccgccggccg tggcgccgac gcccgaacgc agatagccgt
ggaaatcgac cgccagggcc gggccgccga ccagcagggc ggcaagcagg caggcgggtt
ttaggacgaa caggggggtgc gcggtgtgct tcatgacgag gtccttgttt ttcttgttaa
tgccgaatcg atcacgcctt cgctgcgtgt cgcagggcgc agctcggtgg cgaaagcctc
ggggatggct ccgctggcgg catcctcccg accagagatt tcgctggcgc agctcgaggg
cgtaatcagg atgagtgcgg cgtaatccct ggggtggggc tacgcccggc agggcgcaga
tgattgccag gggccttcgg cctggccact acgccgcctg caactgggcg ggggaggttg
gtggtcgggg cgtgcagggg cagcctgcgg gtgccggtcg aagacccggc cggcgttcat
cctcgtccgg cggccttgcc gtaggatacc cgaacaagca caagaaccgg agtattgcga
tgagccacat cctgcgtgcc gccgtattgg cggcggtcct gctgccgttt cccgcactgg
ccgatcaggc cggcaagagc ccggccgggg tgcgctacca cggcggcgac gaaatcatcc
tccagggctt ccactggaac gtcgtccgcg aagcgcccaa cgactggtac aacatcctcc
gccaacaggc ctcgacgatc gcggccgacg gcttctcggc aatctggatg ccggtgccct
ggcgtgactt ctccagctgg accgacggcg gcaagtccgg cggcggcgaa ggctacttct
ggcacgactt caacaagaac ggccgctacg cagcgacgc ccagctgcgc caggccgccg
gcgcactcgg tggcgccggg gtgaaggtgc tctacgatgt ggtgcccaat cacatgaacc
gcggctaccc ggacaaggag atcaacctgc cggccggcca gggcttctgg cgcaacgact
gcgccgaccc gggcaactac cccaacgact gcgacgacgg tgaccgcttc atcggcggcg
agtcggacct gaacaccggc catccgcaga tttacggcat gtttcgcgac gagcttgcca
acctgcgcag cggctacggc gccggcggct tccgcttcga cttcgttcgc ggctatgcgc
ccgagcgggt cgacagctgg atgagcgaca gcgccgacag cagcttctgc gttggcgagc
tgtggaaagg ccttctgaa tatccgagct gggactggcg caacacggcg agctggcagc
agatcatcaa ggactggtcc gaccgggcca agtgcccggt gttcgacttc gctctcaagg
agcgcatgca gaacggctcg gtcgccgact ggaagcatgg cctcaatggc aaccccgacc
cgcgctggcg cgaggtggcg gtgaccttcg tcgacaacca cgacaccggc tattcgcccg
ggcagaacgg cggccagcac cactgggcgc tgcaggacgg gctgatccgc caggcctacg
cctacatcct caccagcccg ggcacgccgg tggtgtactg gtcgcacatg tacgactggg
gctacggcga cttcatccgc cagctgatcc aggtgcggcg caccgccggc gtgcgcgccg
attcggcgat cagcttccat agcggctaca gcggtctggt cgctaccgtc agcggcagcc
agcagaccct ggtggtggcg ctcaactccg atctggccaa ccccggccag gttgccagcg
gcagcttcag cgaggcggtc aacgccagca acggccaggt gcgcgtctgg cgcagcggta
gcggcgatgg cggcgggaat gacggcggcg agggtggctt ggtcaatgtg aactttcgct
gcgacaacgg cgtgacgcag atgggcgaca gcgtctacgc ggtgggcaac gtcagccagc
tcggcaactg gagcccggcc tccgcggtac ggctgaccga caccagcagc tatccgacct
ggaagggcag catcgccctg cctgacggtc agaacgtgga atggaagtgc ctgatccgca
acgaggcgga cgcgacgctg gtgcgtcagt ggcaatcggg cggcaacaac caggtccagg
ccgccgccgg cgcgagcacc agcggctcgt tctgacgaca tgcccgcccg gcctcggcta
cgcctacgcc gggcggctcc tcccgaccca gggtgggcag ggaggaggcc ggcgacgggc
cgggccgccg atgctggcac gacaaccata aaagccttcg cgctgcgctg tcgtatcagg
agctgttcat gttggcccag acccgctcga ccccttccg gcttggcttc ctggcccggc
tgtacctgct gatcgccgca ctggtggcct tgctgatgct ggtagccggc accagcctgg
ttgccatcgg ccgcctgcaa ggcaatgccg agcaaatctc gtcgaccgcg tcgcgtctgc
```

FIGURE 10B

```
tggtcagcga gagcttcttc ggtacgttgc agagcctgac gcagaacctg tccgacgccc
tggccgagga ccggcctgac cagctcgacg gctatgtcgg ccggcatcgc acgctgcagg
accaggccct cgagctgttc gcccagctgg agcgggtgac gccggcacat gccgagacca
agcaagcctg gcggcgctgt tgccggagct cgaccgccgc agcctggcgc tgatcgatgc
gcacgcgacc tgctcgcgcg tggggcgcaa cgccgtcgcc tgcgcgatct gcagctgcag
ttctcgcggc tcaagcagga cctgctgcag gcgcagttcg tgacgggcga cgagctggtc
gcctattcca tcaagcagtt catcatcccg ctcgagcagg tcgagcgctg ctgttcgatg
ccatcggcgt gtcttcgatc aaggcactcg atgaagcggg tgcgcagatc
```

FIGURE 11

SEQ ID NO:7

PS4 reference sequence, derived from *Pseudomonas stutzeri* maltotetrahydrolase amino acid sequence.

```
  1 DQAGKSPNAV RYHGGDEIIL QGFHWNVVRE APNDWYNILR QQAATIAADG FSAIWMPVPW
 61 RDFSSWSDGS KSGGGEGYFW HDFNKNGRYG SDAQLRQAAS ALGGAGVKVL YDVVPNHMNR
121 GYPDKEINLP AGQGFWRNDC ADPGNYPNDC DDGDRFIGGD ADLNTGHPQV YGMFRDEFTN
181 LRSQYGAGGF RFDFVRGYAP ERVNSWMTDS ADNSFCVGEL WKGPSEYPNW DWRNTASWQQ
241 IIKDWSDRAK CPVFDFALKE RMQNGSIADW KHGLNGNPDP RWREVAVTFV DNHDTGYSPG
301 QNGGQHHWAL QDGLIRQAYA YILTSPGTPV VYWSHMYDWG YGDFIRQLIQ VRRAAGVRAD
361 SAISFHSGYS GLVATVSGSQ QTLVVALNSD LGNPGQVASG SFSEAVNASN GQVRVWRSGT
421 GSGGGEPGAL VSVSFRCDNG ATQMGDSVYA VGNVSQLGNW SPAAALRLTD TSGYPTWKGS
481 IALPAGQNEE WKCLIRNEAN ATQVRQWQGG ANNSLTPSEG ATTVGRL
```

FIGURE 12

SEQ ID NO: 8

PStu-D34 sequence; *Pseudomonas stutzeri* maltotetrahydrolase amino acid sequence with 8 substitutions.

```
  1 DQAGKSPNAV RYHGGDEIIL QGFHWNVVRE APYNWYNILR QQAATIAADG FSAIWMPVPW
 61 RDFSSWSDPS KSGGGEGYFW HDFNKNGRYG SDAQLRQAAS ALGGAGVKVL YDVVPNHMNR
121 GYPDKEINLP AGQRFWRNDC PDPGNYPNDC DDGDRFLGGD ADLNTGHPQV YGMFRDEFTN
181 LRSQYGAGGF RFDFVRGYAP ERVNSWMTDS ADNSFCVGEL WKAPSEYPNW DWRNTASWQQ
241 IIKDWSDRAK CPVFDFALKE RMQNGSIADW KHGLNGNPDP RWREVAVTFV DNHDTGYSPG
301 QNGGQHLWAL QDGLIRQAYA YILTSPGTPV VYWPHMYDWG YGDFIRQLIQ VRRAAGVRAD
361 SAISFHSGYS GLVATVSGSQ QTLVVALNSD LGNPGQVASG SFSEAVNASN GQVRVWRSGT
421 GSGGGEPGAL VSVSFRCDNG ATQMGDSVYA VGNVSQLGNW SPAAALRLTD TSGYPTWKGS
481 IALPAGQNEE WKCLIRNEAN ATQVRQWQGG ANNSLTPSEG ATTVGRL
```

FIGURE 13

SEQ ID NO: 9

PStu-D20 sequence; *Pseudomonas stutzeri* maltotetrahydrolase amino acid sequence with 9 substitutions.

```
  1  DQAGKSPNAV  RYHGGDEIIL  QGFHWNVVRE  APYNWYNILR  QQAATIAADG  FSAIWMPVPW
 61  RDFSSWSDPS  KSGGGEGYFW  HDFNKNGRYG  SDAQLRQAAS  ALGGAGVKVL  YDVVPNHMNR
121  DYPDKEINLP  AGQRFWRNDC  PDPGNYPNDC  DDGDRFLGGD  ADLNTGHPQV  YGMFRDEFTN
181  LRSQYGAGGF  RFDFVRGYAP  ERVNSWMTDS  ADNSFCVGEL  WKAPSEYPNW  DWRNTASWQQ
241  IIKDWSDRAK  CPVFDFALKE  RMQNGSIADW  KHGLNGNPDP  RWREVAVTFV  DNHDTGYSPG
301  QNGGQHLWAL  QDGLIRQAYA  YILTSPGTPV  VYWPHMYDWG  YGDFIRQLIQ  VRRAAGVRAD
361  SAISFHSGYS  GLVATVSGSQ  QTLVVALNSD  LGNPGQVASG  SFSEAVNASN  GQVRVWRSGT
421  GSGGGEPGAL  VSVSFRCDNG  ATQMGDSVYA  VGNVSQLGNW  SPAAALRLTD  TSGYPTWKGS
481  IALPAGQNEE  WKCLIRNEAN  ATQVRQWQGG  ANNSLTPSEG  ATTVGRL
```

FIGURE 14

SEQ ID NO: 10

PStu-D14 sequence; *Pseudomonas stutzeri* maltotetrahydrolase amino acid sequence with 10 substitutions.

```
  1 DQAGKSPNAV RYHGGDEIIL QGFHWNVVRE APYNWYNILR QQAATIAADG FSAIWMPVPW
 61 RDFSSWSDPS KSGGGEGYFW HDFNKNSRYG SDAQLRQAAS ALGGAGVKVL YDVVPNHMNR
121 DYPDKEINLP AGQRFWRNDC PDPGNYPNDC DDGDRFLGGD ADLNTGHPQV YGMFRDEFTN
181 LRSQYGAGGF RFDFVRGYAP ERVNSWMTDS ADNSFCVGEL WKAPSEYPNW DWRNTASWQQ
241 IIKDWSDRAK CPVFDFALKE RMQNGSIADW KHGLNGNPDP RWREVAVTFV DNHDTGYSPG
301 QNGGQHLWAL QDGLIRQAYA YILTSPGTPV VYWPHMYDWG YGDFIRQLIQ VRRAAGVRAD
361 SAISFHSGYS GLVATVSGSQ QTLVVALNSD LGNPGQVASG SFSEAVNASN GQVRVWRSGT
421 GSGGGEPGAL VSVSFRCDNG ATQMGDSVYA VGNVSQLGNW SPAAALRLTD TSGYPTWKGS
481 IALPAGQNEE WKCLIRNEAN ATQVRQWQGG ANNSLTPSEG ATTVGRL
```

FIGURE 15

SEQ ID NO: 11

*Pseudomonas stutzeri* (*Pseudomonas perfectomarina*). Glucan 1,4-alpha-maltotetrahydrolase precursor (EC 3.2.1.60) (G4-amylase) (Maltotetraose-forming amylase) (Exo-maltotetraohydrolase)(Maltotetraose-forming exo-amylase). SWISS-PROT accession number P13507.

```
MSHILRAAVL AAMLLPLPSM ADQAGKSPNA VRYHGGDEII LQGFHWNVVR EAPNDWYNIL
RQQAATIAAD GFSAIWMPVP WRDFSSWSDG SKSGGGEGYF WHDFNKNGRY GSDAQLRQAA
SALGGAGVKV LYDVVPNHMN RGYPDKEINL PAGQGFWRND CADPGNYPND CDDGDRFIGG
DADLNTGHPQ VYGMFRDEFT NLRSQYGAGG FRFDFVRGYA PERVNSWMTD SADNSFCVGE
LWKGPSEYPN WDWRNTASWQ QIIKDWSDRA KCPVFDFALK ERMQNGSIAD WKHGLNGNPD
PRWREVAVTF VDNHDTGYSP GQNGGQHHWA LQDGLIRQAY AYILTSPGTP VVYWSHMYDW
GYGDFIRQLI QVRRAAGVRA DSAISFHSGY SGLVATVSGS QQTLVVALNS DLGNPGQVAS
GSFSEAVNAS NGQVRVWRSG TGSGGGEPGA LVSVSFRCDN GATQMGDSVY AVGNVSQLGN
WSPAAALRLT DTSGYPTWKG SIALPAGQNE EWKCLIRNEA NATQVRQWQG GANNSLTPSE
GATTVGRL
```

FIGURE 16

SEQ ID NO: 12

P.stutzeri maltotetraose-forming amylase (amyP) gene, complete cds. GenBank accession number M24516.

```
   1 gatcggcctt tacggaaagt gatagagctt ctcttccggc aaactttgtt ccccagtgac
  61 agagggttag tatcggatcg cttcctcttt gggtttggta gatcaggagc gccgagagca
 121 ggatgaaatc ctgcggccag aaggtcgcgc cgaagatgtg gaactgctgc tggccgagat
 181 ccggccggcg ttcatcctcg tccggcggcc ttgccgccag ctacccgaac aagcacaaga
 241 accggagtat tgcgatgagc cacatcctgc gagccgccgt attggcggcg atgctgttgc
 301 cgttgccgtc catggccgat caggccggca agagccccaa cgctgtgcgc taccacggcg
 361 gcgacgaaat cattctccag ggctttcact ggaacgtcgt ccgcgaagcg cccaacgact
 421 ggtacaacat cctgcgccag caggccgcga ccatcgccgc cgacggcttc tcggcgatct
 481 ggatgccggt gccctggcgc gacttctcca gctggagcga cggcagcaag tccggcggcg
 541 gtgaaggcta cttctggcac gacttcaaca agaacggccg ctatggcagt gacgcccagc
 601 tgcgtcaggc cgccagcgcg ctcggtggcg ccggcgtgaa agtgctttac gacgtggtgc
 661 ccaaccacat gaaccgtggc tatccggaca aggagatcaa cctcccggcc ggccagggct
 721 tctggcgcaa cgactgcgcc gacccgggca actaccccaa tgattgcgac gacggcgacc
 781 gcttcatcgg cggcgatgcg gacctcaaca ccggccaccc gcaggtctac ggcatgttcc
 841 gcgatgaatt caccaacctg cgcagtcagt acggtgccgg cggcttccgc ttcgactttg
 901 ttcggggcta tgcgccggag cgggtcaaca gctggatgac cgatagcgcc gacaacagct
 961 tctgcgtcgg cgaactgtgg aaaggcccct ctgagtaccc gaactgggac tggcgcaaca
1021 ccgccagctg gcagcagatc atcaaggact ggtccgaccg ggccaagtgc ccggtgttcg
1081 acttcgccct caaggaacgc atgcagaacg ctcgatcgcc gactggaagc acgcctgaac
1141 ggcaatcccg acccgcgtgg cgcgaggtgg cggtgacctt cgtcgacaac cacgacaccg
1201 gctactcgcc cgggcagaac ggtgggcagc accactgggc tctgcaggac gggctgatcc
1261 gccaggccta cgcctacatc ctcaccagcc ccggtacgcc ggtggtgtac tggtcgcaca
1321 tgtacgactg gggttacggc gacttcatcc gtcagctgat ccaggtgcgt cgcgccgccg
1381 gcgtgcgcgc cgattcggcg atcagcttcc acagcggcta cagcggtctg gtcgccaccg
1441 tcagcggcag ccagcagacc ctggtggtgg cgctcaactc cgacctgggc aatcccggcc
1501 aggtggccag cggcagcttc agcgaggcgg tcaacgccag caacggccag gtgcgcgtgt
1561 ggcgtagcgg cacgggcagc ggtggcggtg aacccggcgc tctggtcagt gtgagtttcc
1621 gctgcgacaa cggcgcgacg cagatgggcg acagcgtcta cgcggtcggc aacgtcagcc
1681 agctcggtaa ctggagcccg ccgcggcgt tgcgcctgac cgacaccagc ggctacccga
1741 cctggaaggg cagcattgcc ttgcctgccg ccagaacga ggaatggaaa tgcctgatcc
1801 gcaacgaggc caacgccacc caggtgcggc aatggcaggg cggggcaaac aacagcctga
1861 cgccgagcga gggcgccacc accgtcggcc ggctctagcc cgggcggcaa ctcggccgtc
1921 tcgcggatgt gaggcggctg gtctcggcgg cggtatcgtt gcgctggggg cggggccgcc
1981 gttcacgcgc cctgctatcg ctagttttcg gcgctccgcg catcggccag ttgccagcga
2041 atcgcctgcg cttcggcctg gtgcaggtcg tcgagcagcg ct
```

SEQUENCE LISTING

```
<160> NUMBER OF SEQ ID NOS: 42

<210> SEQ ID NO 1
<211> LENGTH: 530
<212> TYPE: PRT
<213> ORGANISM: Pseudomonas saccharophilia

<400> SEQUENCE: 1

Asp Gln Ala Gly Lys Ser Pro Ala Gly Val Arg Tyr His Gly Gly Asp
  1               5                  10                  15

Glu Ile Ile Leu Gln Gly Phe His Trp Asn Val Val Arg Glu Ala Pro
             20                  25                  30

Asn Asp Trp Tyr Asn Ile Leu Arg Gln Gln Ala Ser Thr Ile Ala Ala
         35                  40                  45

Asp Gly Phe Ser Ala Ile Trp Met Pro Val Pro Trp Arg Asp Phe Ser
     50                  55                  60

Ser Trp Thr Asp Gly Gly Lys Ser Gly Gly Gly Glu Gly Tyr Phe Trp
 65                  70                  75                  80

His Asp Phe Asn Lys Asn Gly Arg Tyr Gly Ser Asp Ala Gln Leu Arg
                 85                  90                  95

Gln Ala Ala Gly Ala Leu Gly Gly Ala Gly Val Lys Val Leu Tyr Asp
            100                 105                 110
```

```
Val Val Pro Asn His Met Asn Arg Gly Tyr Pro Asp Lys Glu Ile Asn
            115                 120                 125
Leu Pro Ala Gly Gln Gly Phe Trp Arg Asn Asp Cys Ala Asp Pro Gly
        130                 135                 140
Asn Tyr Pro Asn Asp Cys Asp Asp Gly Asp Arg Phe Ile Gly Gly Glu
145                 150                 155                 160
Ser Asp Leu Asn Thr Gly His Pro Gln Ile Tyr Gly Met Phe Arg Asp
                165                 170                 175
Glu Leu Ala Asn Leu Arg Ser Gly Tyr Gly Ala Gly Gly Phe Arg Phe
            180                 185                 190
Asp Phe Val Arg Gly Tyr Ala Pro Glu Arg Val Asp Ser Trp Met Ser
        195                 200                 205
Asp Ser Ala Asp Ser Ser Phe Cys Val Gly Leu Trp Lys Gly Pro
        210                 215                 220
Ser Glu Tyr Pro Ser Trp Asp Trp Arg Asn Thr Ala Ser Trp Gln Gln
225                 230                 235                 240
Ile Ile Lys Asp Trp Ser Asp Arg Ala Lys Cys Pro Val Phe Asp Phe
                245                 250                 255
Ala Leu Lys Glu Arg Met Gln Asn Gly Ser Val Ala Asp Trp Lys His
            260                 265                 270
Gly Leu Asn Gly Asn Pro Asp Pro Arg Trp Arg Glu Val Ala Val Thr
        275                 280                 285
Phe Val Asp Asn His Asp Thr Gly Tyr Ser Pro Gly Gln Asn Gly Gly
        290                 295                 300
Gln His His Trp Ala Leu Gln Asp Gly Leu Ile Arg Gln Ala Tyr Ala
305                 310                 315                 320
Tyr Ile Leu Thr Ser Pro Gly Thr Pro Val Val Tyr Trp Ser His Met
                325                 330                 335
Tyr Asp Trp Gly Tyr Gly Asp Phe Ile Arg Gln Leu Ile Gln Val Arg
            340                 345                 350
Arg Thr Ala Gly Val Arg Ala Asp Ser Ala Ile Ser Phe His Ser Gly
        355                 360                 365
Tyr Ser Gly Leu Val Ala Thr Val Ser Gly Ser Gln Gln Thr Leu Val
        370                 375                 380
Val Ala Leu Asn Ser Asp Leu Ala Asn Pro Gly Gln Val Ala Ser Gly
385                 390                 395                 400
Ser Phe Ser Glu Ala Val Asn Ala Ser Asn Gly Gln Val Arg Val Trp
                405                 410                 415
Arg Ser Gly Ser Gly Asp Gly Gly Gly Asn Asp Gly Gly Glu Gly Gly
            420                 425                 430
Leu Val Asn Val Asn Phe Arg Cys Asp Asn Gly Val Thr Gln Met Gly
        435                 440                 445
Asp Ser Val Tyr Ala Val Gly Asn Val Ser Gln Leu Gly Asn Trp Ser
450                 455                 460
Pro Ala Ser Ala Val Arg Leu Thr Asp Thr Ser Ser Tyr Pro Thr Trp
465                 470                 475                 480
Lys Gly Ser Ile Ala Leu Pro Asp Gly Gln Asn Val Glu Trp Lys Cys
                485                 490                 495
Leu Ile Arg Asn Glu Ala Asp Ala Thr Leu Val Arg Gln Trp Gln Ser
            500                 505                 510
Gly Gly Asn Asn Gln Val Gln Ala Ala Gly Ala Ser Thr Ser Gly
        515                 520                 525
Ser Phe
```

<210> SEQ ID NO 2
<211> LENGTH: 530
<212> TYPE: PRT
<213> ORGANISM: Artificial Sequence
<220> FEATURE:
<223> OTHER INFORMATION: Pseudomonas saccharophilia PS4 variant

<400> SEQUENCE: 2

```
Asp Gln Ala Gly Lys Ser Pro Ala Gly Val Arg Tyr His Gly Gly Asp
  1               5                  10                  15

Glu Ile Ile Leu Gln Gly Phe His Trp Asn Val Val Arg Glu Ala Pro
             20                  25                  30

Tyr Asn Trp Tyr Asn Ile Leu Arg Gln Gln Ala Ser Thr Ile Ala Ala
         35                  40                  45

Asp Gly Phe Ser Ala Ile Trp Met Pro Val Pro Trp Arg Asp Phe Ser
     50                  55                  60

Ser Trp Thr Asp Pro Gly Lys Ser Gly Gly Gly Glu Gly Tyr Phe Trp
 65                  70                  75                  80

His Asp Phe Asn Lys Asn Gly Arg Tyr Gly Ser Asp Ala Gln Leu Arg
                 85                  90                  95

Gln Ala Ala Gly Ala Leu Gly Gly Ala Gly Val Lys Val Leu Tyr Asp
            100                 105                 110

Val Val Pro Asn His Met Asn Arg Gly Tyr Pro Asp Lys Glu Ile Asn
        115                 120                 125

Leu Pro Ala Gly Gln Arg Phe Trp Arg Asn Asp Cys Pro Asp Pro Gly
    130                 135                 140

Asn Tyr Pro Asn Asp Cys Asp Asp Gly Asp Arg Phe Leu Gly Gly Glu
145                 150                 155                 160

Ser Asp Leu Asn Thr Gly His Pro Gln Ile Tyr Gly Met Phe Arg Asp
                165                 170                 175

Glu Phe Thr Asn Leu Arg Ser Gly Tyr Gly Ala Gly Gly Phe Arg Phe
            180                 185                 190

Asp Phe Val Arg Gly Tyr Ala Pro Glu Arg Val Asp Ser Trp Met Ser
        195                 200                 205

Asp Ser Ala Asp Ser Ser Phe Cys Val Gly Glu Leu Trp Lys Ala Pro
    210                 215                 220

Ser Glu Tyr Pro Ser Trp Asp Trp Arg Asn Thr Ala Ser Trp Gln Gln
225                 230                 235                 240

Ile Ile Lys Asp Trp Ser Asp Arg Ala Lys Cys Pro Val Phe Asp Phe
                245                 250                 255

Ala Leu Lys Glu Arg Met Gln Asn Gly Ser Val Ala Asp Trp Lys His
            260                 265                 270

Gly Leu Asn Gly Asn Pro Asp Pro Arg Trp Arg Glu Val Ala Val Thr
        275                 280                 285

Phe Val Asp Asn His Asp Thr Gly Tyr Ser Pro Gly Gln Asn Gly Gly
    290                 295                 300

Gln His Leu Trp Ala Leu Gln Asp Gly Leu Ile Arg Gln Ala Tyr Ala
305                 310                 315                 320

Tyr Ile Leu Thr Ser Pro Gly Thr Pro Val Val Tyr Trp Pro His Met
                325                 330                 335

Tyr Asp Trp Gly Tyr Gly Asp Phe Ile Arg Gln Leu Ile Gln Val Arg
            340                 345                 350

Arg Thr Ala Gly Val Arg Ala Asp Ser Ala Ile Ser Phe His Ser Gly
        355                 360                 365
```

```
Tyr Ser Gly Leu Val Ala Thr Val Gly Ser Gln Gln Thr Leu Val
    370                 375                 380

Val Ala Leu Asn Ser Asp Leu Ala Asn Pro Gly Gln Val Ala Ser Gly
385                 390                 395                 400

Ser Phe Ser Glu Ala Val Asn Ala Ser Asn Gly Gln Val Arg Val Trp
                405                 410                 415

Arg Ser Gly Ser Gly Asp Gly Gly Asn Asp Gly Gly Glu Gly Gly
                420                 425                 430

Leu Val Asn Val Asn Phe Arg Cys Asp Asn Gly Val Thr Gln Met Gly
                435                 440                 445

Asp Ser Val Tyr Ala Val Gly Asn Val Ser Gln Leu Gly Asn Trp Ser
                450                 455                 460

Pro Ala Ser Ala Val Arg Leu Thr Asp Thr Ser Ser Tyr Pro Thr Trp
465                 470                 475                 480

Lys Gly Ser Ile Ala Leu Pro Asp Gly Gln Asn Val Glu Trp Lys Cys
                485                 490                 495

Leu Ile Arg Asn Glu Ala Asp Ala Thr Leu Val Arg Gln Trp Gln Ser
                500                 505                 510

Gly Gly Asn Asn Gln Val Gln Ala Ala Gly Ala Ser Thr Ser Gly
                515                 520                 525

Ser Phe
    530

<210> SEQ ID NO 3
<211> LENGTH: 480
<212> TYPE: PRT
<213> ORGANISM: Artificial Sequence
<220> FEATURE:
<223> OTHER INFORMATION: Pseudomonas saccharophilia PS4 variant

<400> SEQUENCE: 3

Asp Gln Ala Gly Lys Ser Pro Ala Gly Val Arg Tyr His Gly Gly Asp
1               5                   10                  15

Glu Ile Ile Leu Gln Gly Phe His Trp Asn Val Val Arg Glu Ala Pro
                20                  25                  30

Tyr Asn Trp Tyr Asn Ile Leu Arg Gln Gln Ala Ser Thr Ile Ala Ala
            35                  40                  45

Asp Gly Phe Ser Ala Ile Trp Met Pro Val Pro Trp Arg Asp Phe Ser
    50                  55                  60

Ser Trp Thr Asp Pro Gly Lys Ser Gly Gly Gly Glu Gly Tyr Phe Trp
65                  70                  75                  80

His Asp Phe Asn Lys Asn Gly Arg Tyr Gly Ser Asp Ala Gln Leu Arg
                85                  90                  95

Gln Ala Ala Gly Ala Leu Gly Gly Ala Gly Val Lys Val Leu Tyr Asp
                100                 105                 110

Val Val Pro Asn His Met Asn Arg Asp Tyr Pro Asp Lys Glu Ile Asn
                115                 120                 125

Leu Pro Ala Gly Gln Arg Phe Trp Arg Asn Asp Cys Pro Asp Pro Gly
            130                 135                 140

Asn Tyr Pro Asn Asp Cys Asp Asp Gly Asp Arg Phe Leu Gly Gly Glu
145                 150                 155                 160

Ser Asp Leu Asn Thr Gly His Pro Gln Ile Tyr Gly Met Phe Arg Asp
                165                 170                 175

Glu Phe Thr Asn Leu Arg Ser Gly Tyr Gly Ala Gly Gly Phe Arg Phe
                180                 185                 190
```

```
Asp Phe Val Arg Gly Tyr Ala Pro Glu Arg Val Asp Ser Trp Met Ser
    195                 200                 205

Asp Ser Ala Asp Ser Ser Phe Cys Val Gly Glu Leu Trp Lys Ala Pro
210                 215                 220

Ser Glu Tyr Pro Ser Trp Asp Trp Arg Asn Thr Ala Ser Trp Gln Gln
225                 230                 235                 240

Ile Ile Lys Asp Trp Ser Asp Arg Ala Lys Cys Pro Val Phe Asp Phe
                245                 250                 255

Ala Leu Lys Glu Arg Met Gln Asn Gly Ser Val Ala Asp Trp Lys His
                260                 265                 270

Gly Leu Asn Gly Asn Pro Asp Pro Arg Trp Arg Glu Val Ala Val Thr
            275                 280                 285

Phe Val Asp Asn His Asp Thr Gly Tyr Ser Pro Gly Gln Asn Gly Gly
    290                 295                 300

Gln His Leu Trp Ala Leu Gln Asp Gly Leu Ile Arg Gln Ala Tyr Ala
305                 310                 315                 320

Tyr Ile Leu Thr Ser Pro Gly Thr Pro Val Val Tyr Trp Pro His Met
                325                 330                 335

Tyr Asp Trp Gly Tyr Gly Asp Phe Ile Arg Gln Leu Ile Gln Val Arg
                340                 345                 350

Arg Thr Ala Gly Val Arg Ala Asp Ser Ala Ile Ser Phe His Ser Gly
            355                 360                 365

Tyr Ser Gly Leu Val Ala Thr Val Ser Gly Ser Gln Gln Thr Leu Val
    370                 375                 380

Val Ala Leu Asn Ser Asp Leu Ala Asn Pro Gly Gln Val Ala Ser Gly
385                 390                 395                 400

Ser Phe Ser Glu Ala Val Asn Ala Ser Asn Gly Gln Val Arg Val Trp
                405                 410                 415

Arg Ser Gly Ser Gly Asp Gly Gly Asn Asp Gly Glu Gly Gly
                420                 425                 430

Leu Val Asn Val Asn Phe Arg Cys Asp Asn Gly Val Thr Gln Met Gly
            435                 440                 445

Asp Ser Val Tyr Ala Val Gly Asn Val Ser Gln Leu Gly Asn Trp Ser
    450                 455                 460

Pro Ala Ser Ala Val Arg Leu Thr Asp Thr Ser Ser Tyr Pro Thr Trp
465                 470                 475                 480
```

<210> SEQ ID NO 4
<211> LENGTH: 480
<212> TYPE: PRT
<213> ORGANISM: Artificial Sequence
<220> FEATURE:
<223> OTHER INFORMATION: Pseudomonas saccharophilia maltotetrahydrolase
      variant

<400> SEQUENCE: 4

```
Asp Gln Ala Gly Lys Ser Pro Ala Gly Val Arg Tyr His Gly Gly Asp
  1               5                  10                  15

Glu Ile Ile Leu Gln Gly Phe His Trp Asn Val Val Arg Glu Ala Pro
                 20                  25                  30

Tyr Asn Trp Tyr Asn Ile Leu Arg Gln Gln Ala Ser Thr Ile Ala Ala
             35                  40                  45

Asp Gly Phe Ser Ala Ile Trp Met Pro Val Pro Trp Arg Asp Phe Ser
         50                  55                  60

Ser Trp Thr Asp Pro Gly Lys Ser Gly Gly Gly Glu Gly Tyr Phe Trp
65                  70                  75                  80
```

-continued

His Asp Phe Asn Lys Asn Ser Arg Tyr Gly Ser Asp Ala Gln Leu Arg
                85                  90                  95

Gln Ala Ala Gly Ala Leu Gly Gly Ala Gly Val Lys Val Leu Tyr Asp
            100                 105                 110

Val Val Pro Asn His Met Asn Arg Asp Tyr Pro Asp Lys Glu Ile Asn
        115                 120                 125

Leu Pro Ala Gly Gln Arg Phe Trp Arg Asn Asp Cys Pro Asp Pro Gly
    130                 135                 140

Asn Tyr Pro Asn Asp Cys Asp Asp Gly Asp Arg Phe Leu Gly Gly Glu
145                 150                 155                 160

Ser Asp Leu Asn Thr Gly His Pro Gln Ile Tyr Gly Met Phe Arg Asp
                165                 170                 175

Glu Phe Thr Asn Leu Arg Ser Gly Tyr Gly Ala Gly Gly Phe Arg Phe
            180                 185                 190

Asp Phe Val Arg Gly Tyr Ala Pro Glu Arg Val Asp Ser Trp Met Ser
        195                 200                 205

Asp Ser Ala Asp Ser Ser Phe Cys Val Gly Glu Leu Trp Lys Ala Pro
    210                 215                 220

Ser Glu Tyr Pro Ser Trp Asp Trp Arg Asn Thr Ala Ser Trp Gln Gln
225                 230                 235                 240

Ile Ile Lys Asp Trp Ser Asp Arg Ala Lys Cys Pro Val Phe Asp Phe
                245                 250                 255

Ala Leu Lys Glu Arg Met Gln Asn Gly Ser Val Ala Asp Trp Lys His
            260                 265                 270

Gly Leu Asn Gly Asn Pro Asp Pro Arg Trp Arg Glu Val Ala Val Thr
        275                 280                 285

Phe Val Asp Asn His Asp Thr Gly Tyr Ser Pro Gly Gln Asn Gly Gly
    290                 295                 300

Gln His Leu Trp Ala Leu Gln Asp Gly Leu Ile Arg Gln Ala Tyr Ala
305                 310                 315                 320

Tyr Ile Leu Thr Ser Pro Gly Thr Pro Val Val Tyr Trp Pro His Met
                325                 330                 335

Tyr Asp Trp Gly Tyr Gly Asp Phe Ile Arg Gln Leu Ile Gln Val Arg
            340                 345                 350

Arg Thr Ala Gly Val Arg Ala Asp Ser Ala Ile Ser Phe His Ser Gly
        355                 360                 365

Tyr Ser Gly Leu Val Ala Thr Val Ser Gly Ser Gln Gln Thr Leu Val
    370                 375                 380

Val Ala Leu Asn Ser Asp Leu Ala Asn Pro Gly Gln Val Ala Ser Gly
385                 390                 395                 400

Ser Phe Ser Glu Ala Val Asn Ala Ser Asn Gly Gln Val Arg Val Trp
                405                 410                 415

Arg Ser Gly Ser Gly Asp Gly Gly Asn Asp Gly Glu Gly Gly
            420                 425                 430

Leu Val Asn Val Asn Phe Arg Cys Asp Asn Gly Val Thr Gln Met Gly
        435                 440                 445

Asp Ser Val Tyr Ala Val Gly Asn Val Ser Gln Leu Gly Asn Trp Ser
    450                 455                 460

Pro Ala Ser Ala Val Arg Leu Thr Asp Thr Ser Ser Tyr Pro Thr Trp
465                 470                 475                 480

<210> SEQ ID NO 5
<211> LENGTH: 551
<212> TYPE: PRT
<213> ORGANISM: Pseudomonas saccharophilia

<400> SEQUENCE: 5

```
Met Ser His Ile Leu Arg Ala Ala Val Leu Ala Ala Val Leu Leu Pro
  1               5                  10                  15

Phe Pro Ala Leu Ala Asp Gln Ala Gly Lys Ser Pro Ala Gly Val Arg
             20                  25                  30

Tyr His Gly Gly Asp Glu Ile Ile Leu Gln Gly Phe His Trp Asn Val
         35                  40                  45

Val Arg Glu Ala Pro Asn Asp Trp Tyr Asn Ile Leu Arg Gln Gln Ala
 50                  55                  60

Ser Thr Ile Ala Ala Asp Gly Phe Ser Ala Ile Trp Met Pro Val Pro
 65                  70                  75                  80

Trp Arg Asp Phe Ser Ser Trp Thr Asp Gly Gly Lys Ser Gly Gly Gly
                 85                  90                  95

Glu Gly Tyr Phe Trp His Asp Phe Asn Lys Asn Gly Arg Tyr Gly Ser
            100                 105                 110

Asp Ala Gln Leu Arg Gln Ala Ala Gly Ala Leu Gly Gly Ala Gly Val
            115                 120                 125

Lys Val Leu Tyr Asp Val Val Pro Asn His Met Asn Arg Gly Tyr Pro
130                 135                 140

Asp Lys Glu Ile Asn Leu Pro Ala Gly Gln Gly Phe Trp Arg Asn Asp
145                 150                 155                 160

Cys Ala Asp Pro Gly Asn Tyr Pro Asn Asp Cys Asp Gly Asp Arg
                165                 170                 175

Phe Ile Gly Gly Glu Ser Asp Leu Asn Thr Gly His Pro Gln Ile Tyr
                180                 185                 190

Gly Met Phe Arg Asp Glu Leu Ala Asn Leu Arg Ser Gly Tyr Gly Ala
            195                 200                 205

Gly Gly Phe Arg Phe Asp Phe Val Arg Gly Tyr Ala Pro Glu Arg Val
            210                 215                 220

Asp Ser Trp Met Ser Asp Ser Ala Asp Ser Ser Phe Cys Val Gly Glu
225                 230                 235                 240

Leu Trp Lys Gly Pro Ser Glu Tyr Pro Ser Trp Asp Trp Arg Asn Thr
                245                 250                 255

Ala Ser Trp Gln Gln Ile Ile Lys Asp Trp Ser Asp Arg Ala Lys Cys
            260                 265                 270

Pro Val Phe Asp Phe Ala Leu Lys Glu Arg Met Gln Asn Gly Ser Val
            275                 280                 285

Ala Asp Trp Lys His Gly Leu Asn Gly Asn Pro Asp Pro Arg Trp Arg
290                 295                 300

Glu Val Ala Val Thr Phe Val Asp Asn His Asp Thr Gly Tyr Ser Pro
305                 310                 315                 320

Gly Gln Asn Gly Gly Gln His His Trp Ala Leu Gln Asp Gly Leu Ile
                325                 330                 335

Arg Gln Ala Tyr Ala Tyr Ile Leu Thr Ser Pro Gly Thr Pro Val Val
            340                 345                 350

Tyr Trp Ser His Met Tyr Asp Trp Gly Tyr Gly Asp Phe Ile Arg Gln
            355                 360                 365

Leu Ile Gln Val Arg Arg Thr Ala Gly Val Arg Ala Asp Ser Ala Ile
370                 375                 380

Ser Phe His Ser Gly Tyr Ser Gly Leu Val Ala Thr Val Ser Gly Ser
385                 390                 395                 400

Gln Gln Thr Leu Val Val Ala Leu Asn Ser Asp Leu Ala Asn Pro Gly
                405                 410                 415
```

```
Gln Val Ala Ser Gly Ser Phe Ser Glu Ala Val Asn Ala Ser Asn Gly
            420                 425                 430

Gln Val Arg Val Trp Arg Ser Gly Ser Gly Asp Gly Gly Asn Asp
            435                 440                 445

Gly Gly Glu Gly Gly Leu Val Asn Val Asn Phe Arg Cys Asp Asn Gly
450                 455                 460

Val Thr Gln Met Gly Asp Ser Val Tyr Ala Val Gly Asn Val Ser Gln
465                 470                 475                 480

Leu Gly Asn Trp Ser Pro Ala Ser Ala Val Arg Leu Thr Asp Thr Ser
                485                 490                 495

Ser Tyr Pro Thr Trp Lys Gly Ser Ile Ala Leu Pro Asp Gly Gln Asn
            500                 505                 510

Val Glu Trp Lys Cys Leu Ile Arg Asn Glu Ala Asp Ala Thr Leu Val
            515                 520                 525

Arg Gln Trp Gln Ser Gly Gly Asn Asn Gln Val Gln Ala Ala Ala Gly
            530                 535                 540

Ala Ser Thr Ser Gly Ser Phe
545                 550

<210> SEQ ID NO 6
<211> LENGTH: 3050
<212> TYPE: DNA
<213> ORGANISM: Pseudomonas saccharophilia

<400> SEQUENCE: 6
gatcggcgta ggtttcgcat tcgttgccca ggcgatattt cgccggtgcg ccagcagcct      60
ggaagcaggc ctggtcgccg ccgccggccg tggcgccgac gcccgaacgc agatagccgt     120
ggaaatcgac cgccagggcc gggccgccga ccagcagggc ggcaagcagg caggcgggtt     180
ttaggacgaa caggggggtgc gcggtgtgct tcatgacgag gtccttgttt ttcttgttaa    240
tgccgaatcg atcacgcctt cgctgcgtgt cgcagggcgc agctcggtgg cgaaagcctc     300
ggggatggct ccgctggcgg catcctcccg accagagatt cgctggcgc agctcgaggg      360
cgtaatcagg atgagtgcgg cgtaatccct ggggtggggc tacgcccggc agggcgcaga    420
tgattgccag gggccttcgg cctggccact acgccgcctg caactgggcg ggggaggttg     480
gtggtcgggg cgtgcagggg cagcctgcgg gtgccggtcg aagacccggc cggcgttcat     540
cctcgtccgg cggccttgcc gtaggatacc cgaacaagca caagaaccgg agtattgcga     600
tgagccacat cctgcgtgcc gccgtattgg cggcggtcct gctgccgttt ccgcactgg      660
ccgatcaggc cggcaagagc ccggccgggg tgcgctacca cggcggcgac gaaatcatcc     720
tccagggctt ccactggaac gtcgtccgcg aagcgcccaa cgactggtac aacatcctcc     780
gccaacaggc ctcgacgatc gcggccgacg gcttctcggc aatctggatg ccggtgccct     840
ggcgtgactt ctccagctgg accgacggcg gcaagtccgg cggcggcgaa ggctacttct     900
ggcacgactt caacaagaac ggccgctacg gcagcgacgc ccagctgcgc caggccgccg     960
gcgcactcgg tggcgccggg gtgaaggtgc tctacgatgt ggtgcccaat cacatgaacc    1020
gcggctaccc ggacaaggag atcaacctgc cggccggcca gggcttctgg cgcaacgact    1080
gcgccgaccc gggcaactac cccaacgact gcgacgacgg tgaccgcttc atcgcggcg     1140
agtcggacct gaacaccggc catccgcaga tttacggcat gttcgcgac gagcttgcca     1200
acctgcgcag cggctacggc gccggcggct tccgcttcga cttcgttcgc ggctatgcgc    1260
ccgagcgggt cgacagctgg atgagcgaca gcgccgacag cagcttctgc gttggcgagc    1320
```

-continued

```
tgtggaaagg cccttctgaa tatccgagct gggactggcg caacacggcg agctggcagc    1380
agatcatcaa ggactggtcc gaccgggcca agtgcccgt gttcgacttc gctctcaagg     1440
agcgcatgca gaacggctcg gtcgccgact ggaagcatgg cctcaatggc aaccccgacc    1500
cgcgctggcg cgaggtggcg gtgaccttcg tcgacaacca cgacaccggc tattcgcccg    1560
ggcagaacgg cggccagcac cactgggcgc tgcaggacgg gctgatccgc caggcctacg    1620
cctacatcct caccagcccg ggcacgccgg tggtgtactg gtcgcacatg tacgactggg    1680
gctacggcga cttcatccgc cagctgatcc aggtgcggcg caccgccggc gtgcgcgccg    1740
attcggcgat cagcttccat agcggctaca gcggtctggt cgctaccgtc agcggcagcc    1800
agcagaccct ggtggtggcg ctcaactccg atctggccaa ccccggccag gttgccagcg    1860
gcagcttcag cgaggcggtc aacgccagca acggccaggt gcgcgtctgg cgcagcggta    1920
gcggcgatgg cggcgggaat gacggcggcg agggtggctt ggtcaatgtg aactttcgct    1980
gcgacaacgg cgtgacgcag atgggcgaca gcgtctacgc ggtgggcaac gtcagccagc    2040
tcggcaactg gagcccggcc tccgcggtac ggctgaccga caccagcagc tatccgacct    2100
ggaagggcag catcgccctg cctgacggtc agaacgtgga atggaagtgc ctgatccgca    2160
acgaggcgga cgcgacgctg gtgcgtcagt ggcaatcggg cggcaacaac caggtccagg    2220
ccgccgccgg cgcgagcacc agcggctcgt tctgacgaca tgcccgcccg gcctcggcta    2280
cgcctacgcc gggcggctcc tcccgaccca gggtgggcag ggaggaggcc ggcgacgggc    2340
cgggccgccg atgctggcac gacaaccata aaagccttcg cgctgcgctg tcgtatcagg    2400
agctgttcat gttggcccag acccgctcga cccctttccg gcttggcttc ctggcccggc    2460
tgtacctgct gatcgccgca ctggtggcct tgctgatgct ggtagccggc accagcctgg    2520
ttgccatcgg ccgcctgcaa ggcaatgccg agcaaatctc gtcgaccgcg tcgcgtctgc    2580
tggtcagcga gagcttcttc ggtacgttgc agagcctgac gcagaacctg tccgacgccc    2640
tggccgagga ccggcctgac cagctcgacg gctatgtcgg ccggcatcgc acgctgcagg    2700
accaggccct cgagctgttc gcccagctgg agcgggtgac gccggcacat gccgagacca    2760
agcaagcctg gcgcgcgctgt tgccggagct cgaccgccgc agcctggcgc tgatcgatgc    2820
gcacgcgacc tgctcgcgcg tggggcgcaa cgccgtcgcc tgcgcgatct gcagctgcag    2880
ttctcgcggc tcaagcagga cctgctgcag gcgcagttcg tgacgggcga cgagctggtc    2940
gcctattcca tcaagcagtt catcatcccg ctcgagcagg tcgagcgctg ctgttcgatg    3000
ccatcggcgt gtcttcgatc aaggcactcg atgaagcggg tgcgcagatc              3050
```

<210> SEQ ID NO 7
<211> LENGTH: 527
<212> TYPE: PRT
<213> ORGANISM: Pseudomonas stutzeri

<400> SEQUENCE: 7

```
Asp Gln Ala Gly Lys Ser Pro Asn Ala Val Arg Tyr His Gly Gly Asp
1               5                   10                  15

Glu Ile Ile Leu Gln Gly Phe His Trp Asn Val Val Arg Glu Ala Pro
            20                  25                  30

Asn Asp Trp Tyr Asn Ile Leu Arg Gln Gln Ala Thr Ile Ala Ala
        35                  40                  45

Asp Gly Phe Ser Ala Ile Trp Met Pro Val Pro Trp Arg Asp Phe Ser
    50                  55                  60

Ser Trp Ser Asp Gly Ser Lys Ser Gly Gly Gly Glu Gly Tyr Phe Trp
65                  70                  75                  80
```

```
His Asp Phe Asn Lys Asn Gly Arg Tyr Gly Ser Asp Ala Gln Leu Arg
                 85                  90                  95

Gln Ala Ala Ser Ala Leu Gly Gly Ala Gly Val Lys Val Leu Tyr Asp
            100                 105                 110

Val Val Pro Asn His Met Asn Arg Gly Tyr Pro Asp Lys Glu Ile Asn
        115                 120                 125

Leu Pro Ala Gly Gln Gly Phe Trp Arg Asn Asp Cys Ala Asp Pro Gly
    130                 135                 140

Asn Tyr Pro Asn Asp Cys Asp Gly Asp Arg Phe Ile Gly Gly Asp
145                 150                 155                 160

Ala Asp Leu Asn Thr Gly His Pro Gln Val Tyr Gly Met Phe Arg Asp
                165                 170                 175

Glu Phe Thr Asn Leu Arg Ser Gln Tyr Gly Ala Gly Gly Phe Arg Phe
            180                 185                 190

Asp Phe Val Arg Gly Tyr Ala Pro Glu Arg Val Asn Ser Trp Met Thr
        195                 200                 205

Asp Ser Ala Asp Asn Ser Phe Cys Val Gly Glu Leu Trp Lys Gly Pro
    210                 215                 220

Ser Glu Tyr Pro Asn Trp Asp Trp Arg Asn Thr Ala Ser Trp Gln Gln
225                 230                 235                 240

Ile Ile Lys Asp Trp Ser Asp Arg Ala Lys Cys Pro Val Phe Asp Phe
                245                 250                 255

Ala Leu Lys Glu Arg Met Gln Asn Gly Ser Ile Ala Asp Trp Lys His
            260                 265                 270

Gly Leu Asn Gly Asn Pro Asp Pro Arg Trp Arg Glu Val Ala Val Thr
        275                 280                 285

Phe Val Asp Asn His Asp Thr Gly Tyr Ser Pro Gly Gln Asn Gly Gly
    290                 295                 300

Gln His His Trp Ala Leu Gln Asp Gly Leu Ile Arg Gln Ala Tyr Ala
305                 310                 315                 320

Tyr Ile Leu Thr Ser Pro Gly Thr Pro Val Val Tyr Trp Ser His Met
                325                 330                 335

Tyr Asp Trp Gly Tyr Gly Asp Phe Ile Arg Gln Leu Ile Gln Val Arg
            340                 345                 350

Arg Ala Ala Gly Val Arg Ala Asp Ser Ala Ile Ser Phe His Ser Gly
        355                 360                 365

Tyr Ser Gly Leu Val Ala Thr Val Ser Gly Ser Gln Gln Thr Leu Val
    370                 375                 380

Val Ala Leu Asn Ser Asp Leu Gly Asn Pro Gly Gln Val Ala Ser Gly
385                 390                 395                 400

Ser Phe Ser Glu Ala Val Asn Ala Ser Asn Gly Gln Val Arg Val Trp
                405                 410                 415

Arg Ser Gly Thr Gly Ser Gly Gly Glu Pro Gly Ala Leu Val Ser
            420                 425                 430

Val Ser Phe Arg Cys Asp Asn Gly Ala Thr Gln Met Gly Asp Ser Val
        435                 440                 445

Tyr Ala Val Gly Asn Val Ser Gln Leu Gly Asn Trp Ser Pro Ala Ala
    450                 455                 460

Ala Leu Arg Leu Thr Asp Thr Ser Gly Tyr Pro Thr Trp Lys Gly Ser
465                 470                 475                 480

Ile Ala Leu Pro Ala Gly Gln Asn Glu Glu Trp Lys Cys Leu Ile Arg
                485                 490                 495

Asn Glu Ala Asn Ala Thr Gln Val Arg Gln Trp Gln Gly Gly Ala Asn
```

```
                500             505             510
Asn Ser Leu Thr Pro Ser Glu Gly Ala Thr Thr Val Gly Arg Leu
        515             520             525

<210> SEQ ID NO 8
<211> LENGTH: 527
<212> TYPE: PRT
<213> ORGANISM: Artificial Sequence
<220> FEATURE:
<223> OTHER INFORMATION: Pseudomonas stutzeri maltotetrahydrolase
      variant

<400> SEQUENCE: 8

Asp Gln Ala Gly Lys Ser Pro Asn Ala Val Arg Tyr His Gly Gly Asp
1               5                   10                  15

Glu Ile Ile Leu Gln Gly Phe His Trp Asn Val Val Arg Glu Ala Pro
            20                  25                  30

Tyr Asn Trp Tyr Asn Ile Leu Arg Gln Gln Ala Ala Thr Ile Ala Ala
        35                  40                  45

Asp Gly Phe Ser Ala Ile Trp Met Pro Val Pro Trp Arg Asp Phe Ser
    50                  55                  60

Ser Trp Ser Asp Pro Ser Lys Ser Gly Gly Glu Gly Tyr Phe Trp
65                  70                  75                  80

His Asp Phe Asn Lys Asn Gly Arg Tyr Gly Ser Asp Ala Gln Leu Arg
                85                  90                  95

Gln Ala Ala Ser Ala Leu Gly Gly Ala Gly Val Lys Val Leu Tyr Asp
            100                 105                 110

Val Val Pro Asn His Met Asn Arg Gly Tyr Pro Asp Lys Glu Ile Asn
        115                 120                 125

Leu Pro Ala Gly Gln Arg Phe Trp Arg Asn Asp Cys Pro Asp Pro Gly
    130                 135                 140

Asn Tyr Pro Asn Asp Cys Asp Asp Gly Asp Arg Phe Leu Gly Gly Asp
145                 150                 155                 160

Ala Asp Leu Asn Thr Gly His Pro Gln Val Tyr Gly Met Phe Arg Asp
                165                 170                 175

Glu Phe Thr Asn Leu Arg Ser Gln Tyr Gly Ala Gly Gly Phe Arg Phe
            180                 185                 190

Asp Phe Val Arg Gly Tyr Ala Pro Glu Arg Val Asn Ser Trp Met Thr
        195                 200                 205

Asp Ser Ala Asp Asn Ser Phe Cys Val Gly Glu Leu Trp Lys Ala Pro
    210                 215                 220

Ser Glu Tyr Pro Asn Trp Asp Trp Arg Asn Thr Ala Ser Trp Gln Gln
225                 230                 235                 240

Ile Ile Lys Asp Trp Ser Asp Arg Ala Lys Cys Pro Val Phe Asp Phe
                245                 250                 255

Ala Leu Lys Glu Arg Met Gln Asn Gly Ser Ile Ala Asp Trp Lys His
            260                 265                 270

Gly Leu Asn Gly Asn Pro Asp Pro Arg Trp Arg Glu Val Ala Val Thr
        275                 280                 285

Phe Val Asp Asn His Asp Thr Gly Tyr Ser Pro Gly Gln Asn Gly Gly
    290                 295                 300

Gln His Leu Trp Ala Leu Gln Asp Gly Leu Ile Arg Gln Ala Tyr Ala
305                 310                 315                 320

Tyr Ile Leu Thr Ser Pro Gly Thr Pro Val Val Tyr Trp Pro His Met
                325                 330                 335

Tyr Asp Trp Gly Tyr Gly Asp Phe Ile Arg Gln Leu Ile Gln Val Arg
```

```
                       340                 345                 350
Arg Ala Ala Gly Val Arg Ala Asp Ser Ala Ile Ser Phe His Ser Gly
                355                 360                 365
Tyr Ser Gly Leu Val Ala Thr Val Ser Gly Ser Gln Gln Thr Leu Val
            370                 375                 380
Val Ala Leu Asn Ser Asp Leu Gly Asn Pro Gly Gln Val Ala Ser Gly
385                 390                 395                 400
Ser Phe Ser Glu Ala Val Asn Ala Ser Asn Gly Gln Val Arg Val Trp
                405                 410                 415
Arg Ser Gly Thr Gly Ser Gly Gly Glu Pro Gly Ala Leu Val Ser
            420                 425                 430
Val Ser Phe Arg Cys Asp Asn Gly Ala Thr Gln Met Gly Asp Ser Val
        435                 440                 445
Tyr Ala Val Gly Asn Val Ser Gln Leu Gly Asn Trp Ser Pro Ala Ala
        450                 455                 460
Ala Leu Arg Leu Thr Asp Thr Ser Gly Tyr Pro Thr Trp Lys Gly Ser
465                 470                 475                 480
Ile Ala Leu Pro Ala Gly Gln Asn Glu Glu Trp Lys Cys Leu Ile Arg
                485                 490                 495
Asn Glu Ala Asn Ala Thr Gln Val Arg Gln Trp Gln Gly Gly Ala Asn
            500                 505                 510
Asn Ser Leu Thr Pro Ser Glu Gly Ala Thr Thr Val Gly Arg Leu
        515                 520                 525

<210> SEQ ID NO 9
<211> LENGTH: 527
<212> TYPE: PRT
<213> ORGANISM: Artificial Sequence
<220> FEATURE:
<223> OTHER INFORMATION: Pseudomonas stutzeri maltotetrahydrolase
      variant

<400> SEQUENCE: 9

Asp Gln Ala Gly Lys Ser Pro Asn Ala Val Arg Tyr His Gly Gly Asp
 1               5                  10                  15
Glu Ile Ile Leu Gln Gly Phe His Trp Asn Val Val Arg Glu Ala Pro
                20                  25                  30
Tyr Asn Trp Tyr Asn Ile Leu Arg Gln Gln Ala Ala Thr Ile Ala Ala
            35                  40                  45
Asp Gly Phe Ser Ala Ile Trp Met Pro Val Pro Trp Arg Asp Phe Ser
        50                  55                  60
Ser Trp Ser Asp Pro Ser Lys Ser Gly Gly Gly Glu Gly Tyr Phe Trp
65                  70                  75                  80
His Asp Phe Asn Lys Asn Gly Arg Tyr Gly Ser Asp Ala Gln Leu Arg
                85                  90                  95
Gln Ala Ala Ser Ala Leu Gly Gly Ala Gly Val Lys Val Leu Tyr Asp
            100                 105                 110
Val Val Pro Asn His Met Asn Arg Asp Tyr Pro Asp Lys Glu Ile Asn
        115                 120                 125
Leu Pro Ala Gly Gln Arg Phe Trp Arg Asn Asp Cys Pro Asp Pro Gly
    130                 135                 140
Asn Tyr Pro Asn Asp Cys Asp Asp Gly Asp Arg Phe Leu Gly Gly Asp
145                 150                 155                 160
Ala Asp Leu Asn Thr Gly His Pro Gln Val Tyr Gly Met Phe Arg Asp
                165                 170                 175
Glu Phe Thr Asn Leu Arg Ser Gln Tyr Gly Ala Gly Gly Phe Arg Phe
```

```
                    180                 185                 190
Asp Phe Val Arg Gly Tyr Ala Pro Glu Arg Val Asn Ser Trp Met Thr
            195                 200                 205
Asp Ser Ala Asp Asn Ser Phe Cys Val Gly Glu Leu Trp Lys Ala Pro
        210                 215                 220
Ser Glu Tyr Pro Asn Trp Asp Trp Arg Asn Thr Ala Ser Trp Gln Gln
225                 230                 235                 240
Ile Ile Lys Asp Trp Ser Asp Arg Ala Lys Cys Pro Val Phe Asp Phe
                245                 250                 255
Ala Leu Lys Glu Arg Met Gln Asn Gly Ser Ile Ala Asp Trp Lys His
            260                 265                 270
Gly Leu Asn Gly Asn Pro Asp Pro Arg Trp Arg Glu Val Ala Val Thr
        275                 280                 285
Phe Val Asp Asn His Asp Thr Gly Tyr Ser Pro Gly Gln Asn Gly Gly
        290                 295                 300
Gln His Leu Trp Ala Leu Gln Asp Gly Leu Ile Arg Gln Ala Tyr Ala
305                 310                 315                 320
Tyr Ile Leu Thr Ser Pro Gly Thr Pro Val Val Tyr Trp Pro His Met
                325                 330                 335
Tyr Asp Trp Gly Tyr Gly Asp Phe Ile Arg Gln Leu Ile Gln Val Arg
            340                 345                 350
Arg Ala Ala Gly Val Arg Ala Asp Ser Ala Ile Ser Phe His Ser Gly
        355                 360                 365
Tyr Ser Gly Leu Val Ala Thr Val Ser Gly Ser Gln Gln Thr Leu Val
        370                 375                 380
Val Ala Leu Asn Ser Asp Leu Gly Asn Pro Gly Gln Val Ala Ser Gly
385                 390                 395                 400
Ser Phe Ser Glu Ala Val Asn Ala Ser Asn Gly Gln Val Arg Val Trp
                405                 410                 415
Arg Ser Gly Thr Gly Ser Gly Gly Glu Pro Gly Ala Leu Val Ser
            420                 425                 430
Val Ser Phe Arg Cys Asp Asn Gly Ala Thr Gln Met Gly Asp Ser Val
        435                 440                 445
Tyr Ala Val Gly Asn Val Ser Gln Leu Gly Asn Trp Ser Pro Ala Ala
        450                 455                 460
Ala Leu Arg Leu Thr Asp Thr Ser Gly Tyr Pro Thr Trp Lys Gly Ser
465                 470                 475                 480
Ile Ala Leu Pro Ala Gly Gln Asn Glu Glu Trp Lys Cys Leu Ile Arg
                485                 490                 495
Asn Glu Ala Asn Ala Thr Gln Val Arg Gln Trp Gln Gly Gly Ala Asn
            500                 505                 510
Asn Ser Leu Thr Pro Ser Glu Gly Ala Thr Thr Val Gly Arg Leu
        515                 520                 525

<210> SEQ ID NO 10
<211> LENGTH: 527
<212> TYPE: PRT
<213> ORGANISM: Artificial Sequence
<220> FEATURE:
<223> OTHER INFORMATION: Pseudomonas stutzeri maltotetrahydrolase
      variant

<400> SEQUENCE: 10

Asp Gln Ala Gly Lys Ser Pro Asn Ala Val Arg Tyr His Gly Gly Asp
1               5                   10                  15

Glu Ile Ile Leu Gln Gly Phe His Trp Asn Val Val Arg Glu Ala Pro
```

-continued

```
                20                  25                  30
Tyr Asn Trp Tyr Asn Ile Leu Arg Gln Gln Ala Ala Thr Ile Ala Ala
            35                  40                  45
Asp Gly Phe Ser Ala Ile Trp Met Pro Val Pro Trp Arg Asp Phe Ser
 50                  55                  60
Ser Trp Ser Asp Pro Ser Lys Ser Gly Gly Glu Gly Tyr Phe Trp
 65                  70                  75                  80
His Asp Phe Asn Lys Asn Ser Arg Tyr Gly Ser Asp Ala Gln Leu Arg
                85                  90                  95
Gln Ala Ala Ser Ala Leu Gly Gly Ala Gly Val Lys Val Leu Tyr Asp
               100                 105                 110
Val Val Pro Asn His Met Asn Arg Asp Tyr Pro Asp Lys Glu Ile Asn
           115                 120                 125
Leu Pro Ala Gly Gln Arg Phe Trp Arg Asn Asp Cys Pro Asp Pro Gly
           130                 135                 140
Asn Tyr Pro Asn Asp Cys Asp Asp Gly Asp Arg Phe Leu Gly Gly Asp
145                 150                 155                 160
Ala Asp Leu Asn Thr Gly His Pro Gln Val Tyr Gly Met Phe Arg Asp
               165                 170                 175
Glu Phe Thr Asn Leu Arg Ser Gln Tyr Gly Ala Gly Gly Phe Arg Phe
           180                 185                 190
Asp Phe Val Arg Gly Tyr Ala Pro Glu Arg Val Asn Ser Trp Met Thr
           195                 200                 205
Asp Ser Ala Asp Asn Ser Phe Cys Val Gly Glu Leu Trp Lys Ala Pro
           210                 215                 220
Ser Glu Tyr Pro Asn Trp Asp Trp Arg Asn Thr Ala Ser Trp Gln Gln
225                 230                 235                 240
Ile Ile Lys Asp Trp Ser Asp Arg Ala Lys Cys Pro Val Phe Asp Phe
               245                 250                 255
Ala Leu Lys Glu Arg Met Gln Asn Gly Ser Ile Ala Asp Trp Lys His
           260                 265                 270
Gly Leu Asn Gly Asn Pro Asp Pro Arg Trp Arg Glu Val Ala Val Thr
           275                 280                 285
Phe Val Asp Asn His Asp Thr Gly Tyr Ser Pro Gly Gln Asn Gly Gly
           290                 295                 300
Gln His Leu Trp Ala Leu Gln Asp Gly Leu Ile Arg Gln Ala Tyr Ala
305                 310                 315                 320
Tyr Ile Leu Thr Ser Pro Gly Thr Pro Val Val Tyr Trp Pro His Met
               325                 330                 335
Tyr Asp Trp Gly Tyr Gly Asp Phe Ile Arg Gln Leu Ile Gln Val Arg
               340                 345                 350
Arg Ala Ala Gly Val Arg Ala Asp Ser Ala Ile Ser Phe His Ser Gly
           355                 360                 365
Tyr Ser Gly Leu Val Ala Thr Val Ser Gly Ser Gln Gln Thr Leu Val
           370                 375                 380
Val Ala Leu Asn Ser Asp Leu Gly Asn Pro Gly Gln Val Ala Ser Gly
385                 390                 395                 400
Ser Phe Ser Glu Ala Val Asn Ala Ser Asn Gly Gln Val Arg Val Trp
               405                 410                 415
Arg Ser Gly Thr Gly Ser Gly Gly Glu Pro Gly Ala Leu Val Ser
           420                 425                 430
Val Ser Phe Arg Cys Asp Asn Gly Ala Thr Gln Met Gly Asp Ser Val
           435                 440                 445
```

```
Tyr Ala Val Gly Asn Val Ser Gln Leu Gly Asn Trp Ser Pro Ala Ala
            450                 455                 460

Ala Leu Arg Leu Thr Asp Thr Ser Gly Tyr Pro Thr Trp Lys Gly Ser
465                 470                 475                 480

Ile Ala Leu Pro Ala Gly Gln Asn Glu Glu Trp Lys Cys Leu Ile Arg
                    485                 490                 495

Asn Glu Ala Asn Ala Thr Gln Val Arg Gln Trp Gln Gly Gly Ala Asn
                500                 505                 510

Asn Ser Leu Thr Pro Ser Glu Gly Ala Thr Thr Val Gly Arg Leu
            515                 520                 525

<210> SEQ ID NO 11
<211> LENGTH: 548
<212> TYPE: PRT
<213> ORGANISM: Pseudomonas stutzeri

<400> SEQUENCE: 11

Met Ser His Ile Leu Arg Ala Ala Val Leu Ala Ala Met Leu Leu Pro
  1               5                  10                  15

Leu Pro Ser Met Ala Asp Gln Ala Gly Lys Ser Pro Asn Ala Val Arg
                 20                  25                  30

Tyr His Gly Gly Asp Glu Ile Ile Leu Gln Gly Phe His Trp Asn Val
             35                  40                  45

Val Arg Glu Ala Pro Asn Asp Trp Tyr Asn Ile Leu Arg Gln Gln Ala
 50                  55                  60

Ala Thr Ile Ala Ala Asp Gly Phe Ser Ala Ile Trp Met Pro Val Pro
 65                  70                  75                  80

Trp Arg Asp Phe Ser Ser Trp Ser Asp Gly Ser Lys Ser Gly Gly Gly
                 85                  90                  95

Glu Gly Tyr Phe Trp His Asp Phe Asn Lys Asn Gly Arg Tyr Gly Ser
            100                 105                 110

Asp Ala Gln Leu Arg Gln Ala Ala Ser Ala Leu Gly Gly Ala Gly Val
            115                 120                 125

Lys Val Leu Tyr Asp Val Val Pro Asn His Met Asn Arg Gly Tyr Pro
130                 135                 140

Asp Lys Glu Ile Asn Leu Pro Ala Gly Gln Gly Phe Trp Arg Asn Asp
145                 150                 155                 160

Cys Ala Asp Pro Gly Asn Tyr Pro Asn Asp Cys Asp Ser Gly Asp Arg
                165                 170                 175

Phe Ile Gly Gly Asp Ala Asp Leu Asn Thr Gly His Pro Gln Val Tyr
            180                 185                 190

Gly Met Phe Arg Asp Glu Phe Thr Asn Leu Arg Ser Gln Tyr Gly Ala
            195                 200                 205

Gly Gly Phe Arg Phe Asp Phe Val Arg Gly Tyr Ala Pro Glu Arg Val
            210                 215                 220

Asn Ser Trp Met Thr Asp Ser Ala Asp Asn Ser Phe Cys Val Gly Glu
225                 230                 235                 240

Leu Trp Lys Gly Pro Ser Glu Tyr Pro Asn Trp Asp Trp Arg Asn Thr
                245                 250                 255

Ala Ser Trp Gln Gln Ile Ile Lys Asp Trp Ser Asp Arg Ala Lys Cys
            260                 265                 270

Pro Val Phe Asp Phe Ala Leu Lys Glu Arg Met Gln Asn Gly Ser Ile
            275                 280                 285

Ala Asp Trp Lys His Gly Leu Asn Gly Asn Pro Asp Pro Arg Trp Arg
            290                 295                 300
```

| | | | | | | | | | | | | |
|---|---|---|---|---|---|---|---|---|---|---|---|---|
| Glu | Val | Ala | Val | Thr | Phe | Val | Asp | Asn | His | Asp | Thr | Gly | Tyr | Ser | Pro |
| 305 | | | | 310 | | | | | 315 | | | | | 320 | |

| Gly | Gln | Asn | Gly | Gly | Gln | His | His | Trp | Ala | Leu | Gln | Asp | Gly | Leu | Ile |
|---|---|---|---|---|---|---|---|---|---|---|---|---|---|---|---|
| | | | | 325 | | | | | 330 | | | | | 335 | |

| Arg | Gln | Ala | Tyr | Ala | Tyr | Ile | Leu | Thr | Ser | Pro | Gly | Thr | Pro | Val | Val |
|---|---|---|---|---|---|---|---|---|---|---|---|---|---|---|---|
| | | | 340 | | | | | 345 | | | | | 350 | | |

| Tyr | Trp | Ser | His | Met | Tyr | Asp | Trp | Gly | Tyr | Gly | Asp | Phe | Ile | Arg | Gln |
|---|---|---|---|---|---|---|---|---|---|---|---|---|---|---|---|
| | | | 355 | | | | | 360 | | | | | 365 | | |

| Leu | Ile | Gln | Val | Arg | Arg | Ala | Ala | Gly | Val | Arg | Ala | Asp | Ser | Ala | Ile |
|---|---|---|---|---|---|---|---|---|---|---|---|---|---|---|---|
| | 370 | | | | | 375 | | | | | 380 | | | | |

| Ser | Phe | His | Ser | Gly | Tyr | Ser | Gly | Leu | Val | Ala | Thr | Val | Ser | Gly | Ser |
|---|---|---|---|---|---|---|---|---|---|---|---|---|---|---|---|
| 385 | | | | | 390 | | | | | 395 | | | | | 400 |

| Gln | Gln | Thr | Leu | Val | Ala | Leu | Asn | Ser | Asp | Leu | Gly | Asn | Pro | Gly |
|---|---|---|---|---|---|---|---|---|---|---|---|---|---|---|
| | | | | 405 | | | | | 410 | | | | | 415 |

| Gln | Val | Ala | Ser | Gly | Ser | Phe | Ser | Glu | Ala | Val | Asn | Ala | Ser | Asn | Gly |
|---|---|---|---|---|---|---|---|---|---|---|---|---|---|---|---|
| | | | 420 | | | | | 425 | | | | | 430 | | |

| Gln | Val | Arg | Val | Trp | Arg | Ser | Gly | Thr | Gly | Ser | Gly | Gly | Glu | Pro |
|---|---|---|---|---|---|---|---|---|---|---|---|---|---|---|
| | | 435 | | | | | 440 | | | | | 445 | | |

| Gly | Ala | Leu | Val | Ser | Val | Ser | Phe | Arg | Cys | Asn | Gly | Ala | Thr | Gln |
|---|---|---|---|---|---|---|---|---|---|---|---|---|---|---|
| 450 | | | | | 455 | | | | | 460 | | | | |

| Met | Gly | Asp | Ser | Val | Tyr | Ala | Val | Gly | Asn | Val | Ser | Gln | Leu | Gly | Asn |
|---|---|---|---|---|---|---|---|---|---|---|---|---|---|---|---|
| 465 | | | | | 470 | | | | | 475 | | | | | 480 |

| Trp | Ser | Pro | Ala | Ala | Ala | Leu | Arg | Leu | Thr | Asp | Thr | Ser | Gly | Tyr | Pro |
|---|---|---|---|---|---|---|---|---|---|---|---|---|---|---|---|
| | | | | 485 | | | | | 490 | | | | | 495 | |

| Thr | Trp | Lys | Gly | Ser | Ile | Ala | Leu | Pro | Ala | Gly | Gln | Asn | Glu | Glu | Trp |
|---|---|---|---|---|---|---|---|---|---|---|---|---|---|---|---|
| | | | 500 | | | | | 505 | | | | | 510 | | |

| Lys | Cys | Leu | Ile | Arg | Asn | Glu | Ala | Asn | Ala | Thr | Gln | Val | Arg | Gln | Trp |
|---|---|---|---|---|---|---|---|---|---|---|---|---|---|---|---|
| | | 515 | | | | | 520 | | | | | 525 | | | |

| Gln | Gly | Gly | Ala | Asn | Asn | Ser | Leu | Thr | Pro | Ser | Glu | Gly | Ala | Thr | Thr |
|---|---|---|---|---|---|---|---|---|---|---|---|---|---|---|---|
| | 530 | | | | | 535 | | | | | 540 | | | | |

| Val | Gly | Arg | Leu |
|---|---|---|---|
| 545 | | | |

<210> SEQ ID NO 12
<211> LENGTH: 2082
<212> TYPE: DNA
<213> ORGANISM: Pseudomonas stutzeri

<400> SEQUENCE: 12

| | |
|---|---|
| gatcggcctt tacggaaagt gatagagctt ctcttccggc aaactttgtt ccccagtgac | 60 |
| agagggttag tatcggatcg cttcctcttt gggtttggta gatcaggagc gccgagagca | 120 |
| ggatgaaatc ctgcggccag aaggtcgcgc cgaagatgtg gaactgctgc tggccgagat | 180 |
| ccggccggcg ttcatcctcg tccggcggcc ttgccgccag ctacccgaac aagcacaaga | 240 |
| accggagtat tgcgatgagc cacatcctgc gagccgccgt attggcggcg atgctgttgc | 300 |
| cgttgccgtc catggccgat caggccggca agagccccaa cgctgtgcgc taccacggcg | 360 |
| gcgacgaaat cattctccag ggctttcact ggaacgtcgt ccgcgaagcg cccaacgact | 420 |
| ggtacaacat cctgcgccag caggccgcga ccatcgccgc cgacggcttc tcggcgatct | 480 |
| ggatgccggt gccctggcgc gacttctcca gctggagcga cggcagcaag tccgcgggcg | 540 |
| gtgaaggcta cttctggcac gacttcaaca agaacggccg ctatggcagt gacgcccagc | 600 |
| tgcgtcaggc cgccagcgcg ctcggtggcc cggcgtgaa agtgctttac gacgtggtgc | 660 |
| ccaaccacat gaaccgtggc tatccggaca aggagatcaa cctcccggcc ggccagggct | 720 |

```
tctggcgcaa cgactgcgcc gacccgggca actaccccaa tgattgcgac gacggcgacc    780
gcttcatcgg cggcgatgcg gacctcaaca ccggccaccc gcaggtctac ggcatgttcc    840
gcgatgaatt caccaacctg cgcagtcagt acggtgccgg cggcttccgc ttcgactttg    900
ttcggggcta tgcgccggag cgggtcaaca gctggatgac cgatagcgcc gacaacagct    960
tctgcgtcgg cgaactgtgg aaaggcccct ctgagtaccc gaactgggac tggcgcaaca   1020
ccgccagctg gcagcagatc atcaaggact ggtccgaccg ggccaagtgc ccggtgttcg   1080
acttcgccct caaggaacgc atgcagaacg ctcgatcgcc gactggaagc acgcctgaac   1140
ggcaatcccg accgcgtggg cgcgaggtgg cggtgacctt cgtcgacaac cacgacaccg   1200
gctactcgcc cgggcagaac ggtgggcagc accactgggc tctgcaggac gggctgatcc   1260
gccaggccta cgcctacatc ctcaccagcc cggtacgcc ggtggtgtac tggtcgcaca   1320
tgtacgactg gggttacggc gacttcatcc gtcagctgat ccaggtgcgt cgcgccgccg   1380
gcgtgcgcgc cgattcggcg atcagcttcc acagcggcta cagcggtctg gtcgccaccg   1440
tcagcggcag ccagcagacc ctggtggtgg cgctcaactc cgacctgggc aatcccggcc   1500
aggtggccag cggcagcttc agcgaggcg tcaacgccag caacggccag gtgcgcgtgt   1560
ggcgtagcgg cacgggcagc ggtggcggtg aacccggcgc tctggtcagt gtgagtttcc   1620
gctgcgacaa cggcgcgacg cagatgggcg acagcgtcta cgcggtcggc aacgtcagcc   1680
agctcggtaa ctggagcccg gccgcggcgt tgcgcctgac cgacaccagc ggctacccga   1740
cctggaaggg cagcattgcc ttgcctgccg gccagaacga ggaatggaaa tgcctgatcc   1800
gcaacgaggc caacgccacc caggtgcggc aatggcaggg cggggcaaac aacagcctga   1860
cgccgagcga gggcgccacc accgtcggcc ggctctagcc cgggcggcaa ctcggccgtc   1920
tcgcggatgt gaggcggctg gtctcggcgg cggtatcgtt gcgctggggg cggggccgcc   1980
gttcacgcgc cctgctatcg ctagttttcg gcgctccgcg catcggccag ttgccagcga   2040
atcgcctgcg cttcggcctg gtgcaggtcg tcgagcagcg ct                      2082
```

<210> SEQ ID NO 13
<211> LENGTH: 429
<212> TYPE: PRT
<213> ORGANISM: Artificial Sequence
<220> FEATURE:
<223> OTHER INFORMATION: Pseudomonas saccharophilia maltotetrahydrolase
      variant

<400> SEQUENCE: 13

```
Asp Gln Ala Gly Lys Ser Pro Ala Gly Val Arg Tyr His Gly Gly Asp
 1               5                  10                  15

Glu Ile Ile Leu Gln Gly Phe His Trp Asn Val Val Arg Glu Ala Pro
            20                  25                  30

Tyr Asn Trp Tyr Asn Ile Leu Arg Gln Gln Ala Ser Thr Ile Ala Ala
        35                  40                  45

Asp Gly Phe Ser Ala Ile Trp Met Pro Val Pro Trp Arg Asp Phe Ser
    50                  55                  60

Ser Trp Thr Asp Pro Gly Arg Ser Gly Gly Glu Gly Tyr Phe Trp
65                  70                  75                  80

His Asp Phe Asn Lys Asn Gly Arg Tyr Gly Ser Asp Ala Gln Leu Arg
                85                  90                  95

Gln Ala Ala Gly Ala Leu Gly Gly Ala Gly Val Lys Val Leu Tyr Asp
           100                 105                 110

Val Val Pro Asn His Met Asn Arg Asp Tyr Pro Asp Lys Glu Ile Asn
       115                 120                 125
```

```
Leu Pro Ala Gly Gln Arg Phe Trp Arg Asn Asp Cys Pro Asp Pro Gly
    130                 135                 140

Asn Tyr Pro Asn Asp Cys Asp Gly Asp Arg Phe Leu Gly Gly Glu
145                 150                 155                 160

Ser Asp Leu Asn Thr Gly His Pro Gln Ile Tyr Gly Met Phe Arg Asp
                165                 170                 175

Glu Phe Thr Asn Leu Arg Ser Gly Tyr Gly Ala Gly Gly Phe Arg Phe
                180                 185                 190

Asp Phe Val Arg Gly Tyr Ala Pro Glu Arg Val Asp Ser Trp Met Ser
            195                 200                 205

Asp Ser Ala Asp Ser Ser Phe Cys Val Gly Glu Leu Trp Lys Ala Pro
    210                 215                 220

Ser Glu Tyr Pro Ser Trp Asp Trp Arg Asn Thr Ala Ser Trp Gln Gln
225                 230                 235                 240

Ile Ile Lys Asp Trp Ser Asp Arg Ala Lys Cys Pro Val Phe Asp Phe
                245                 250                 255

Ala Leu Lys Glu Arg Met Gln Asn Gly Ser Val Ala Asp Trp Lys His
                260                 265                 270

Gly Leu Asn Gly Asn Pro Asp Pro Arg Trp Arg Glu Val Ala Val Thr
            275                 280                 285

Phe Val Asp Asn His Asp Thr Gly Tyr Ser Pro Gly Gln Asn Gly Gly
    290                 295                 300

Gln His Leu Trp Ala Leu Gln Asp Gly Leu Ile Arg Gln Ala Tyr Ala
305                 310                 315                 320

Tyr Ile Leu Thr Ser Pro Gly Thr Pro Val Val Tyr Trp Pro His Met
                325                 330                 335

Tyr Asp Trp Gly Tyr Gly Glu Phe Ile Arg Gln Leu Ile Gln Val Arg
                340                 345                 350

Arg Thr Ala Gly Val Arg Ala Asp Ser Ala Ile Ser Phe His Ser Gly
            355                 360                 365

Tyr Ser Gly Leu Val Ala Thr Val Ser Gly Ser Gln Gln Thr Leu Val
    370                 375                 380

Val Ala Leu Asn Ser Asp Leu Ala Asn Pro Gly Gln Val Ala Ser Gly
385                 390                 395                 400

Ser Phe Ser Glu Ala Val Asn Ala Ser Asn Gly Gln Val Arg Val Trp
                405                 410                 415

Arg Ser Gly Ser Gly Asp Gly Gly Asn Asp Gly Gly
            420                 425

<210> SEQ ID NO 14
<211> LENGTH: 429
<212> TYPE: PRT
<213> ORGANISM: Artificial Sequence
<220> FEATURE:
<223> OTHER INFORMATION: Pseudomonas saccharophilia maltotetrahydrolase
      variant

<400> SEQUENCE: 14

Asp Gln Ala Gly Lys Ser Pro Ala Gly Val Arg Tyr His Gly Gly Asp
1               5                   10                  15

Glu Ile Ile Leu Gln Gly Phe His Trp Asn Val Val Arg Glu Ala Pro
            20                  25                  30

Tyr Asn Trp Tyr Asn Ile Leu Arg Gln Gln Ala Ser Thr Ile Ala Ala
        35                  40                  45

Asp Gly Phe Ser Ala Ile Trp Met Pro Val Pro Trp Arg Asp Phe Ser
    50                  55                  60
```

```
Ser Trp Thr Asp Pro Gly Arg Ser Gly Gly Glu Gly Tyr Phe Trp
 65                  70                  75                  80

His Asp Phe Asn Lys Asn Ser Arg Tyr Gly Ser Asp Ala Gln Leu Arg
                 85                  90                  95

Gln Ala Ala Gly Ala Leu Gly Gly Ala Gly Val Lys Val Leu Tyr Asp
            100                 105                 110

Val Val Pro Asn His Met Asn Arg Asp Tyr Pro Asp Lys Glu Ile Asn
        115                 120                 125

Leu Pro Ala Gly Gln Arg Phe Trp Arg Asn Asp Cys Pro Asp Pro Gly
    130                 135                 140

Asn Tyr Pro Asn Asp Cys Asp Gly Asp Arg Phe Leu Gly Gly Glu
145                 150                 155                 160

Ser Asp Leu Asn Thr Gly His Pro Gln Ile Tyr Gly Met Phe Arg Asp
                165                 170                 175

Glu Phe Thr Asn Leu Arg Ser Gly Tyr Gly Ala Gly Gly Phe Arg Phe
            180                 185                 190

Asp Phe Val Arg Gly Tyr Ala Pro Glu Arg Val Asp Ser Trp Met Ser
        195                 200                 205

Asp Ser Ala Asp Ser Ser Phe Cys Val Gly Glu Leu Trp Lys Ala Pro
    210                 215                 220

Ser Glu Tyr Pro Ser Trp Asp Trp Arg Asn Thr Ala Ser Trp Gln Gln
225                 230                 235                 240

Ile Ile Lys Asp Trp Ser Asp Arg Ala Lys Cys Pro Val Phe Asp Phe
                245                 250                 255

Ala Leu Lys Glu Arg Met Gln Asn Gly Ser Val Ala Asp Trp Lys His
            260                 265                 270

Gly Leu Asn Gly Asn Pro Asp Pro Arg Trp Arg Glu Val Ala Val Thr
        275                 280                 285

Phe Val Asp Asn His Asp Thr Gly Tyr Ser Pro Gly Gln Asn Gly Gly
    290                 295                 300

Gln His Leu Trp Ala Leu Gln Asp Gly Leu Ile Arg Gln Ala Tyr Ala
305                 310                 315                 320

Tyr Ile Leu Thr Ser Pro Gly Thr Pro Val Val Tyr Trp Pro His Met
                325                 330                 335

Tyr Asp Trp Gly Tyr Gly Glu Phe Ile Arg Gln Leu Ile Gln Val Arg
            340                 345                 350

Arg Thr Ala Gly Val Arg Ala Asp Ser Ala Ile Ser Phe His Ser Gly
        355                 360                 365

Tyr Ser Gly Leu Val Ala Thr Val Ser Gly Ser Gln Gln Thr Leu Val
    370                 375                 380

Val Ala Leu Asn Ser Asp Leu Ala Asn Pro Gly Gln Val Ala Ser Gly
385                 390                 395                 400

Ser Phe Ser Glu Ala Val Asn Ala Ser Asn Gly Gln Val Arg Val Trp
                405                 410                 415

Arg Ser Gly Ser Gly Asp Gly Gly Asn Asp Gly Gly
            420                 425
```

<210> SEQ ID NO 15
<211> LENGTH: 429
<212> TYPE: PRT
<213> ORGANISM: Artificial Sequence
<220> FEATURE:
<223> OTHER INFORMATION: Pseudomonas saccharophilia maltotetrahydrolase variant

<400> SEQUENCE: 15

```
Asp Gln Ala Gly Lys Ser Pro Ala Gly Val Arg Tyr His Gly Asp
  1               5                  10                  15

Glu Ile Ile Leu Gln Gly Phe His Trp Asn Val Val Arg Glu Ala Pro
             20                  25                  30

Tyr Asn Trp Tyr Asn Ile Leu Arg Gln Gln Ala Ser Thr Ile Ala Ala
             35                  40                  45

Asp Gly Phe Ser Ala Ile Trp Met Pro Val Pro Trp Arg Asp Phe Ser
 50                  55                  60

Ser Trp Thr Asp Pro Gly Lys Ser Gly Gly Gly Gly Tyr Phe Trp
 65                  70                  75                  80

His Asp Phe Asn Lys Asn Gly Arg Tyr Gly Ser Asp Ala Gln Leu Arg
                 85                  90                  95

Gln Ala Ala Gly Ala Leu Gly Gly Ala Gly Val Lys Val Leu Tyr Asp
                100                 105                 110

Val Val Pro Asn His Met Asn Arg Asp Tyr Pro Asp Lys Glu Ile Asn
             115                 120                 125

Leu Pro Ala Gly Gln Arg Phe Trp Arg Asn Asp Cys Pro Asp Pro Gly
         130                 135                 140

Asn Tyr Pro Asn Asp Cys Asp Asp Gly Asp Arg Phe Leu Gly Gly Glu
145                 150                 155                 160

Ser Asp Leu Asn Thr Gly His Pro Gln Ile Tyr Gly Met Phe Arg Asp
                165                 170                 175

Glu Phe Thr Asn Leu Arg Ser Gly Tyr Gly Ala Gly Gly Phe Arg Phe
             180                 185                 190

Asp Phe Val Arg Gly Tyr Ala Pro Glu Arg Val Asp Ser Trp Met Ser
             195                 200                 205

Asp Ser Ala Asp Ser Ser Phe Cys Val Gly Glu Leu Trp Lys Ala Pro
 210                 215                 220

Ser Glu Tyr Pro Ser Trp Asp Trp Arg Asn Thr Ala Ser Trp Gln Gln
225                 230                 235                 240

Ile Ile Lys Asp Trp Ser Asp Arg Ala Lys Cys Pro Val Phe Asp Phe
             245                 250                 255

Ala Leu Lys Glu Arg Met Gln Asn Gly Ser Val Ala Asp Trp Lys His
             260                 265                 270

Gly Leu Asn Gly Asn Pro Asp Pro Arg Trp Arg Glu Val Ala Val Thr
             275                 280                 285

Phe Val Asp Asn His Asp Thr Gly Tyr Ser Pro Gly Gln Asn Gly Gly
         290                 295                 300

Gln His Leu Trp Ala Leu Gln Asp Gly Leu Ile Arg Gln Ala Tyr Ala
305                 310                 315                 320

Tyr Ile Leu Thr Ser Pro Gly Thr Pro Val Val Tyr Trp Pro His Met
                325                 330                 335

Tyr Asp Trp Gly Tyr Gly Asp Phe Ile Arg Gln Leu Ile Gln Val Arg
             340                 345                 350

Arg Thr Ala Gly Val Arg Ala Asp Ser Ala Ile Ser Phe His Ser Gly
         355                 360                 365

Tyr Ser Gly Leu Val Ala Thr Val Ser Gly Ser Gln Gln Thr Leu Val
     370                 375                 380

Val Ala Leu Asn Ser Asp Leu Ala Asn Pro Gly Gln Val Ala Ser Gly
385                 390                 395                 400

Ser Phe Ser Glu Ala Val Asn Ala Ser Asn Gly Gln Val Arg Val Trp
                405                 410                 415

Arg Ser Gly Ser Gly Asp Gly Gly Gly Asn Asp Gly Gly
```

<210> SEQ ID NO 16
<211> LENGTH: 21
<212> TYPE: PRT
<213> ORGANISM: Pseudomonas saccharophilia

<400> SEQUENCE: 16

Met Ser His Ile Leu Arg Ala Ala Val Leu Ala Ala Val Leu Leu Pro
1               5                   10                  15

Phe Pro Ala Leu Ala
            20

<210> SEQ ID NO 17
<211> LENGTH: 21
<212> TYPE: DNA
<213> ORGANISM: Artificial Sequence
<220> FEATURE:
<223> OTHER INFORMATION: primer

<400> SEQUENCE: 17
atgacgaggt ccttgttttt c                                             21

<210> SEQ ID NO 18
<211> LENGTH: 18
<212> TYPE: DNA
<213> ORGANISM: Artificial Sequence
<220> FEATURE:
<223> OTHER INFORMATION: primer

<400> SEQUENCE: 18
cgctagtcgt ccatgtcg                                                 18

<210> SEQ ID NO 19
<211> LENGTH: 27
<212> TYPE: DNA
<213> ORGANISM: Artificial Sequence
<220> FEATURE:
<223> OTHER INFORMATION: primer

<400> SEQUENCE: 19
gccatggatc aggccggcaa gagcccg                                       27

<210> SEQ ID NO 20
<211> LENGTH: 25
<212> TYPE: DNA
<213> ORGANISM: Artificial Sequence
<220> FEATURE:
<223> OTHER INFORMATION: primer

<400> SEQUENCE: 20
tggatcctca gaacgagccg ctggt                                         25

<210> SEQ ID NO 21
<211> LENGTH: 25
<212> TYPE: DNA
<213> ORGANISM: Artificial Sequence
<220> FEATURE:
<223> OTHER INFORMATION: primer

<400> SEQUENCE: 21
gaattcagcc gccgtcattc ccgcc                                         25

<210> SEQ ID NO 22
<211> LENGTH: 20
<212> TYPE: DNA

```
<213> ORGANISM: Artificial Sequence
<220> FEATURE:
<223> OTHER INFORMATION: primer

<400> SEQUENCE: 22
agatttacgg catgtttcgc                                                    20

<210> SEQ ID NO 23
<211> LENGTH: 20
<212> TYPE: DNA
<213> ORGANISM: Artificial Sequence
<220> FEATURE:
<223> OTHER INFORMATION: primer

<400> SEQUENCE: 23
tagccgctat ggaagctgat                                                    20

<210> SEQ ID NO 24
<211> LENGTH: 20
<212> TYPE: DNA
<213> ORGANISM: Artificial Sequence
<220> FEATURE:
<223> OTHER INFORMATION: primer

<400> SEQUENCE: 24
tgaccttcgt cgacaaccac                                                    20

<210> SEQ ID NO 25
<211> LENGTH: 20
<212> TYPE: DNA
<213> ORGANISM: Artificial Sequence
<220> FEATURE:
<223> OTHER INFORMATION: primer

<400> SEQUENCE: 25
gatagctgct ggtgacggtc                                                    20

<210> SEQ ID NO 26
<211> LENGTH: 26
<212> TYPE: DNA
<213> ORGANISM: Artificial Sequence
<220> FEATURE:
<223> OTHER INFORMATION: synthetic oligonucleotide

<400> SEQUENCE: 26
ctgccggccg gccagcgctt ctggcg                                             26

<210> SEQ ID NO 27
<211> LENGTH: 26
<212> TYPE: DNA
<213> ORGANISM: Artificial Sequence
<220> FEATURE:
<223> OTHER INFORMATION: synthetic oligonucleotide

<400> SEQUENCE: 27
cgccagaagc gctggccggc cggcag                                             26

<210> SEQ ID NO 28
<211> LENGTH: 30
<212> TYPE: DNA
<213> ORGANISM: Artificial Sequence
<220> FEATURE:
<223> OTHER INFORMATION: synthetic oligonucleotide

<400> SEQUENCE: 28
gacggtgacc gcttcctggg cggcgagtcg                                         30
```

<210> SEQ ID NO 29
<211> LENGTH: 30
<212> TYPE: DNA
<213> ORGANISM: Artificial Sequence
<220> FEATURE:
<223> OTHER INFORMATION: synthetic oligonucleotide

<400> SEQUENCE: 29
cgactcgccg cccaggaagc ggtcaccgtc            30

<210> SEQ ID NO 30
<211> LENGTH: 33
<212> TYPE: DNA
<213> ORGANISM: Artificial Sequence
<220> FEATURE:
<223> OTHER INFORMATION: synthetic oligonucleotide

<400> SEQUENCE: 30
ggcgagctgt ggaaagcccc ttctgaatat ccg        33

<210> SEQ ID NO 31
<211> LENGTH: 33
<212> TYPE: DNA
<213> ORGANISM: Artificial Sequence
<220> FEATURE:
<223> OTHER INFORMATION: synthetic oligonucleotide

<400> SEQUENCE: 31
cggatattca gaaggggctt tccacagctc gcc        33

<210> SEQ ID NO 32
<211> LENGTH: 31
<212> TYPE: DNA
<213> ORGANISM: Artificial Sequence
<220> FEATURE:
<223> OTHER INFORMATION: synthetic oligonucleotide

<400> SEQUENCE: 32
gaacggcggc cagcacctgt gggcgctgca g          31

<210> SEQ ID NO 33
<211> LENGTH: 31
<212> TYPE: DNA
<213> ORGANISM: Artificial Sequence
<220> FEATURE:
<223> OTHER INFORMATION: synthetic oligonucleotide

<400> SEQUENCE: 33
ctgcagcgcc cacaggtgct ggccgccgtt c          31

<210> SEQ ID NO 34
<211> LENGTH: 43
<212> TYPE: DNA
<213> ORGANISM: Artificial Sequence
<220> FEATURE:
<223> OTHER INFORMATION: synthetic oligonucleotide

<400> SEQUENCE: 34
gtactggccg cacatgtacg actggggcta cggcgaattc atc    43

<210> SEQ ID NO 35
<211> LENGTH: 43
<212> TYPE: DNA
<213> ORGANISM: Artificial Sequence
<220> FEATURE:
<223> OTHER INFORMATION: synthetic oligonucleotide -continued

<400> SEQUENCE: 35
gatgaattcg ccgtagcccc agtcgtacat gtgcggccag tac                43

<210> SEQ ID NO 36
<211> LENGTH: 26
<212> TYPE: DNA
<213> ORGANISM: Artificial Sequence
<220> FEATURE:
<223> OTHER INFORMATION: synthetic oligonucleotide

<400> SEQUENCE: 36
gcgaagcgcc ctacaactgg tacaac                                    26

<210> SEQ ID NO 37
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 37
ccgacggcgg caggtccggc g                                         21

<210> SEQ ID NO 38
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 38
caagaacagc cgctacggca gcgac                                     25

<210> SEQ ID NO 39
<211> LENGTH: 27
<212> TYPE: DNA
<213> ORGANISM: Artificial Sequence
<220> FEATURE:
<223> OTHER INFORMATION: synthetic oligonucleotide

<400> SEQUENCE: 39
cacatgaacc gcgactaccc ggacaag                                   27

<210> SEQ ID NO 40
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 40
cgcaacgact gcgccgaccc ggg                                       23

<210> SEQ ID NO 41
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 41
cgcgacgagt ttaccaacct gcg                                       23

<210> SEQ ID NO 42
<211> LENGTH: 34
<212> TYPE: DNA

-continued

```
<213> ORGANISM: Artificial Sequence
<220> FEATURE:
<223> OTHER INFORMATION: synthetic oligonucleotide

<400> SEQUENCE: 42
gtactggccg cacatgtacg actggggcta cggc                              34
```

US 8,143,048 B2

EXO-SPECIFIC AMYLASE POLYPEPTIDES, NUCLEIC ACIDS ENCODING THOSE POLYPEPTIDES AND USES THEREOF

CROSS-REFERENCE TO RELATED APPLICATIONS

The present application claims benefit of and priority to U.S. Ser. No. 60/485,616, entitled "Exo-specific Amylase Polypeptides, Nucleic Acids Encoding Those Polypeptides and Uses Thereof", filed Jul. 7, 2003, by Berg, et al, and U.S. Ser. No. 60/485,413, entitled, "Thermostable Amylase Polypeptides, Nucleic Acids Encoding Those Polypeptides and Uses Thereof, filed Jul. 7, 2003. These applications are related to U.S. Ser. No. 60/485,539, entitled "Polypeptides", filed Jul. 7, 2003.

FIELD OF THE INVENTION

This invention relates to amylase polypeptides, and nucleic acids encoding the polpypeptides and uses thereof. The amylases of the present invention have been engineered to have more beneficial qualities. Specifically, the amylases of the current invention show an altered exospecifity.

BACKGROUND OF THE INVENTION

Improved amylases can ameliorate problems inherent in certain processes, such as baking. Crystallisation of amylopectin takes place in starch granules days after baking, which leads to increased firmness of bread and causes bread staling. When bread stales, bread loses crumb softness and crumb moisture. As a result, crumbs become less elastic, and bread develops a leathery crust.

Enzymatic hydrolysis (by amylases, for example) of amylopectin side chains can reduce crystallization and increase anti-staling. Crystallization depends upon the length of amylopectin side chains: the longer the side chains, the greater the crystallization. Most starch granules are composed of a mixture of two polymers: amylopectin and amylose, of which about 75% is amylopectin. Amylopectin is a very large, branched molecule consisting of chains of α-D-glucopyranosyl units joined by (1-4) linkages, where the chains are attached by α-D-(1-6) linkages to form branches. Amylose is a linear chain of (1-4) linked α-D-glucopyranosyl units having few α-D-(1-6) branches.

Baking of farinaceous bread products such as white bread, bread made from bolted rye flour and wheat flour and rolls is accomplished by baking the bread dough at oven temperatures in the range of from 180 to 250° C. for about 15 to 60 minutes. During the baking process a steep temperature gradient (200→120° C.) prevails over the outer dough layers where the crust of the baked product is developed. However, due to steam, the temperature in the crumb is only about 100° C. at the end of the baking process. Above temperatures of about 85° C., enzyme inactivation can take place and the enzyme will have no anti-staling properties. Only thermostable amylases, thus, are able to modify starch efficiently during baking.

Endoamylase activity can negatively affect the quality of the final bread product by producing a sticky or gummy crumb due to the accumulation of branched dextrins. Exoamylase activity is preferred, because it accomplishes the desired modification of starch that leads to retardation of staling, with fewer of the negative effects associated with endo-amylase activity. Reduction of endoamylase activity can lead to greater exospecifity, which can reduce branched dextrins and produce a higher quality bread.

The present invention is drawn to polypeptides which have altered exospecificity.

SUMMARY OF THE INVENTION

In a first aspect, the invention provides a polypeptide comprising a PS4 variant, the PS4 variant being derivable from a parent polypeptide. The parent enzyme may preferably be a Pseudomonas saccharophila non-maltogenic exoamylase, such as the exoamlyase having the amino acid sequence set forth in SEQ ID NO:1 or SEQ ID NO:5. The parent enzyme may preferably be a Pseudomonas stutzeri non-maltogenic exoamylase, such as a polypeptide having the amino acid sequence set forth in SEQ ID NO: 7 or SEQ ID NO11. Other members of the PS4 family may be used as parent enzymes.

In preferred embodiments, the parent polypeptide is a non-maltogenic exoamylase from Pseudomonas saccharophilia having the amino acid sequence set forth in SEQ ID NO: 1 or set forth in SEQ ID NO:5. In other preferred embodiments, the parent polypeptide is a non-maltogenic exoamylase from Pseudomonas stutzeri having the amino acid sequence set forth in SEQ ID NO:7 or set forth in SEQ ID NO:11. In a preferred embodiment, the PS4 variant differs from the parent polypeptide by including amino acid substitutions, the substitutions located at a position comprising at least one position selected from the group consisting of: 4, 9, 13, 33, 34, 42, 70, 71, 87, 99, 100, 108, 113, 121, 131, 134, 135, 141, 153, 157, 158, 160, 161, 166, 170, 171, 178, 179, 184, 188, 198, 199, 221, 223, 238, 270, 277, 290, 307, 315, 334, 335, 342, 343, 372, 392, 398, 399, 405, 415, 425, wherein reference to position numbering is with respect to the Pseudomonas saccharophilia sequence shown as SEQ ID NO: 1. In a preferred embodiment, the PS4 variant differs from the parent polypeptide by including amino acid substitutions, the substitutions located at a position comprising at least one position selected from the group consisting of: 4, 33, 34, 70, 71, 87, 99, 108, 113, 121, 131, 134, 141, 157, 158, 171, 178, 179, 188, 198, 199, 223, 290, 307, 315, 334, 343, 399, and 405, wherein reference to position numbering is with respect to the Pseudomonas saccharophilia sequence shown as SEQ ID NO: 1. Preferably, the position is at least one position selected from the group consisting of: 33, 34, 71, 87, 121, 134, 141, 157, 178, 179, 223, 307, 334, and 343. Preferably the PS4 variant comprises at least one substitution selected from the group consisting of N33Y, D34N, K71R, G87S, G121D, G134R, A141P, L178F, A179T, G223A, H307L, S334P, and D343E.

In another embodiment, the exoamylase further comprises at least one additional substitution at a position selected from 108, 158, 171 and 188. Preferably the PS4 variant comprises at least one substitution selected from the group consisting of K108R, G158D, Y171S, and G188A.

Preferably, the PS4 variant comprises at least one substitution selected from the group consisting of: G4D, N33Y, D34N, G70D, K71R, G87S, A99V, K108R, V113I, G121D, G134R, A141P, I157L, G158D, Y171S, L178F, A179T, G188A, Y198F, Y198L, A199V, G223A, V290I, H307L, I315V, S334P, D343E, S399P, A405F, and A405E. Preferably the PS4 variant comprises the following substitutions: N33Y, D34N, G134R, A141P, I157L, G223A, H307L and S334P with at least one additional substitution of L178F or A179T. Preferably the PS4 variant comprises at least one of the following substitutions: N33Y, D34N, I157L, L178F, A179T, G223A or H307L. Preferably, the PS4 variant comprises at least one of the following substitutions: G87S, G134R, A141P, or S334P.

In other preferred embodiments, the PS4 variant polypeptide comprises a combination selected from:
G134R, A141P I157L G223A H307L S334P D343E G121D;
G134R A141P I157L G223A H307L S334P D343E N33Y G121D;
G134R A141P I157L G223A H307L S334P D343E N33Y;
G134R, A141P I157L G223A H307L S334P D343E N33Y D34N K71R L178F A179T G87S G121D S214N T375A;
G134R, A141P I157L G223A H307L S334P D343E N33Y D34N K71R L178F A179T G121D Y171S G188A N138D;
G134R, A141P I157L G223A H307L S334P D343E N33Y D34N K71R L178F A179T G121D;
G87S G121D G134R, A141P I157L G223A H307L S334P D343E N33Y D34N K71R L178F A179T;
G87S G121D G134R, A141P I157L G223A H307L S334P D343E N33Y D34N K71R L178F A179T G188A;
G134R, A141P I157L G223A H307L S334P K71R L178F A179T;
G134R, A141P I157L G223A H307L S334P L178F A179T;
G134R, A141P I157L G223A H307L S334P N33Y D34N L178F A179T;
G134R, A141P I157L G223A H307L S334P L178F A179T G87S G121D;
G134R, A141P I157L G223A H307L S334P L178F A179T G121D;
G134R, A141P I157L G223A H307L S334P D343E N33Y D34N K71R L178F A179T G121D E343D;
G87S G121D G134R, A141P I157L G223A H307L S334P D343E N33Y D34N K71R L178F A179T;
G87S G121D G134R, A141P I157L G223A H307L S334P D343E N33Y D34N K71R L178F A179T Y33N N34D E343D;
G134R, A141P I157L G223A H307L S334P D343E N33Y D34N K71R L178F A179T G121D;
G134R, A141P I157L G223A H307L S334P K71R L178F A179T G121D;
G87S, V113I, G134R, A141P, I157L, Y198F, G223A, V290I, H307L, S334P, D343E;
113F, A141P, I157L, Y198F, G223A, V290I, H307L, S334P, D343E;
A99V, V113I, A141P, I157L, Y198F, G223A, V290I, H307L, S334P, D343E;
V113I, I157L, Y198F, G223A, V290I, H307L, S334P, D343E V113I, G134R, A141P, I157L, Y198F, G223A, V290I, H307L, S334P, D343E;
A141P, I157L, Y198F, G223A, V290I, H307L, S334P, D343E;
A199V, D343E, V113I, A141P, I157L, Y198F, G223A, V290I, H307L, S334P;
V113I, A141P, I157L, Y198F, G223A, V290I, S334P, D343E;
V113I, G121D, G134R, A141P, I157L, Y198F, G223A, V290I, H307L, S334P, D343E;
V113I, G121D, G134R, A141P, I157L, Y198F, G223A, V290I, H307L, S334P, D343E;
V113I, A141P, I157L, Y198F, G223A, V290I, H307L, S334P, D343E;
V113I, A141P, Y198F, G223A, V290I, H307L;
V113I, A141P, Y198F, G223A, V290I, S334P, D343E;
V113I, A141P, Y198F, G223A, A268P, V290I, S399P V113I, A141P, Y198F, G223A, V290I, S399P;
V113I, A141P, Y198W, G223A, V290I;
V113I, A141P, Y198F, G223A, V290I;
Y198F, G223A, V290I;
Y198W, G223A, V290I;
V113I, A141P, I157L, Y198F, G223A, V290I;
V113M;
V113A;
V113I, G134R, A141P, I157L, Y198F, G223A, V290I, H307L, S334P, D343E;
V113I, G134R, A141P, I157L, Y198F, G223A, V290I, H307L, I315V, S334P, D343E;
D34N, V113I, G134R, A141P, I157L, Y198F, G223A, V290I, H307L, S334P, D343E;
V113I, G134R, A141P, I157L, G188S, Y198F, G223A, V290I, H307L, S334P, D343E;
K71R, V113I, G134R, A141P, I157L, L178L, Y198F, G223A, V290I, H307L, G313G, S334P, D343E;
D34N, V113I, G134R, A141P, I157L, Y198F, G223A, V290I, H307L, G313G, S334P, D343E; V113I, G134R, A141P, I157L, A179V, Y198F, G223A, V290I, H307L, S334P, D343E;
V113I, G134R, A141P, I157L, I170I, Y198F, G223A, V290I, H307L, G313G, S334P, D343E V113I, G134R, A141P, I157L, A179V, Y198F, G223A, V290I, H307L, G313G, S334P, D343E;
G87S, V113I, G134R, A141P, I157L, Y198F, G223A, V290I, H307L, S334P, D343E;
V113I, G134R, A141P, I157L, Y198F, G223A, V290I, H307L, S334P, D343E, A405E;
V113I, G134R, A141P, I157L, Y198F, G223A, V290I, H307L, S334P, D343E, A405V;
A141P, I157L, Y198F, G223A, V290I, H307L, S334P, D343E;
V113I, G134R, A141P, I157L, Y198L, G223A, V290I, H307L, S334P, D343E;
V113I, G134R, A141P, I157L, Y198F, G223A, V290I, H307L, S334P, D343E;
K71R, V113I, G134R, A141P, I157L, Y198F, G223A, V290I, H307L, S334P, D343E;
K108R, V113I, G134R, A141P, I157L, Y198F, G223A, V290I, H307L, S334P, D343E;
D34G, V113I, G134R, A141P, I157L, Y198F, G223A, V290I, H307L, S334P, D343E;
G4D, V113I, A141P, I157L, Y198F, G223A, V290I, H307L, S334P, D343E; and A141P, G134R, G223A, H307L, I157L, V113I, V290I, Y198F, G188A;

In other preferred embodiments, the PS4 variant polypeptide comprises a combination selected from:
G134R, A141P, I157L, G223A, H307L and S334P;
G121D, G134R, A141P, I157L, G223A, H307L and S334P;
G87S, G121D, G134R, A141P, I157L, G223A, H307L and S334P;
G134R, A141P, I157L, L178F, A179T, G223A, H307L and S334P;
G87S, G121D, G134R, A141P, I157L, L178F, A179T, G223A, H307L and S334P;
G121D, G134R, A141P, I157L, L178F, A179T, G223A, H307L and S334P;
N33Y, D34N, G134R, A141P, I157L, L178F, A179T, G223A, H307L and S334P; N33Y,
D34N, G121D, G134R, A141P, I157L, L178F, A179T, G223A, H307L and S334P; and
N33Y, D34N, G87S, G121D, G134R, A141P, I157L, L178F, A179T, G223A, H307L and S334P.

In other preferred embodiments, the PS4 variant polypeptide comprises a combination selected from the following:
N33Y, D34N, G134R, A141P, I157L, L178F, A179T, G223A, H307L and S334P;
N33Y, D34N, G87S, G121D, G134R, A141P, I157L, L178F, A179T, G223A, H307L and S334P; and N33Y, D34N, G87S, G121D, G134R, A141P, I157L, L178F, A179T, G223A, H307L and S334P In preferred embodiments, the PS4 variant is an amino acid comprising the sequence set forth in either SEQ ID NO:2; SEQ ID NO:3; SEQ ID NO:4; SEQ ID NO 4a, SEQ ID NO 4b, SEQ ID NO 4c, SEQ ID NO:8, SEQ ID NO:9 or SEQ ID NO: 10.

The PS4 variant can be derived from a *Pseudomonas* sp. In an embodiment, the *Pseudomonas* species is selected from *Pseudomonas saccharophila* and *Pseudomonas stutzeri*.

The PS4 variant polypeptide may comprise one or more mutations in addition to those set out above. Other mutations, such as deletions, insertions, substitutions, transversions, transitions and inversions, at one or more other locations, may also be included. Likewise, the polypeptide may be missing at least one of the substitutions set forth above.

In a preferred embodiment, the polypeptide is truncated. The truncation may be at the N-terminal end or the C-terminal end. The parent enzyme or PS4 variant may lack one or more portions, such as sub-sequences, signal sequences, domains or moieties, whether active or not. For example, the parent enzyme or the PS4 variant polypeptide may lack a signal sequence, as described herein. Alternatively, or in addition, the parent enzyme or the PS4 variant may lack one or more catalytic or binding domains. In preferred embodiments, the parent enzyme or PS4 variant may lack one or more of the domains present in non-maltogenic exoamylases, such as the starch binding domain. For example, the PS4 polypeptides may have only sequence up to position 429, relative to the numbering of a *Pseudomonas saccharophila* non-maltogenic exoamylase shown as SEQ ID NO: 1. In a preferred embodiment, the PS4 variants pSac-d34 (SEQ ID NO 4c, FIG. 8c), pSac-D20 (SEQ ID NO 4a, FIG. 8a) and pSac-D14 (SEQ ID NO 4b, FIG. 8b) are provided, the variants having an amino acids sequences as set forth in the Figures.

The PS4 variant may also comprise a homologous sequence. A homologous sequence comprises a nucleotide sequence at least 75, 80, 85 or 90% identical, preferably at least 95, 96, 97, 98 or 99% identical to a nucleotide sequence encoding a PS4 variant polypeptide enzyme.

Preferred embodiments also include functional equivalents. The PS4 variant polypeptides described in this document are derived from, or are variants of, polypeptides preferably exhibiting non-maltogenic exoamylase activity. Preferably, the parent enzymes are non-maltogenic exoamylases themselves. The PS4 variant polypeptides in preferred embodiments also exhibit non-maltogenic exoamylase activity.

The PS4 variants described herein will preferably have exospecificity, for example measured by exo-specificity indices, as described herein, consistent with their being exoamylases. Moreover, they preferably have higher or increased exospecificity when compared to the parent enzymes or polypeptides from which they are derived. Thus, for example, the PS4 variant polypeptides may have an exo-specificity index of 20 or more, i.e., its total amylase activity (including exo-amylase activity) is 20 times or more greater than its endoamylase activity. In preferred embodiments, the exo-specificity index of exoamylases is 30 or more, 40 or more, 50 or more, 60 or more, 70 or more, 80 or more, 90 or more, or 100 or more. In preferred embodiments, the exo-specificity index is 150 or more, 200 or more, 300 or more, or 400 or more.

Preferably, the PS4 variant will be more thermostable than the parent. Preferably, the PS4 variant polypeptide is capable of degrading starch at temperatures of from about 55° C. to about 80° C. or more. Preferably, the PS4 variant retains its activity after exposure to temperatures of up to about 95° C. The PS4 variant polypeptides described here have half lives extended relative to the parent enzyme by preferably 10%, 20%, 30%, 40%, 50%, 60%, 70%, 80%, 90%, 100%, 200% or more, preferably at elevated temperatures of from 55° C. to about 95° C. or more, preferably at about 80° C. Preferably, the sample is heated for 1-10 minutes at 80° C. or higher.

Preferably, the PS4 variant polypeptide is more pH stable. Preferably, it has a higher pH stability than its cognate parent polypeptide. Preferably, the PS4 variant polypeptide is capable of degrading starch at a pH of from about 5 to about 10.5. The PS4 variant polypeptides may have 10%, 20%, 30%, 40%, 50%, 60%, 70%, 80%, 90%, 100%, 200% or longer half life when compared to their parent polypeptides under identical pH conditions. In another embodiment, the degree of pH stability may be assayed by measuring the activity or specific activity of the enzyme in specific pH conditions. The specific pH conditions may be any pH from pH5 to pH10.5.

In preferred embodiments, the functional equivalents will have sequence homology to at least one of the PS4 family members. Functional equivalents will have sequence homology to either of the *Pseudomonas saccharophila* and *Pseudomonas stutzeri* non-maltogenic exoamylases mentioned above, preferably both. The functional equivalent may also have sequence homology with any of the sequences set out as SEQ ID NOs: 1 to 12, preferably SEQ ID NO: 1 or SEQ ID NO: 7 or both. Sequence homology is preferably at least 60%, preferably 65% or more, preferably 75% or more, preferably 80% or more, preferably 85% or more, preferably 90% or more, preferably 95% or more. Sequence homologies may be generated by any or all of the programs set forth herein. In other embodiments, the functional equivalents will be capable of specifically hybridising to any of the sequences set out above.

In a second aspect, the invention provides a nucleic acid, the nucleic acid encoding a polypeptide comprising a.PS4 variant being derivable from a parent polypeptide, as set forth above. The parent enzyme may preferably be a *Pseudomonas saccharophila* non-maltogenic exoamylase as set forth in SEQ ID NO:1 or as set forth in SEQ ID NO:5. The parent enzyme may preferably be a *Pseudomonas stutzeri* non-maltogenic exoamylase, as set forth in SEQ ID NO: 7 or as set forth in SEQ ID NO11. Other members of the PS4 family may be used as parent enzymes.

In preferred embodiments, the parent polypeptide is a non-maltogenic exoamylase from *Pseudomonas saccharophila* non-maltogenic exoamylase having a sequence as set forth in SEQ ID NO: 1 or as set forth in SEQ ID NO:5. In other preferred embodiments, the parent polypeptide comprises a non-maltogenic exoamylase from *Pseudomonas stutzeri* having a sequence shown as set forth in SEQ ID NO:7 or as set forth in SEQ ID NO:11. In a preferred embodiment, the nucleic acid encoding the PS4 variant differs from the parent nucleic acid by encoding amino acid substitutions, the substitutions located at a position comprising at least one position selected from the group consisting of: 4, 9, 13, 33, 34, 42, 70, 71, 87, 99, 100, 108, 113, 121, 131, 134, 135, 141, 153, 157, 158, 160, 161, 166, 170, 171, 178, 179, 184, 188, 198, 199, 221, 223, 238, 270, 277, 290, 307, 315, 334, 335, 342, 343, 372, 392, 398, 399, 405, 415, 425, wherein reference to position numbering is with respect to a *Pseudomonas saccharophila* sequence set forth in SEQ ID NO: 1. Preferably, the positions are at least one position selected from the group consisting of: 33, 34, 87, 121, 134, 141, 157, 178, 179, 223, 307 and 334.

Preferably, the nucleic acid encoding the PS4 variant comprises a nucleic acid encoding at least one substitution in the polypeptide, the substitution selected from the group consisting of: N33Y, D34N, G87S, G121D, G134R, A141P, I157L, L178F, A179T, G223A, H307L and S334P. Preferably, the nucleic acid encoding the PS4 variant comprises the following substitutions: N33Y, D34N, G134R, A141P, I157L, G223A, H307L and S334P with at least one additional substitution of L178F or A179T. Preferably, the nucleic acid encoding the PS4 variant comprises one of the following substitutions: N33Y, D34N, I157L, L178F, A179T, G223A or H307L. Preferably, the nucleic acid encoding the PS4 variant comprises one of the following substitutions: G87S, G134R, A141P, or S334P. In another embodiment, the nucleic acid encoding the PS4 variant comprises a nucleic acid encoding at least one of the following substitutions: K71R, K108R, G158D, Y171S, G188A, and D343E.

In another embodiment, the nucleic acid encoding the PS4 variant comprises a nucleic acid encoding at least one of the following combinations: G134R, A141P I157L G223A H307L S334P D343E G121D;
G134R A141P I157L G223A H307L S334P D343E N33Y G121D;
G134R A141P I157L G223A H307L S334P D343E N33Y;
G134R, A141P I157L G223A H307L S334P D343E N33Y D34N K71R L178F A179T G87S G121D S214N T375A;
G134R, A141P I157L G223A H307L S334P D343E N33Y D34N K71R L178F A179T G121D Y171S G188A N138D;

G134R, A141P I157L G223A H307L S334P D343E N33Y D34N K71R L178F A179T G121D;

G87S G121D G134R, A141P I157L G223A H307L S334P D343E N33Y D34N K71R L178F A179T;

G87S G121D G134R, A141P I157L G223A H307L S334P D343E N33Y D34N K71R L178F A179T G188A;

G134R, A141P I157L G223A H307L S334P K71R L178F A179T;

G134R, A141P I157L G223A H307L S334P L178F A179T;

G134R, A141P I157L G223A H307L S334P N33Y D34N L178F A179T;

G134R, A141P I157L G223A H307L S334P L178F A179T G87S G121D;

G134R, A141P I157L G223A H307L S334P L178F A179T G121D;

G134R, A141P I157L G223A H307L S334P D343E N33Y D34N K71R L178F A179T G121D E343D;

G87S G121D G134R, A141P I157L G223A H307L S334P D343E N33Y D34N K71R L178F A179T;

G87S G121D G134R, A141P I157L G223A H307L S334P D343E N33Y D34N K71R

L178F A179T Y33N N34D E343D;

G134R, A141P I157L G223A H307L S334P D343E N33Y D34N K71R L178F A179T G121D;

G134R, A141P I157L G223A H307L S334P K71R L178F A179T G121D;

G87S, V113I, G134R, A141P, I157L, Y198F, G223A, V290I, H307L, S334P, D343E;

113F, A141P, I157L, Y198F, G223A, V290I, H307L, S334P, D343E;

A99V, V113I, A141P, I157L, Y198F, G223A, V290I, H307L, S334P, D343E;

V113I, I157L, Y198F, G223A, V290I, H307L, S334P, D343E V113I, G134R, A141P, I157L, Y198F, G223A, V290I, H307L, S334P, D343E;

A141P, I157L, Y198F, G223A, V290I, H307L, S334P, D343E;

A199V, D343E, V113I, A141P, I157L, Y198F, G223A, V290I, H307L, S334P;

V113I, A141P, I157L, Y198F, G223A, V290I, S334P, D343E;

V113I, G121D, G134R, A141P, I157L, Y198F, G223A, V290I, H307L, S334P, D343E;

V113I, G121D, G134R, A141P, I157L, Y198F, G223A, V290I, H307L, S334P, D343E;

V113I, A141P, I157L, Y198F, G223A, V290I, H307L, S334P, D343E;

V113I, A141P, Y198F, G223A, V290I, H307L;

V113I, A141P, Y198F, G223A, V290I, S334P, D343E;

V113I, A141P, Y198F, G223A, A268P, V290I, S399P V113I, A141P, Y198F, G223A, V290I, S399P;

V113I, A141P, Y198W, G223A, V290I;

V113I, A141P, Y198F, G223A, V290I;

Y198F, G223A, V290I;

Y198W, G223A, V290I;

V113I, A141P, I157L, Y198F, G223A, V290I;

V113M;

V113A;

V113I, G134R, A141P, I157L, Y198F, G223A, V290I, H307L, S334P, D343E;

V113I, G134R, A141P, I157L, Y198F, G223A, V290I, H307L, I315V, S334P, D343E;

D34N, V113I, G134R, A141P, I157L, Y198F, G223A, V290I, H307L, S334P, D343E;

V113I, G134R, A141P, I157L, G188S, Y198F, G223A, V290I, H307L, S334P, D343E;

K71R, V113I, G134R, A141P, I157L, L178L, Y198F, G223A, V290I, H307L, G313G, S334P, D343E;

D34N, V113I, G134R, A141P, I157L, Y198F, G223A, V290I, H307L, G313G, S334P, D343E; V113I, G134R, A141P, I157L, A179V, Y198F, G223A, V290I, H307L, S334P, D343E;

V113I, G134R, A141P, I157L, I170I, Y198F, G223A, V290I, H307L, G313G, S334P, D343E V113I, G134R, A141P, I157L, A179V, Y198F, G223A, V290I, H307L, G313G, S334P, D343E;

G87S, V113I, G134R, A141P, I157L, Y198F, G223A, V290I, H307L, S334P, D343E;

V113I, G134R, A141P, I157L, Y198F, G223A, V290I, H307L, S334P, D343E, A405E;

V113I, G134R, A141P, I157L, Y198F, G223A, V290I, H307L, S334P, D343E, A405V;

A141P, I157L, Y198F, G223A, V290I, H307L, S334P, D343E;

V113I, G134R, A141P, I157L, Y198L, G223A, V290I, H307L, S334P, D343E;

V113I, G134R, A141P, I157L, Y198F, G223A, V290I, H307L, S334P, D343E;

K71R, V113I, G134R, A141P, I157L, Y198F, G223A, V290I, H307L, S334P, D343E;

K108R, V113I, G134R, A141P, I157L, Y198F, G223A, V290I, H307L, S334P, D343E;

D34G, V113I, G134R, A141P, I157L, Y198F, G223A, V290I, H307L, S334P, D343E;

G4D, V113I, A141P, I157L, Y198F, G223A, V290I, H307L, S334P, D343E; and

A141P, G134R, G223A, H307L, I157L, V113I, V290I, Y198F, G188A;

G134R, A141P, I157L, G223A, H307L and S334P;

G121D, G134R, A141P, I157L, G223A, H307L and S334;

G87S, G121D, G134R, A141P, I157L, G223A, H307L and S334P;

G134R, A141P, I157L, L178F, A179T, G223A, H307L and S334P;

G87S, G121D, G134R, A141P, I157L, L178F, A179T, G223A, H307L and S334P;

G121D, G134R, A141P, I157L, L178F, A179T, G223A, H307L and S334P;

N33Y, D34N, G134R, A141P, I157L, L178F, A179T, G223A, H307L and S334P; N33Y,

D34N, G121D, G134R, A141P, I157L, L178F, A179T, G223A, H307L and S334P; and

N33Y, D34N, G87S, G121D, G134R, A141P, I157L, L178F, A179T, G223A, H307L and S334P;

N33Y, D34N, G134R, A141P, I157L, L178F, A179T, G223A, H307L and S334P;

N33Y, D34N, G87S, G121D, G134R, A141P, I157L, L178F, A179T, G223A, H307L and S334P; and N33Y, D34N, G87S, G121D, G134R, A141P, I157L, L178F, A179T, G223A, H307L and S334P In preferred embodiments, the nucleic acid encoding the PS4 variant encodes an amino acid sequence comprising either SEQ ID NO:2; SEQ ID NO:3; SEQ ID NO:4; SEQ ID NO:4a; SEQ ID NO:4b; SEQ ID NO:4c; SEQ ID NO:8, SEQ ID NO:9 or SEQ ID NO:10.

In a preferred embodiment, the nucleic acid encodes a truncated polypeptide. The truncation may be at the N-terminal end or the C-terminal end. The parent enzyme or PS4 variant may lack one or more portions, such as sub-sequences, signal sequences, domains or moieties, whether active or not. For example, the parent enzyme or the PS4 variant polypeptide may lack a signal sequence. Alternatively, or in addition, the parent enzyme or the PS4 variant may lack one or more catalytic or binding domains. In a preferred embodiment, the parent enzyme or PS4 variant may lack one or more of the domains present in non-maltogenic exoamylases, such as the starch binding domain. For example, the PS4 polypeptides may have only sequence up to position 429, relative to the numbering of a *Pseudomonas saccharophila* non-maltogenic exoamylase shown as SEQ ID NO: 1. In a preferred embodiment, the nucleic acid encodes the PS4 variants pSac-d34, pSac-D20 and pSac-D14 as set forth in the Figures.

The nucleic acid encoding the PS4 variant polypeptide may comprise one or more mutations in addition to those set out above. Other mutations, such as deletions, insertions, substitutions, transversions, transitions and inversions, at one or more other locations, may also be included. Likewise, the polypeptide encoded by the nucleic acid may be missing at least one of the substitutions set forth above.

The nucleic acid encoding the PS4 variant may also comprise a homologous sequence. A homologous sequence comprises a nucleotide sequence at least 75, 80, 85 or 90% identical, preferably at least 95, 96, 97, 98 or 99% identical to a nucleotide sequence encoding a PS4 variant polypeptide enzyme.

Preferred embodiments also include a nucleic acid encoding a polypeptide which is a functional equivalent of a PS4 variant. The nucleic acids encoding PS4 variant polypeptides described in this document are derived from, or are variants of, nucleic acids which preferably encode an enzyme having non-maltogenic exoamylase activity. Preferably, the parent enzymes encoded by the nucleic acids are non-maltogenic exoamylases themselves.

The PS4 variant polypeptides encoded by the nucleic acids in preferred embodiments also exhibit non-maltogenic exoamylase activity.

The PS4 variants encoded by the nucleic acids will preferably have exospecificity, for example measured by exo-specificity indices, as described herein. Moreover, they preferably have higher or increased exospecificity when compared to the parent enzymes or polypeptides from which they are derived, preferably under identical conditions. Thus, for example, the PS4 variant polypeptides may have 10%, 20%, 30%, 40%, 50%, 60%, 70%, 80%, 90%, 100%, 200% or higher exo-specificity index. They may have 1.5× or higher, 2× or higher, 5× or higher, 10× or higher, 50× or higher, 100× or higher, when compared to their parent polypeptides, preferably under identical conditions.

Preferably, the PS4 variant encoded by the nucleic acid will be more thermostable than the parent counterpart. Preferably, the PS4 variant polypeptide is capable of degrading starch at temperatures of from about 55° C. to about 80° C. or more. Preferably, the PS4 variant retains its activity after exposure to temperatures of up to about 95° C. The PS4 variant polypeptides described here have half lives extended relative to the parent enzyme by preferably 10%, 20%, 30%, 40%, 50%, 60%, 70%, 80%, 90%, 100%, 200% or more, preferably at elevated temperatures of from 55° C. to about 95° C. or more, preferably at about 80° C. Preferably, the sample is heated for 1-10 minutes at 80° C. or higher.

Preferably, the PS4 variant polypeptide encoded by the nucleic acid is pH stable. Preferably, it has a higher pH stability than its parent polypeptide. Preferably, the PS4 variant polypeptide is capable of degrading starch at a pH of from about 5 to about 10.5. The specific pH conditions may be any pH from pH5 to pH10.5. The PS4 variant polypeptide encoded by the nucleic acid may have a longer half life, or a higher activity (depending on the assay) when compared to the parent polypeptide under identical conditions. The PS4 variant polypeptide may have 10%, 20%, 30%, 40%, 50%, 60%, 70%, 80%, 90%, 100%, 200% or longer half life when compared to their parent polypeptide under identical pH conditions. Alternatively, or in addition, they may have higher activity when compared to the parent polypeptide under identical pH conditions.

In a preferred embodiment, the functional equivalents encoded by the nucleic acid will have sequence homology to at least one of the PS4 family members. Functional equivalents will have sequence homology to either of the *Pseudomonas saccharophila* and *Pseudomonas stutzeri* non-maltogenic exoamylases mentioned above, preferably both, in a preferred embodiment. The functional equivalent may also have sequence homology with any of the sequences set out as SEQ ID NOs: 1 to 12, preferably SEQ ID NO: 1 or SEQ ID NO: 7 or both. Sequence homology is preferably at least 60%, preferably 65% or more, preferably 75% or more, preferably 80% or more, preferably 85% or more, preferably 90% or more, preferably 95% or more.

In other embodiments, a nucleic acid complementary to a nucleic acid encoding any of the PS4 variants set forth herein is provided. Additionally, a nucleic acid capable of hybridising to the complement is provided. In a preferred embodiment, a nucleic acid encoding the functional equivalents will be capable of specifically hybridising to any of the sequences set out above is provided herein, as well as its complement.

In a preferred embodiment, the sequence for use in the methods and compositions described here is a synthetic sequence. It includes, but is not limited to, sequences made with optimal codon usage for host organisms—such as the methylotrophic yeasts *Pichia* and *Hansenula*.

A third aspect of the invention provides for compositions comprising at least one PS4 variant polypeptide and another ingredient. The other ingredient may be an enzyme selected from the group consisting of oxidoreductases, hydrolases, lipases, esterases, glycosidases, amylases, pullulanases, xylanases, cellulases, hemicellulases, starch degrading enzymes, proteases and lipoxygenases. In a preferred embodiment, the composition comprises at least one PS4 variant and a maltogenic amylase from *Bacillus*, as disclosed in WO91/04669. A preferred embodiment comprises a PS4 variant and flour.

The further enzyme can be added together with any dough ingredient including the flour, water or optional other ingredients or additives or the dough improving composition. The further enzyme can be added before or after the flour, water and optionally other ingredients and additives or the dough improving composition. The further enzyme may be a liquid preparation or in the form of a dry composition.

A fourth aspect provides vectors comprising a PS4 variant polypeptide, cells comprising a PS4 variant polypeptide and methods of expressing a PS4 variant polypeptide. In a preferred embodiment, the invention is directed to a recombinant replicable vector with a nucleic acid encoding a PS4 variant polypeptide. The vector may additionally comprise any of the elements set forth herein. Another preferred embodiment provides a host cell comprising a nucleic acid encoding a PS4 variant. The host cell may be any of the bacterial, fungal or yeast cells set forth herein. In a preferred embodiment, the invention is drawn to a method of expression of a PS4 polypeptide, as provided herein.

Further aspects of the invention may be found in the related applications, having attorney docket numbers 674510-2007 and GC806P, which are incorporated by reference, herein, including any drawings, references and Figures.

BRIEF DESCRIPTION OF THE DRAWINGS

FIG. 5 shows a PS4 (SEQ ID NO: 1) reference sequence, derived from *Pseudomonas saccharophila* maltotetrahydrolase amino acid sequence.

FIG. 6 shows the sequence of a PS4 variant (SEQ ID NO: 2); *Pseudomonas saccharophila* maltotetrahydrolase amino acid sequence with substitutions G134R, A141P, I157L, G223A, H307L, S334P, N33Y, D34N, L178F and A179T.

FIG. 7 shows the sequence of a PS4 variant (SEQ ID NO: 3); *Pseudomonas saccharophila* maltotetrahydrolase amino acid sequence with substitutions G134R, A141P, I157L, G223A, H307L, S334P, N33Y, D34N, L178F, A179T and G121D.

FIG. 8A shows the sequence of PS4 variant (SEQ ID NO: 4); *Pseudomonas saccharophila* maltotetrahydrolase amino acid sequence with substitutions G134R, A141P, I157L, G223A, H307L, S334P, N33Y, D34N, L178F, A179T, G121D and G87S.

FIG. 8B shows the sequence of PSac-D20 sequence (SEQ ID NO 4a); *Pseudomonas saccharophila* maltotetrahydrolase amino acid sequence with 13 substitutions and deletion of the starch binding domain.

FIG. 8C shows the sequence of PSac-D14 sequence (SEQ ID NO 4b); *Pseudomonas saccharophila* maltotetrahydrolase amino acid sequence with 14 substitutions and deletion of the starch binding domain.

FIG. 8D shows the sequence of Psac-D34 sequence; *Pseudomonas saccharophila* maltotetrahydrolase amino acid sequence with 11 substitutions and deletion of the starch binding domain.

FIG. 9 shows an amino acid sequence of *Pseudomonas saccharophila* maltotetrahydrolase (SEQ ID NO: 5). *Pseudomonas saccharophila* Glucan 1,4-alpha-maltotetrahydrolase precursor (EC 3.2.1.60) (G4-amylase) (Maltotetraose-forming amylase) (Exo-maltotetraohydrolase)(Maltotetraose-forming exo-amylase). SWISS-PROT accession number P22963.

FIGS. 10A and 10B shows a nucleic acid sequence of *Pseudomonas saccharophila* maltotetrahydrolase (SEQ ID NO: 6). *P. saccharophila* mta gene encoding maltotetraohydrolase (EC number=3.2.1.60). GenBank accession number X16732.

FIG. 11 shows an amino acid sequence of *Pseudomonas stutzeri* maltotetrahydrolase (SEQ ID NO:7).

FIG. 12 shows the sequence of PStu-D34 (SEQ ID NO: 8); *Pseudomonas stutzeri* maltotetrahydrolase amino acid sequence with substitutions G134R, A141P, I157L, G223A, H307L, S334P, N33Y, D34N.

FIG. 13 shows the sequence of PStu-D20 (SEQ ID NO: 9); *Pseudomonas stutzeri* maltotetrahydrolase amino acid sequence with G134R, A141P, I157L, G223A, H307L, S334P, N33Y, D34N and G121D.

FIG. 14 shows the sequence of PStu-D14 (SEQ ID NO: 10); *Pseudomonas stutzeri* maltotetrahydrolase amino acid sequence with G134R, A141P, I157L, G223A, H307L, S334P, N33Y, D34N, G121D and G87S.

FIG. 15 shows the sequence of *Pseudomonas stutzeri* (*Pseudomonas perfectomarina*) (SEQ ID NO: 11). Glucan 1,4-alpha-maltotetrahydrolase precursor (EC 3.2.1.60) (G4-amylase) (Maltotetraose-forming amylase) (Exo-maltotetraohydrolase)(Maltotetraose-forming exo-amylase). SWISS-PROT accession number P13507.

FIG. 16 shows the sequence of *Pseudomonas stutzeri* maltotetrahydrolase nucleic acid sequence. *P. stutzeri* maltotetraose-forming amylase (amyP) gene, complete cds. GenBank accession number M24516 (SEQ ID NO: 12).

DETAILED DESCRIPTION OF THE PREFERRED EMBODIMENTS

Figure 1:
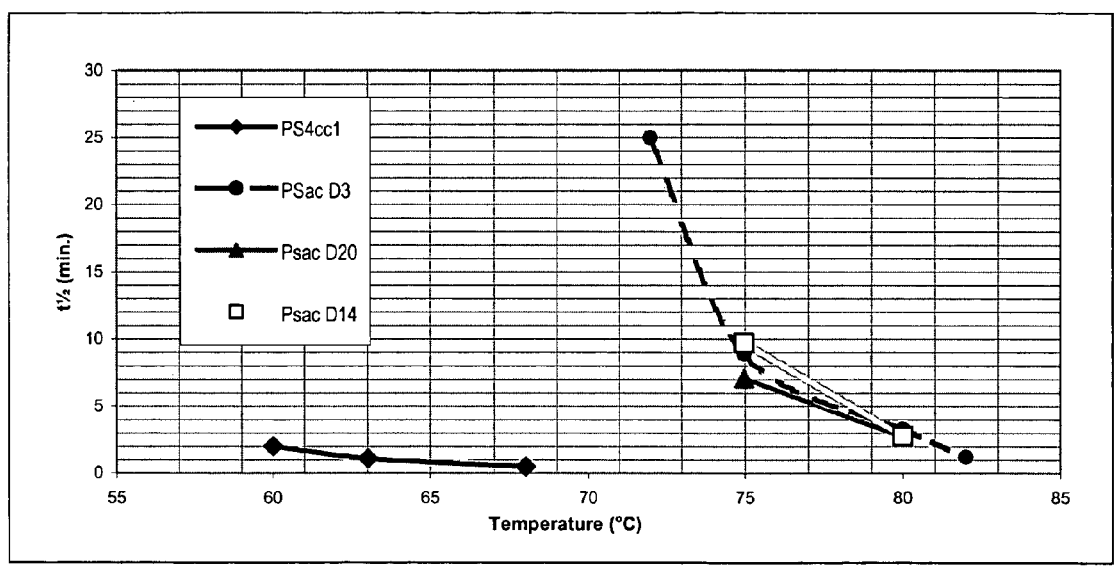
FIG. 1 is a graph showing thermostability improvement of the PS4 variants. PS4cc1 is an expressed control enzyme derived from *Pseudomonas saccharophilia*, without signal sequence and lacking the starch binding domain. Half life in minutes is plotted against temperature in degrees C. for PS4cc1, pSac-D3, pSac-D20 and pSac-D14.

The practice of the present invention will employ, unless otherwise indicated, conventional techniques of chemistry, molecular biology, microbiology, recombinant DNA and immunology, which are within the capabilities of a person of ordinary skill in the art. Such techniques are explained in the literature. See, for example, J. Sambrook, E. F. Fritsch, and T. Maniatis, 1989, *Molecular Cloning: A Laboratory Manual*, Second Edition, Books 1-3, Cold Spring Harbor Laboratory Press; Ausubel, F. M. et al. (1995 and periodic supplements; *Current Protocols in Molecular Biology*, ch. 9, 13, and 16, John Wiley & Sons, New York, N.Y.); B. Roe, J. Crabtree, and A. Kahn, 1996, *DNA Isolation and Sequencing: Essential Techniques*, John Wiley & Sons; J. M. Polak and James O'D. McGee, 1990, *In Situ Hybridization: Principles and Practice*; Oxford University Press; M. J. Gait (Editor), 1984, *Oli-* gonucleotide Synthesis: A Practical Approach, Irl Press; D. M. J. Lilley and J. E. Dahlberg, 1992, Methods of Enzymology: DNA Structure Part A: Synthesis and Physical Analysis of DNA Methods in Enzymology, Academic Press; Using Antibodies: A Laboratory Manual: Portable Protocol NO. I by Edward Harlow, David Lane, Ed Harlow (1999, Cold Spring Harbor Laboratory Press, ISBN 0-87969-544-7); Antibodies: A Laboratory Manual by Ed Harlow (Editor), David Lane (Editor) (1988, Cold Spring Harbor Laboratory Press, ISBN 0-87969-314-2), 1855, Lars-Inge Larsson *"Immunocytochemistry: Theory and Practice"*, CRC Press inc., Baca Raton, Fla., 1988, ISBN 0-8493-6078-1, John D. Pound (ed); *"Immunochemical Protocols, vol 80"*, in the series: "Methods in Molecular Biology", Humana Press, Totowa, N.J., 1998, ISBN 0-89603-493-3, Handbook of Drug Screening, edited by Ramakrishna Seethala, Prabhavathi B. Fernandes (2001, New York, N.Y., Marcel Dekker, ISBN 0-8247-0562-9); and Lab Ref: A Handbook of Recipes, Reagents, and Other Reference Tools for Use at the Bench, Edited Jane Roskams and Linda Rodgers, 2002, Cold Spring Harbor Laboratory, ISBN 0-87969-630-3. Each of these general texts is herein incorporated by reference.

As used herein, "PS4" shall refer to family members related to or having sequence or functional homology with *Pseudomonas saccharophila* non-maltogenic exoamylase, such as the exoamlyase having the amino acid sequence set forth in SEQ ID NO:1 or SEQ ID NO:5 or *Pseudomonas stutzeri* non-maltogenic exoamylase, such as a polypeptide having the amino acid sequence set forth in SEQ ID NO: 7 or SEQ ID NO 11. Other family members are set forth in Table 1.

Position numbering with respect to PS4 variants derived from *Pseudomonas saccharophila* exoamylase shall be with respect SEQ ID NO: 1:

```
  1  DQAGKSPAGV RYHGGDEIIL QGFHWNVVRE APNDWYNILR QQASTIAADG FSAIWMPVPW
 61  RDFSSWTDG  G KSGGGEGYFW HDFNKNGRYG SDAQLRQAAG ALGGAGVKVL YDVVPNHMNR
121  GYPDKEINLP AGQGFWRNDC A DPGNYPNDC DDGDRFIGGE SDLNTGHPQI YGMFRDELAN
181  LRSGYGAGGF RFDFVRGYAP ERVDSWMSDS ADSSFCVGEL WKG PSEYPSW DWRNTASWQQ
241  IIKDWSDRAK CPVFDFALKE RMQNGSVA DW KHGLNGNPDP RWREVAVTFV DNHDTGYSPG
301  QNGGQHHWAL QDG LIRQAYA YILTSPGTPV VYWSHMYDWG YGDFIRQLIQ VRRTAGVRAD
361  SAISFHSGYS GLVATVSGSQ QTLVVALNSD LANPGQVASG SFSEAVNASN GQVRVWRSGS
421  GDGGGNDGGE GGLVNVNFRC DNGVTQMGDS VYAVGNVSQL GNWSPASAVR LTDTSSYPTW
481  KGSIALPDGQ NVEWKCLIRN EADATLVRQW QSGGNNQVQA AAGASTSGSF
```

The reference sequence is derived from the *Pseudomonas saccharophilia* sequence having SWISS-PROT accession number P22963, but without the signal sequence MSHILRAAVLAAVLLPFPALA.

The numbering system, even though it may use a specific sequence as a base reference point, is also applicable to all relevant homologous sequences. For example, the position numbering may be applied to homologous sequences from other *Pseudomonas* species, or homologous sequences from other bacteria. Preferably, such homologous have 60% or greater homology, for example 70% or more, 80% or more, 90% or more or 95% or more homology, with the reference sequence SEQ ID NO: 1. Sequence homology between proteins may be ascertained using well-known alignment programs and hybridisation techniques described herein.

Position numbering with respect to PS4 variants derived from a *Pseudomonas stutzeri* shall be with respect to SEQ ID NO: 7:

```
  1 DQAGKSPNAV RYHGGDEIIL QGFHWNVVRE APNDWYNILR QQAATIAADG FSAIWMPVPW
 61 RDFSSWSDGS KSGGGEGYFW HDFNKNGRYG SDAQLRQAAS ALGGAGVKVL YDVVPNHMNR
121 GYPDKEINLP AGQGFWRNDC ADPGNYPNDC DDGDRFIGGD ADLNTGHPQV YGMFRDEFTN
181 LRSQYGAGGF RFDFVRGYAP ERVNSWMTDS ADNSFCVGEL WKGPSEYPNW DWRNTASWQQ
241 IIKDWSDRAK CPVFDFALKE RMQNGSIADW KHGLNGNPDP RWREVAVTFV DNHDTGYSPG
301 QNGGQHHWAL QDGLIRQAYA YILTSPGTPV VYWSHMYDWG YGDFIRQLIQ VRRAAGVRAD
```

-continued

```
361 SAISFHSGYS GLVATVSGSQ QTLVVALNSD LGNPGQVASG SFSEAVNASN GQVRVWRSGT

421 GSGGGEPGAL VSVSFRCDNG ATQMGDSVYA VGNVSQLGNW SPAAALRLTD TSGYPTWKGS

481 IALPAGQNEE WKCLIRNEAN ATQVRQWQGG ANNSLTPSEG ATTVGRL
```

As used herein, "PS4 variant nucleic acids" shall refer to nucleic acids encoding PS4 polypeptides which are variants of PS4 family members.

As used herein, "PS4 variant polypeptides" or "PS4 variant" shall refer to polypeptides which are variants of PS4 family members.

As used herein, "parent enzymes," "parent sequence," "parent polypeptide" and "parent polypeptides" shall mean enzymes and polypeptides on which the PS4 variant polypeptides are based. The parent enzyme may be a precursor enzyme (i.e. the enzyme that is actually mutated) or it may be prepared de novo. The parent enzyme may be a wild type enzyme.

As used herein, "variant" shall mean a molecule being derivable from a parent molecule. Variants shall include polypeptides as well as nucleic acids. Variants shall include substitutions, insertions, transversions and inversions, among other things, at one or more locations. Variants shall also include truncations. Variants shall include homologous and functional derivatives of parent molecules. Variants shall include sequences that are complementary to sequences that are capable of hybridising to the nucleotide sequences presented herein. For example, a variant sequence is complementary to sequences capable of hybridising under stringent conditions (e.g. 50° C. and 0.2×SSC {1×SSC=0.15 M NaCl, 0.015 M $Na_3$citrate pH 7.0}) to the nucleotide sequences presented herein. More preferably, the term variant encompasses sequences that are complementary to sequences that are capable of hybridising under high stringent conditions (e.g. 65° C. and 0.1×SSC {1×SSC=0.15 M NaCl, 0.015 M $Na_3$citrate pH 7.0}) to the nucleotide sequences presented herein.

As used herein, "precursor" shall mean an enzyme used to produce a modified enzyme. The precursor may be an enzyme modified by mutagenesis. Likewise, the precursor may be a wild type enzyme, a variant wild type enzyme or an already mutated enzyme.

As used herein, "functional equivalent" shall mean in relation to a parent enzyme shall mean a molecule having similar or identical function to a parent molecule. The parent molecule may be a *Pseudomonas saccharophila* non-maltogenic exoamylase or a *Pseudomonas stutzeri* non-maltogenic exoamylase or a polypeptide obtained from other sources. The functionally equivalent enzyme may have a different amino acid sequence but will have non-maltogenic exoamylase activity. Examples of assays to determine functionality are described herein and are known to one skilled in the art.

As used herein, "isolated" shall mean that the sequence is at least substantially free from at least one other component which the sequence is naturally associated and found in nature.

As used herein, "purified" shall mean that the sequence is in a relatively pure state—e.g. at least about 90% pure, or at least about 95% pure or at least about 98% pure.

As used herein, "amylase" shall mean an enzyme that is, among other things, capable of catalysing the degradation of starch. Amylases are hydrolases which cleave the α-D-(1→4) O-glycosidic linkages in starch. Generally, α-amylases (E.C. 3.2.1.1, α-D-(1→4)-glucan glucanohydrolase) are defined as endo-acting enzymes cleaving α-D-(1→4) O-glycosidic linkages within the starch molecule in a random fashion. In contrast, the exo-acting amylolytic enzymes, such as β-amylases (E.C. 3.2.1.2, α-D-(14)-glucan maltohydrolase) and some product-specific amylases like maltogenic alpha-amylase (E.C. 3.2.1.133) cleave the starch molecule from the non-reducing end of the substrate. β-Amylases, α-glucosidases (E.C. 3.2.1.20, α-D-glucoside glucohydrolase), glucoamylase (E.C. 3.2.1.3, α-D-(1→4)-glucan glucohydrolase), and product-specific amylases can produce malto-oligosaccharides of a specific length from starch.

As used herein, "non-maltogenic exoamylase enzyme" shall mean an enzyme that does not initially degrade starch to substantial amounts of maltose. Assays for making such determinations are provided in herein.

As used herein, "linear malto-oligosaccharide" shall mean 2-20 units of α-D-glucopyranose linked by an α-(1→4) bond.

As used herein, "thermostable" relates to the ability of the enzyme to retain activity after exposure to elevated temperatures. The thermostability of an enzyme such as a non-maltogenic exoamylase is measured by its half-life. The half-life (t½) is the time in minutes during which half the enzyme activity is inactivated under defined conditions. The half-life value is calculated by measuring the residual amylase activity. Half-life assays are conducted as described in more detail in the Examples.

As used herein, "pH stable" relates to the ability of the enzyme to retain activity over a wide range of pHs. pH assays are conducted as described in the Examples.

As used herein, "exo-specific" relates to an improved, e.g., increased, "exo-specificity index" as compared an exo-specificity ratio of an unsubstituted exoamylase.

As used herein, "exo-specificity index" shall mean the ratio of the total amylase activity to the total endoamylase activity. Assays for measuring amylase and endoamylase activity are provided herein.

As used herein, "food" shall include both prepared food, as well as an ingredient for a food, such as flour.

As used herein, "food ingredient" shall include a formulation, which is or can be added to functional foods or foodstuffs and includes formulations used at low levels in a wide variety of products that require, for example, acidifying or emulsifying. The food ingredient may be in the form of a solution or as a solid—depending on the use and/or the mode of application and/or the mode of administration.

As used herein, "functional food" means food capable of providing not only a nutritional effect and/or a taste satisfaction, but is also capable of delivering a further beneficial effect to consumer.

As used herein, "amino acid sequence" is synonymous with the term "polypeptide" and/or the term "protein". In some instances, the term "amino acid sequence" is synonymous with the term "peptide". In some instances, the term "amino acid sequence" is synonymous with the term "enzyme".

As used herein, "peptoid form" shall refer to variant amino acid residues wherein the α-carbon substituent group is on the residue's nitrogen atom rather than the α-carbon. Processes for preparing peptides in the peptoid form are known in the art, for example Simon R J et al., *PNAS* (1992) 89(20), 9367-9371 and Horwell D. C., *Trends Biotechnol.* (1995) 13(4), 132-134.

As used herein, "nucleotide sequence" or "nucleic acid sequence" refers to an oligonucleotide sequence or polynucleotide sequence, and variant, homologues, fragments and derivatives thereof (such as portions thereof). The nucleotide sequence may be of genomic or synthetic or recombinant origin, which may be double-stranded or single-stranded whether representing the sense or anti-sense strand. As used herein, the term nucleotide sequence includes genomic DNA, cDNA, synthetic DNA and RNA. Preferably it means DNA, more preferably cDNA sequence coding for a PS4 variant polypeptide.

As used herein, "starch" shall mean starch per se or a component thereof, especially amylopectin. The term "starch medium" means any suitable medium comprising starch. The term "starch product" means any product that contains or is based on or is derived from starch. Preferably, the starch product contains or is based on or is derived from starch obtained from wheat flour.

As used herein, "flour" shall mean finely-ground meal of wheat or other grain. For example, flour may be obtained from wheat per se and not from another grain. Wheat flour may refer mean to wheat flour, per se, as well as to wheat flour when present in a medium, such as dough.

As used herein, "baked farinaceous bread product" shall mean any baked product based on dough obtainable by mixing flour, water and a leavening agent under dough forming conditions. Further components can be added to the dough mixture.

As used herein, "homologue" and "homology" shall mean an entity having a certain degree of identity with the subject amino acid sequences and the subject nucleotide sequences. A homologous sequence is taken to include an amino acid sequence at least 75, 80, 85 or 90% identical, preferably at least 95, 96, 97, 98 or 99% identical to the subject sequence. Typically, homologues will comprise the same active sites as the subject amino acid sequence.

As used herein, "hybridisation" shall include the process by which a strand of nucleic acid joins with a complementary strand through base pairing as well as the process of amplification as carried out in polymerase chain reaction (PCR) technologies. The PS4 nucleic acid may exist as single- or double-stranded DNA or RNA, an RNA/DNA heteroduplex or an RNA/DNA copolymer.

As used herein, "copolymer" refers to a single nucleic acid strand that comprises both ribonucleotides and deoxyribonucleotides. The PS4 nucleic acid may even be codon optimised to further increase expression.

As used herein, "synthetic" shall refer to that which is produced by in vitro chemical or enzymatic synthesis. It includes but is not limited to PS4 nucleic acids made with optimal codon usage for host organisms such as the methylotrophic yeasts *Pichia* and *Hansenula*.

As used herein, "transformed cell" shall include cells that have been transformed by use of recombinant DNA techniques. Transformation typically occurs by insertion of one or more nucleotide sequences into a cell. The inserted nucleotide sequence may be a heterologous nucleotide sequence (i.e. is a sequence that is not natural to the cell that is to be transformed. In addition, or in the alternative, the inserted nucleotide sequence may be an homologous nucleotide sequence, i.e. is a sequence that is natural to the cell that is to be transformed)—so that the cell receives one or more extra copies of a nucleotide sequence already present in it.

As used herein, "operably linked" shall mean that the components described are in a relationship permitting them to function in their intended manner. A regulatory sequence operably linked to a coding sequence is ligated in such a way that expression of the coding sequence is achieved under condition compatible with the control sequences.

As used herein, "biologically active" shall refer to a sequence having a similar structural function (but not necessarily to the same degree), and/or similar regulatory function (but not necessarily to the same degree) and/or similar biochemical function (but not necessarily to the same degree) of the naturally occurring sequence.

I. Detailed Description of the Polypeptides of the Invention

In a first aspect, the invention provides a polypeptide comprising a PS4 variant, the PS4 variant being derivable from a parent polypeptide. The parent enzyme may preferably be a non-maltogenic exoamylase, preferably bacterial non-maltogenic exoamylase enzyme. The parent enzyme may preferably be a polypeptide which exhibits non-maltogenic exoamylase activity.

The parent enzyme may be a *Pseudomonas saccharophila* non-maltogenic exoamylase, such as the exoamlyase set forth in SEQ ID NO:1 or SEQ ID NO:5. The parent enzyme may be a *Pseudomonas stutzeri* non-maltogenic exoamylase, such as a polypeptide having set forth in SEQ ID NO: 7 or SEQ ID NO11. Other members of the PS4 family may be used as parent enzymes as set forth in Table 1 below. Preferably, PS4 family members will generally be similar to, homologous to or functionally equivalent to the exoamlyases set forth in SEQ ID NO:1, SEQ ID NO:5, SEQ ID NO:7 or SEQ ID NO:11, and may be identified by standard methods, such as hybridisation screening of a suitable library using probes, or by genome sequence analysis. Methods of identification are set forth below.

TABLE 1

Parent Sequences (PS4 family members). The sequences depicted differ from the *Pseudomonas saccharophila* sequence at the positions shown on the top row of the table, by including substitutions consisting of the amino acid residues set out. For example, pS4cc1-S161A is a variant of wild type *Pseudomonas* non-maltogenic exo-amylase, and thus can be used as a parent enzyme. Furthermore, non-maltogenic exoamylases from other strains of *Pseudomonas* spp, such as ATCC17686, may also be used as a parent polypeptide. The PS4 variant polypeptide residues may be inserted into any of the parent sequences to generate the variant PS4 polypeptide sequences

| Homolog/variant | $t_?$ | G5PNP/ blG7PNP | G5PNP/ blG5PNP | G5PNP/ Phadebas | 67 | 68 | 157 | 160 | 161 | 166 | 170 | 178 | 184 | 198 | 204 |
|---|---|---|---|---|---|---|---|---|---|---|---|---|---|---|---|
| ATCC17686 | 0.6 | 1.5 | 1.5 | 49 | S | E | V | D | A | S | V | F | Q | F | N |
| GICC#320 | 0.6 | 1.5 | 1.4 | 39 | T | D | I | D | A | S | V | L | Q | Y | D |

TABLE 1-continued

Parent Sequences (PS4 family members). The sequences depicted differ from the *Pseudomonas saccharophila* sequence at the positions shown on the top row of the table, by including substitutions consisting of the amino acid residues set out. For example, pS4

G134R, A141P, I157L, G223A, H307L, S334P, D343E, N33Y, and G121D;

G134R, A141P, I157L, G223A, H307L, S334P, D343E, and N33Y;

G134R, A141P, I157L, G223A, H307L, S334P, D343E, N33Y, D34N, K71R, L178F, A179T, G87S, G121D, S214N, and T375A;

G134R, A141P, I157L, G223A, H307L, S334P, D343E, N33Y, D34N, K71R, L178F, A179T, G121D, Y171S, G188A, and N138D;

G134R, A141P, I157L, G223A, H307L, S334P, D343E, N33Y, D34N, K71R, L178F, A179T, and G121D;

G87S, G121D, G134R, A141P, I157L, G223A, H307L, S334P, D343E, N33Y, D34N, K71R, L178F, and A179T;

G87S, G121D, G134R, A141P, I157L, G223A, H307L, S334P, D343E, N33Y, D34N, K71R, L178F, A179T, and G188A;

G134R, A141P, I157L, G223A, H307L, S334P, K71R, L178F, and A179T;

G134R, A141P, I157L, G223A, H307L, S334P, L178F, and A179T;

G134R, A141P, I157L, G223A, H307L, S334P, N33Y, D34N, L178F, and A179T;

G134R, A141P, I157L, G223A, H307L, S334P, L178F, A179T, G87S, and G121D;

G134R, A141P, I157L, G223A, H307L, S334P, L178F, A179T, and G121D;

G134R, A141P, I157L, G223A, H307L, S334P, N33Y, D34N, K71R, L178F, A179T, and G121D;

G87S G121D G134R, A141P I157L G223A H307L S334P D343E N33Y D34N K71R L178F A179T;

G87S G121D, G134R, A141P I157L G223A H307L S334P K71R L178F A179T G134R, A141P I157L G223A H307L S334P D343E N33Y D34N K71R L178F A179T G121D; and

G134R, A141P I157L G223A H307L S334P K71R L178F A179T G121D.

In another embodiment, the at least one substitution comprises a combination selected from the group of:

A141P, I157L, G223A, H307L and S334P;

G121D, G134R, A141P, I157L, G223A, H307L and S334;

G87S, G121D, G134R, A141P, I157L, G223A, H307L and S334P;

G134R, A141P, I157L, L178F, A179T, G223A, H307L and S334P;

G87S, G121D, G134R, A141P, I157L, L178F, A179T, G223A, H307L and S334P;

G121D, G134R, A141P, I157L, L178F, A179T, G223A, H307L and S334P;

N33Y, D34N, G134R, A141P, I157L, L178F, A179T, G223A, H307L and S334P;

N33Y, D34N, G121D, G134R, A141P, I157L, L178F, A179T, G223A, H307L and S334P; and N33Y, D34N, G87S, G121D, G134R, A141P, I157L, L178F, A179T, G223A, H307L and S334P.

In another embodiment, the exo amylase comprising at least one substitution comprises a combination selected from the following:

N33Y, D34N, G134R, A141P, I157L, L178F, A179T, G223A, H307L and S334P;

N33Y, D34N, G87S, G121D, G134R, A141P, I157L, L178F, A179T, G223A, H307L and S334P; and N33Y, D34N, G87S, G121D, G134R, A141P, I157L, L178F, A179T, G223A, H307L and S334P.

In another embodiment, the exoamylase comprising at least one substitution comprises a combination selected from the following:

G87S, V113I, G134R, A141P, I157L, Y198F, G223A, V290I, H307L, S334P, and D343E;

113F, A141P, I157L, Y198F, G223A, V290I, H307L, S334P, and D343E;

A99V, V113I, A141P, I157L, Y198F, G223A, V290I, H307L, S334P, and D343E;

V113I, I157L, Y198F, G223A, V290I, H307L, S334P, and D343E V113I, G134R, A141P, I157L, Y198F, G223A, V290I, H307L, S334P, and D343E;

A141P, I157L, Y198F, G223A, V290I, H307L, S334P, and D343E;

A199V, D343E, V113I, A141P, I157L, Y198F, G223A, V290I, H307L, and S334P;

V113I, A141P, I157L, Y198F, G223A, V290I, S334P, and D343E;

V113I, G121D, G134R, A141P, I157L, Y198F, G223A, V290I, H307L, S334P, and D343E;

V113I, G121D, G134R, A141P, I157L, Y198F, G223A, V290I, H307L, S334P, and D343E;

V113I, A141P, I157L, Y198F, G223A, V290I, H307L, S334P, and D343E;

V113I, A141P, Y198F, G223A, V290I, and H307L;

V113I, A141P, Y198F, G223A, V290I, S334P, and D343E;

V113I, A141P, Y198F, G223A, A268P, V290I, and S399P V113I, A141P, Y198F, G223A, V290I, and S399P;

V113I, A141P, Y198W, G223A, and V290I;

V113I, A141P, Y198F, G223A, and V290I;

Y198F, G223A, and V290I;

Y198W, G223A, and V290I;

V113I, A141P, I157L, Y198F, G223A, and V290I;

V1113M;

V113A;

V113I, G134R, A141P, I157L, Y198F, G223A, V290I, H307L, S334P, and D343E;

V113I, G134R, A141P, I157L, Y198F, G223A, V290I, H307L, I315V, S334P, and D343E;

D34N, V113I, G134R, A141P, I157L, Y198F, G223A, V290I, H307L, S334P, and D343E;

V113I, G134R, A141P, I157L, G188S, Y198F, G223A, V290I, H307L, S334P, and D343E;

K71R, V113I, G134R, A141P, I157L, L178L, Y198F, G223A, V290I, H307L, G313G, S334P, and D343E;

D34N, V113I, G134R, A141P, I157L, Y198F, G223A, V290I, H307L, G313G, S334P, and D343E;

V113I, G134R, A141P, I157L, A179V, Y198F, G223A, V290I, H307L, S334P, and D343E;

V113I, G134R, A141P, I157L, I170I, Y198F, G223A, V290I, H307L, G313G, S334P, and D343E V113I, G134R, A141P, I157L, A179V, Y198F, G223A, V290I, H307L, G313G, S334P, and D343E;

G87S, V113I, G134R, A141P, I157L, Y198F, G223A, V290I, H307L, S334P, and D343E;

V113I, G134R, A141P, I157L, Y198F, G223A, V290I, H307L, S334P, D343E, and A405E;

V113I, G134R, A141P, I157L, Y198F, G223A, V290I, H307L, S334P, D343E, and A405V;

A141P, I157L, Y198F, G223A, V290I, H307L, S334P, and D343E;

V113I, G134R, A141P, I157L, Y198L, G223A, V290I, H307L, S334P, and D343E;

V113I, G134R, A141P, I157L, Y198F, G223A, V290I, H307L, S334P, and D343E;

K71R, V113I, G134R, A141P, I157L, Y198F, G223A, V290I, H307L, S334P, and D343E;

K108R, V113I, G134R, A141P, I157L, Y198F, G223A, V290I, H307L, S334P, and D343E;

D34G, V113I, G134R, A141P, I157L, Y198F, G223A, V290I, H307L, S334P, and D343E;

G4D, V113I, A141P, I157L, Y198F, G223A, V290I, H307L, S334P, and D343E;

A141P, G134R, G223A, H307L, 157L, V113I, V290I, Y198F, and G188A; In preferred embodiments, the PS4 variant is an amino acid sequence comprising either SEQ ID NO:2; SEQ ID NO:3; SEQ ID NO:4; SEQ ID NO 4a, SEQ ID NO 4b, SEQ ID NO 4c, SEQ ID NO:8, SEQ ID NO:9 or SEQ ID NO:10.

The PS4 variant polypeptide may comprise one or more mutations in addition to those set out above. Other mutations, such as deletions, insertions, substitutions, transversions, transitions and inversions, at one or more other locations, may also be included. Likewise, the polypeptide may be missing at least one of the substitutions set forth above.

The PS4 variant may also comprise a conservative substitution that may occur as a like-for-like substitution (e.g., basic for basic, acidic for acidic, polar for polar etc.) Non-conservative substitution may also occur i.e. from one class of residue to another or alternatively involving the inclusion of unnatural amino acids such as ornithine (hereinafter referred to as Z), diaminobutyric acid ornithine (hereinafter referred to as B), norleucine ornithine (hereinafter referred to as O), pyriylalanine, thienylalanine, naphthylalanine and phenylglycine.

The sequences may also have deletions, insertions or substitutions of amino acid residues which produce a silent change and result in a functionally equivalent substance. Deliberate amino acid substitutions may be made on the basis of similarity in amino acid properties (such as polarity, charge, solubility, hydrophobicity, hydrophilicity, and/or the amphipathic nature of the residues) and it is therefore useful to group amino acids together as in functional groups. Amino acids can be grouped together based on the properties of their side chain alone. However it is more useful to include mutation data as well. The sets of amino acids thus derived are likely to be conserved for structural reasons. These sets can be described in the form of a Venn diagram (Livingstone C. D. and Barton G. J. (1993) "Protein sequence alignments: a strategy for the hierarchical analysis of residue conservation" *Comput. Appl Biosci.* 9: 745-756)(Taylor W. R. (1986) "The classification of amino acid conservation" *J. Theor. Biol.* 119; 205-218). Conservative substitutions may be made, for example according to the table below which describes a generally accepted Venn diagram grouping of amino acids.

| Set | | Sub-set | |
|---|---|---|---|
| Hydrophobic | F W Y H K M I L V A G C | Aromatic | F W Y H |
| | | Aliphatic | I L V |
| Polar | W Y H K R E D C S T N Q | Charged | H K R E D |
| | | Positively charged | H K R |
| | | Negatively charged | E D |
| Small | V C A G S P T N D | Tiny | A G S |

Variant amino acid sequences may also include suitable spacer groups inserted between any two amino acid residues of the sequence including alkyl groups such as methyl, ethyl or propyl groups in addition to amino acid spacers such as glycine or β-alanine residues. A further form of variation involves the presence of one or more amino acid residues in peptoid form.

The PS4 variant may also comprise a homologous sequence. A homologous sequence comprises a nucleotide sequence at least 75, 80, 85 or 90% identical, preferably at least 95, 96, 97, 98 or 99% identical to a nucleotide sequence encoding a PS4 variant. Typically, the homologues will comprise the same sequences that code for the active sites as the subject sequence.

Homology comparisons can be conducted by eye, or more usually, with the aid of readily available sequence comparison programs. These commercially available computer programs can calculate % homology between two or more sequences. % homology may be calculated over contiguous sequences, i.e. one sequence is aligned with the other sequence and each amino acid in one sequence is directly compared with the corresponding amino acid in the other sequence one residue at a time. This is called an "ungapped" alignment. Typically, such ungapped alignments are performed only over a relatively short number of residues.

Although this is a very simple and consistent method, it fails to take into consideration that, for example, in an otherwise identical pair of sequences, one insertion or deletion will cause following amino acid residues to be put out of alignment, thus potentially resulting in a large reduction in % homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local homology.

However, these more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, it is preferred to use the default values when using such software for sequence comparisons. For example when using the GCG Wisconsin Bestfit package the default gap penalty for amino acid sequences is −12 for a gap and −4 for each extension.

Calculation of maximum % homology therefore firstly requires the production of an optimal alignment, taking into consideration gap penalties. A suitable computer program for carrying out such an alignment is the GCG Wisconsin Bestfit package (Devereux et al 1984 Nuc. Acids Research 12 p387). Examples of other software than can perform sequence comparisons include, but are not limited to, the BLAST package (see Ausubel et al., 1999 Short Protocols in Molecular Biology, 4$^{th}$ Ed—Chapter 18), FASTA (Altschul et al., 1990 J. Mol. Biol. 403-410) and the GENEWORKS suite of comparison tools. Both BLAST and FASTA are available for offline and online searching (see Ausubel et al., 1999, Short Protocols in Molecular Biology, pages 7-58 to 7-60). However, for some applications, it is preferred to use the GCG Bestfit program. BLAST 2 Sequences is also available for comparing protein and nucleotide sequence (see FEMS Microbiol Lett 1999 174(2): 247-50; FEMS Microbiol Lett 1999 177(1): 187-8 and tatianagncbi.nlm.nih.gov).

Although the final % homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table if supplied (see user manual for further details). For some applications, it is preferred to use the public default values for the GCG package, or in the case of other software, the default matrix, such as BLOSUM62.

Alternatively, percentage homologies may be calculated using the multiple alignment feature in DNASIS™ (Hitachi Software), based on an algorithm, analogous to CLUSTAL (Higgins D G & Sharp P M (1988), Gene 73(1), 237-244).

Once the software has produced an optimal alignment, it is possible to calculate % homology, preferably % sequence identity. The software typically does this as part of the sequence comparison and generates a numerical result.

Preferred embodiments also include functional equivalents. The PS4 variant polypeptides described in this document are derived from, or are variants of, polypeptides which preferably exhibit non-maltogenic exoamylase activity. Preferably, these parent enzymes are non-maltogenic exoamylases themselves. The PS4 variant polypeptides themselves in preferred embodiments also exhibit non-maltogenic exoamylase activity.

The PS4 variants described here will preferably have exospecificity, for example measured by exo-specificity indices, as described above, consistent with their being exoamylases. Moreover, they preferably have higher or increased exospecificity when compared to the parent enzymes or polypeptides from which they are derived. Thus, for example, the PS4 variant polypeptides may have 10%, 20%, 30%, 40%, 50%, 60%, 70%, 80%, 90%, 100%, 200% or higher exospecificity index when compared to their parent polypeptides, preferably under identical conditions. They may have 1.5× or higher, 2× or higher, 5× or higher, 10× or higher, 50× or higher, 100× or higher, when compared to their parent polypeptides, preferably under identical conditions.

In preferred embodiments, the functional equivalents will have sequence homology to at least one of the PS4 family members. Functional equivalents will have sequence homology to either of the *Pseudomonas saccharophila* and *Pseudomonas stutzeri* non-maltogenic exoamylases mentioned above, preferably both. The functional equivalent may also have sequence homology with any of the sequences set out as SEQ ID NOs: 1 to 12, preferably SEQ ID NO: 1 or SEQ ID NO: 7 or both. Sequence homology between such sequences is preferably at least 60%, preferably 65% or more, preferably 75% or more, preferably 80% or more, preferably 85% or more, preferably 90% or more, preferably 95% or more.

In other embodiments, the functional equivalents will be capable of specifically hybridising to any of the sequences set out above. Methods of determining whether one sequence is capable of hybridising to another are known in the art, and are for example, described in Sambrook et al (supra) and Ausubel, F. M. et al. (supra). In highly preferred embodiments, the functional equivalents will be capable of hybridising under stringent conditions, e.g. 65° C. and 0.1×SSC {1×SSC=0.15 M NaCl, 0.015 MNa$_3$Citrate pH 7.0}.

The amino acid sequence may be prepared/isolated from a suitable source, or it may be made synthetically or it may be prepared by use of recombinant DNA techniques. Several methods are described below.

2. Detailed Description of the Nucleic Acids of the Invention

In a second aspect, the invention provides a nucleic acid, the nucleic acid encoding a polypeptide comprising a PS4 variant being derivable from a parent polypeptide, as set forth above.

One skilled in the art will be aware of the relationship between nucleic acid sequence and polypeptide sequence, in particular, the genetic code and the degeneracy of this code, and will be able to construct such PS4 nucleic acids without difficulty. For example, one skilled in the art will be aware that for each amino acid substitution in the PS4 variant polypeptide sequence there may be one or more codons which encode the substitute amino acid. Accordingly, it will be evident that, depending on the degeneracy of the genetic code with respect to that particular amino acid residue, one or more PS4 nucleic acid sequences may be generated corresponding to that PS4 variant polypeptide sequence. Thus, for example, a PS4 variant nucleic acid sequence may be derivable from a parent sequence encoding a polypeptide having, wherein the PS4 variant nucleic acid encodes amino acid substitutions at the following positions: G134, A141, I157, G223, H307, S334, N33 and D34, together with one or both of L178 and A179.

Mutations in amino acid sequence and nucleic acid sequence may be made by any of a number of techniques, as known in the art. In particularly preferred embodiments, the mutations are introduced into parent sequences by means of PCR (polymerase chain reaction) using appropriate primers, as illustrated in the Examples.

The parent enzymes may be modified at the amino acid level or the nucleic acid level to generate the PS4 variant sequences described herein. Therefore, a preferred embodiment of this aspect of the invention provides for the generation of PS4 variant polypeptides by introducing one or more corresponding codon changes in the nucleotide sequence encoding a non-maltogenic exoamylase polypeptide.

It will be appreciated that the above codon changes can be made in any PS4 family nucleic acid sequence. For example, sequence changes can be made to a *Pseudomonas saccharophila* or a *Pseudomonas stutzeri* non-maltogenic exoamylase nucleic acid sequence (e.g., X16732, SEQ ID NO: 6 or M24516, SEQ ID NO: 12).

The parent enzyme may comprise the "complete" enzyme, i.e., in its entire length as it occurs in nature (or as mutated), or it may comprise a truncated form thereof. The PS4 variant derived from such may accordingly be so truncated, or be "full-length". The truncation may be at the N-terminal end or the C-terminal end. The parent enzyme or PS4 variant may lack one or more portions, such as sub-sequences, signal sequences, domains or moieties, whether active or not. For example, the parent enzyme or the PS4 variant polypeptide may lack a signal sequence, as described above. Alternatively, or in addition, the parent enzyme or the PS4 variant may lack one or more catalytic or binding domains.

In highly preferred embodiments, the parent enzyme or PS4 variant may lack one or more of the domains present in non-maltogenic exoamylases, such as the starch binding domain. For example, the PS4 polypeptides may have only sequence up to position 429, relative to the numbering of a *Pseudomonas saccharophila* non-maltogenic exoamylase shown as SEQ ID NO: 1. For example, this is the case for the PS4 variants pSac-d34, pSac-D20, pSac-D14 or the other variants described in the Examples.

Typically, the PS4 variant nucleotide sequence is prepared using recombinant DNA techniques. However, in an alternative embodiment, the nucleotide sequence could be synthesised, in whole or in part, using chemical methods well known in the art (see Caruthers M H et al., (1980) *Nuc Acids Res Symp Ser* 215-23 and Horn T et al., (1980) *Nuc Acids Res Symp Ser* 225-232).

A nucleotide sequence encoding either an enzyme which has the specific properties as defined herein or an enzyme which is suitable for modification, such as a parent enzyme, may be identified and/or isolated and/or purified from any cell or organism producing said enzyme. Various methods are well known within the art for the identification and/or isolation and/or purification of nucleotide sequences. By way of example, PCR amplification techniques to prepare more of a sequence may be used once a suitable sequence has been identified and/or isolated and/or purified.

By way of further example, a genomic DNA and/or cDNA library may be constructed using chromosomal DNA or messenger RNA from the organism producing the enzyme. If the amino acid sequence of the enzyme or a part of the amino acid sequence of the enzyme is known, labelled oligonucleotide probes may be synthesised and used to identify enzyme-encoding clones from the genomic library prepared from the organism. Alternatively, a labelled oligonucleotide probe containing sequences homologous to another known enzyme gene could be used to identify enzyme-encoding clones. In the latter case, hybridisation and washing conditions of lower stringency are used.

Alternatively, enzyme-encoding clones could be identified by inserting fragments of genomic DNA into an expression vector, such as a plasmid, transforming enzyme-negative bacteria with the resulting genomic DNA library and then plating the transformed bacteria onto agar plates containing a substrate for enzyme (e.g., maltose), thereby allowing clones expressing the enzyme to be identified.

In a yet further alternative, the nucleotide sequence encoding the enzyme may be prepared synthetically by established standard methods, e.g. the phosphoroamidite method described by Beucage S. L. et al., (1981) *Tetrahedron Letters* 22, p 1859-1869 or the method described by Matthes et al., (1984) *EMBO J.* 3, p 801-805. In the phosphoroamidite method, oligonucleotides are synthesised, e.g. in an automatic DNA synthesiser, purified, annealed, ligated and cloned in appropriate vectors.

The nucleotide sequence may be of mixed genomic and synthetic origin, mixed synthetic and cDNA origin or mixed genomic and cDNA origin, prepared by ligating fragments of synthetic, genomic or cDNA origin in accordance with standard techniques. Each ligated fragment corresponds to various parts of the entire nucleotide sequence. The DNA sequence may also be prepared by polymerase chain reaction (PCR) using specific primers, for instance as described in U.S. Pat. No. 4,683,202 or in Saiki R K et al., (*Science* (1988) 239, pp 487-491).

The nucleotide sequences described here, and suitable for use in the methods and compositions described here may include within them synthetic or modified nucleotides. A number of different types of modification to oligonucleotides are known in the art. These include methylphosphonate and phosphorothioate backbones and/or the addition of acridine or polylysine chains at the 3' and/or 5' ends of the molecule. For the purposes of this document, it is to be understood that the nucleotide sequences described herein may be modified by any method available in the art. Such modifications may be carried out in order to enhance the in vivo activity or life span of nucleotide sequences.

A preferred embodiment of the invention provides for nucleotide sequences and the use of nucleotide sequences that are complementary to the sequences presented herein, or any derivative, fragment or derivative thereof. If the sequence is complementary to a fragment thereof then that sequence can be used as a probe to identify similar coding sequences in other organisms etc.

Polynucleotides which are not 100% homologous to the PS4 variant sequences may be obtained in a number of ways. Other variants of the sequences described herein may be obtained for example by probing DNA libraries made from a range of individuals, for example individuals from different populations. In addition, other homologues may be obtained and such homologues and fragments thereof in general will be capable of selectively hybridising to the sequences shown in the sequence listing herein. Such sequences may be obtained by probing cDNA libraries made from or genomic DNA libraries from other species and probing such libraries with probes comprising all or part of any one of the sequences in the attached sequence listings under conditions of medium to high stringency. Similar considerations apply to obtaining species homologues and allelic variants of the polypeptide or nucleotide sequences described here.

Variants and strain/species homologues may also be obtained using degenerate PCR which will use primers designed to target sequences within the variants and homologues encoding conserved amino acid sequences. The primers used in degenerate PCR will contain one or more degenerate positions and will be used at stringency conditions lower than those used for cloning sequences with single sequence primers against known sequences. Conserved sequences can be predicted, for example, by aligning the amino acid sequences from several variants/homologues. Sequence alignments can be performed using computer software known in the art as described herein.

Alternatively, such polynucleotides may be obtained by site directed mutagenesis of characterised sequences. This may be useful where, for example, silent codon sequence changes are required to optimise codon preferences for a particular host cell in which the polynucleotide sequences are being expressed. Other sequence changes may be desired in order to introduce restriction enzyme recognition sites, or to alter the property or function of the polypeptides encoded by the polynucleotides.

The polynucleotides may be used to produce a primer, e.g. a PCR primer, a primer for an alternative amplification reaction, a probe e.g. labelled with a revealing label by conventional means using radioactive or non-radioactive labels or the polynucleotides may be cloned into vectors. Such primers, probes and other fragments will be at least 15, preferably at least 20, for example at least 25, 30 or 40 nucleotides in length, and are also encompassed by the term polynucleotides.

Polynucleotides such as DNA polynucleotides and probes may be produced recombinantly, synthetically or by any means available to those of skill in the art. They may also be cloned by standard techniques. In general, primers will be produced by synthetic means, involving a stepwise manufacture of the desired nucleic acid sequence one nucleotide at a time. Techniques for accomplishing this using automated techniques are readily available in the art.

Longer polynucleotides will generally be produced using recombinant means, for example using a PCR (polymerase chain reaction) cloning techniques. The primers may be designed to contain suitable restriction enzyme recognition sites so that the amplified DNA can be cloned into a suitable cloning vector. Preferably, the variant sequences are at least as biologically active as the sequences presented herein.

A preferred embodiment of the invention includes sequences that are complementary to the nucleic acid sequences of PS4 variants or sequences that are capable of hybridising either to the nucleotide sequences of PS4 variants (including complementary sequences of those presented herein), as well as nucleotide sequences that are complementary to sequences that can hybridise to the nucleotide sequences of PS4 variants (including complementary sequences of those presented herein). A preferred embodiment provides polynucleotide sequences that are capable of hybridising to the nucleotide sequences presented herein under conditions of intermediate to maximal stringency.

A preferred embodiment includes nucleotide sequences that can hybridise to the nucleotide sequence of a PS4 variant nucleic acid, or the complement thereof, under stringent conditions (e.g. 50° C. and 0.2×SSC). More preferably, the nucleotide sequences can hybridise to the nucleotide sequence of a PS4 variant, or the complement thereof, under high stringent conditions (e.g. 65° C. and 0.1×SSC).

Once an enzyme-encoding nucleotide sequence has been isolated, or a putative enzyme-encoding nucleotide sequence has been identified, it may be desirable to mutate the sequence in order to prepare an enzyme. Accordingly, a PS4 variant sequence may be prepared from a parent sequence. Mutations may be introduced using synthetic oligonucleotides. These oligonucleotides contain nucleotide sequences flanking the desired mutation sites. A suitable method is disclosed in Morinaga et al., (*Biotechnology* (1984) 2, p646-649). Another method of introducing mutations into enzyme-encoding nucleotide sequences is described in Nelson and Long (*Analytical Biochemistry* (1989), 180, p 147-151). A further method is described in Sarkar and Sommer (*Biotechniques* (1990), 8, p404-407—"The megaprimer method of site directed mutagenesis").

In a preferred embodiment, the sequence for use in the methods and compositions described here is a recombinant sequence—i.e. a sequence that has been prepared using recombinant DNA techniques. Such techniques are explained, for example, in the literature, for example, J. Sambrook, E. F. Fritsch, and T. Maniatis, 1989, *Molecular Cloning: A Laboratory Manual*, Second Edition, Books 1-3, Cold Spring Harbor Laboratory Press.

3. Detailed Description of Compositions of the Invention

A third aspect of the invention provides for compositions comprising polypeptides which are variants of polypeptides having non-maltogenic exoamylase activity, as well as uses of such variant polypeptides and the compositions. The compositions include the polypeptide variants together with another component.

A preferred embodiment of the invention comprises a PS4 variant polypeptide, optionally together with a further ingredient or a further enzyme or both. In addition to the PS4 variant polypeptides, one or more enzymes may be added, for example added to the food, dough preparation, foodstuff or starch composition. Further enzymes that may be added to the dough include oxidoreductases, hydrolases, such as lipases (e.g., lipase (EC 3.1.1) capable of hydrolysing carboxylic ester bonds to release carboxylate or such as triacylglycerol lipase (EC 3.1.1.3), galactolipase (EC 3.1.1.26), phospholipase A1 (EC 3.1.1.32), phospholipase A2 (EC 3.1.1.4) and lipoprotein lipase A2 (EC 3.1.1.34)) and esterases as well as glycosidases like α-amylase, pullulanase and xylanase. Oxidoreductases, such as maltose oxidising enzyme, a glucose oxidase (EC 1.1.3.4), carbohydrate oxidase, glycerol oxidase, pyranose oxidase, galactose oxidase (EC 1.1.3.10) and hexose oxidase (EC 1.1.3.5) can be used for dough strengthening and control of volume of the baked products and, xylanases and other hemicellulases may be added to improve dough handling properties, crumb softness and bread volume. Lipases are useful as dough strengtheners and crumb softeners and α-amylases and other amylolytic enzymes may be incorporated into the dough to control bread volume and further reduce crumb firmness. Further enzymes that may be used can be selected from the group consisting of a cellulase, a hemicellulase, a starch degrading enzyme, a protease, a lipoxygenase. In a preferred embodiment, a PS4 variant polypeptide may be combined with amylases, in particular, maltogenic amylases. Maltogenic alpha-amylase (glucan 1,4-a-maltohydrolase, E.C. 3.2.1.133) is able to hydrolyze amylose and amylopectin to maltose in the alpha-configuration.

A maltogenic alpha-amylase from *Bacillus* (EP 120 693) is commercially available (Novo Nordisk A/S, Denmark) and is widely used in the baking industry as an anti-staling agent due to its ability to reduce retrogradation of starch. (see, for example, WO 91/04669). The maltogenic alpha-amylase shares several characteristics with cyclodextrin glucanotransferases (CGTases), including sequence homology (Henrissat B, Bairoch A; Biochem. J., 316, 695-696 (1996)) and formation of transglycosylation products (Christophersen, C., et al., 0.1997, Starch, vol. 50, No. 1, 39-45). A preferred embodiment includes combinations comprising PS4 variant polypeptides together with the alpha-amylase or any of its variants. Such combinations are useful for food production such as baking. Variants, homologues, and mutants of variants disclosed in U.S. Pat. No. 6,162,628, the entire disclosure of which is hereby incorporated by reference, may be used in combination with the PS4 variant polypeptides described herein. In particular, any of the polypeptides described in that document, specifically variants of SEQ ID NO:1 of U.S. Pat. No. 6,162,628 at any one or more positions corresponding to Q13, I16, D17, N26, N28, P29, A30, S32, Y33, G34, L35, K40, M45, P73, V74, D76 N77, D79, N86, R95, N99, I100, H103, Q119, N120, N131, S141, T142, A148, N152, A163, H169, N171, G172, I174, N176, N187, F188, A192, Q201, $N_2O_3$, H220, N234, G236, Q247, K249, D261, N266, L268, R272, N275, N276, V279, N280, V281, D285, N287, F297, Q299, $N_3O_5$, K316, N320, L321, N327, A341, N342, A348, Q365, N371, N375, M378, G397, A381, F389, N401, A403, K425, N436, S442, N454, N468, N4745 S479, A483, A486, V487, S493, T494, S495, A496, S497, A498, Q500, N507, I510, N513, K520, Q526, A555, A564, S573, N575, Q581, S583, F586, K589, N595, G618, N621, Q624, A629, F636, K645, N664 and/or T681 may be used.

The further enzyme can be added together with any dough ingredient including the flour, water or optional other ingredients or additives or the dough improving composition. The further enzyme can be added before or after the flour, water and optionally other ingredients and additives or the dough improving composition. The further enzyme may conveniently be a liquid preparation or in the form of a dry composition.

Some enzymes of the dough improving composition are capable of interacting with each other under the dough conditions to an extent where the effect on improvement of the rheological and/or machineability properties of a flour dough and/or the quality of the product made from dough by the enzymes is not only additive, but the effect is synergistic. In relation to improvement of the product made from dough (finished product), it may be found that the combination results in a substantial synergistic effect in respect to crumb structure. Also, with respect to the specific volume of baked product a synergistic effect may be found.

4. Vectors, Cells and Methods of Expressing a PS4 Polypeptide

A fourth aspect provides vectors comprising a PS4 variant polypeptide, cells comprising a PS4 variant polypeptide and methods of expressing a PS4 variant polypeptide.

The nucleotide sequence for use in the methods and compositions described herein may be incorporated into a recombinant replicable vector. The vector may be used to replicate and express the nucleotide sequence, in enzyme form, in and/or from a compatible host cell. Expression may be controlled using control sequences, eg. regulatory sequences. The enzyme produced by a host recombinant cell by expression of the nucleotide sequence may be secreted or may be contained intracellularly depending on the sequence and/or the vector used. The coding sequences may be designed with signal sequences which direct secretion of the substance coding sequences through a particular prokaryotic or eukaryotic cell membrane.

Polynucleotides can be incorporated into a recombinant replicable vector. The vector may be used to replicate the nucleic acid in a compatible host cell. The vector comprising the polynucleotide sequence may be transformed into a suitable host cell. Suitable hosts may include bacterial, yeast, insect and fungal cells.

PS4 variant polypeptides and polynucleotides may be expressed by introducing a polynucleotide into a replicable vector, introducing the vector into a compatible host cell and growing the host cell under conditions which bring about replication of the vector. The vector may be recovered from the host cell.

The PS4 nucleic acid may be operatively linked to transcriptional and translational regulatory elements active in a host cell of interest. The PS4 nucleic acid may also encode a fusion protein comprising signal sequences such as, for example, those derived from the glucoamylase gene from *Schwanniomyces occidentalis*, α-factor mating type gene from *Saccharomyces cerevisiae* and the TAKA-amylase from *Aspergillus oryzae*. Alternatively, the PS4 nucleic acid may encode a fusion protein comprising a membrane binding domain.

The PS4 variant may be expressed at the desired levels in a host organism using an expression vector. An expression vector comprising a PS4 nucleic acid can be any vector capable of expressing the gene encoding the PS4 nucleic acid in the selected host organism, and the choice of vector will depend on the host cell into which it is to be introduced. Thus, the vector can be an autonomously replicating vector, i.e. a vector that exists as an episomal entity, the replication of which is independent of chromosomal replication, such as, for example, a plasmid, a bacteriophage or an episomal element, a minichromosome or an artificial chromosome. Alternatively, the vector may be one which, when introduced into a host cell, is integrated into the host cell genome and replicated together with the chromosome.

The expression vector typically includes the components of a cloning vector, such as, for example, an element that permits autonomous replication of the vector in the selected host organism and one or more phenotypically detectable markers for selection purposes. The expression vector normally comprises control nucleotide sequences encoding a promoter, operator, ribosome binding site, translation initiation signal and optionally, a repressor gene or one or more activator genes. Additionally, the expression vector may comprise a sequence coding for an amino acid sequence capable of targeting the PS4 variant to a host cell organelle such as a peroxisome or to a particular host cell compartment. Such a targeting sequence includes but is not limited to the sequence SKL. For expression under the direction of control sequences, the nucleic acid sequence the PS4 variant is operably linked to the control sequences in proper manner with respect to expression.

Preferably, a polynucleotide in a vector is operably linked to a control sequence that is capable of providing for the expression of the coding sequence by the host cell, i.e. the vector is an expression vector. The control sequences may be modified, for example by the addition of further transcriptional regulatory elements to make the level of transcription directed by the control sequences more responsive to transcriptional modulators. The control sequences may in particular comprise promoters.

In the vector, the nucleic acid sequence encoding for the variant PS4 polypeptide is operably combined with a suitable promoter sequence. The promoter can be any DNA sequence having transcription activity in the host organism of choice and can be derived from genes that are homologous or heterologous to the host organism. Examples of suitable promoters for directing the transcription of the modified nucleotide sequence, such as PS4 nucleic acids, in a bacterial host include the promoter of the lac operon of *E. coli*, the *Streptomyces coelicolor* agarase gene dagA promoters, the promoters of the *Bacillus licheniformis* α-amylase gene (amyL), the aprE promoter of *Bacillus subtilis*, the promoters of the *Bacillus stearothermophilus* maltogenic amylase gene (amyM), the promoters of the *Bacillus amyloliquefaciens* α-amylase gene (amyQ), the promoters of the *Bacillus subtilis* xylA and xylB genes and a promoter derived from a *Lactococcus* sp.-derived promoter including the P170 promoter. When the gene encoding the PS4 variant polypeptide is expressed in a bacterial species such as *E. coli*, a suitable promoter can be selected, for example, from a bacteriophage promoter including a T7 promoter and a phage lambda promoter. For transcription in a fungal species, examples of useful promoters are those derived from the genes encoding the, *Aspergillus oryzae* TAKA amylase, *Rhizomucor miehei* aspartic proteinase, *Aspergillus niger* neutral α-amylase, *A. niger* acid stable α-amylase, *A. niger* glucoamylase, *Rhizomucor miehei* lipase, *Aspergillus oryzae* alkaline protease, *Aspergillus oryzae* triose phosphate isomerase or *Aspergillus nidulans* acetamidase. Examples of suitable promoters for the expression in a yeast species include but are not limited to the Gal 1 and Gal 10 promoters of *Saccharomyces cerevisiae* and the *Pichia pastoris* AOX1 or AOX2 promoters.

Examples of suitable bacterial host organisms are gram positive bacterial species such as Bacillaceae including *Bacillus subtilis, Bacillus licheniformis, Bacillus lentus, Bacillus brevis, Bacillus stearothermophilus, Bacillus alkalophilus, Bacillus amyloliquefaciens, Bacillus coagulans, Bacillus lautus, Bacillus megaterium* and *Bacillus thuringiensis, Streptomyces* species such as Streptomyces murinus, lactic acid bacterial species including *Lactococcus* spp. such as *Lactococcus lactis, Lactobacillus* spp. including *Lactobacillus reuteri, Leuconostoc* spp., *Pediococcus* spp. and *Streptococcus* spp. Alternatively, strains of a gram-negative bacterial species belonging to Enterobacteriaceae including *E. coli*, or to Pseudomonadaceae can be selected as the host organism. A suitable yeast host organism can be selected from the biotechnologically relevant yeasts species such as but not limited to yeast species such as *Pichia* sp., *Hansenula* sp or *Kluyveromyces, Yarrowinia* species or a species of *Saccharomyces* including *Saccharomyces cerevisiae* or a species belonging to Schizosaccharomyce such as, for example, *S. Pombe* species. Preferably a strain of the methylotrophic yeast species *Pichia pastoris* is used as the host organism. Preferably the host organism is a *Hansenula* species. Suitable host organisms among filamentous fungi include species of *Aspergillus*, e.g. *Aspergillus niger, Aspergillus oryzae, Aspergillus tubigensis, Aspergillus awamori* or *Aspergillus nidulans*. Alternatively, strains of a *Fusarium* species, e.g. *Fusarium oxysporum* or of a *Rhizomucor* species such as *Rhizomucor miehei* can be used as the host organism. Other suitable strains include *Thermomyces* and *Mucor* species.

Host cells comprising polynucleotides may be used to express polypeptides, such as variant PS4 polypeptides, fragments, homologues, variants or derivatives thereof. Host cells may be cultured under suitable conditions which allow expression of the proteins. Expression of the polypeptides may be constitutive such that they are continually produced, or inducible, requiring a stimulus to initiate expression. In the case of inducible expression, protein production can be initiated when required by, for example, addition of an inducer substance to the culture medium, for example dexamethasone or IPTG. Polypeptides can be extracted from host cells by a variety of techniques known in the art, including enzymatic, chemical and/or osmotic lysis and physical disruption. Polypeptides may also be produced recombinantly in an in vitro cell-free system, such as the TnT™ (Promega) rabbit reticulocyte system.

5. Use(s)

In the following description and examples, unless the context dictates otherwise, dosages of PS4 variant polypeptides are given in parts per million (micrograms per gram) of flour. For example, "1 D34" as used in Table 2 indicates 1 part per million of pSac-D34.

The PS4 substitution mutants described here may be used for any purpose for which the parent enzyme is suitable. In particular, they may be used in any application for which exo-maltotetraohydrolase is used. In highly preferred embodiments; they have the added advantage of higher thermostability, or higher exoamylase activity or higher pH stability, or any combination. Examples of suitable uses for the PS4 variant polypeptides and nucleic acids include food production, in particular baking, as well as production of foodstuffs; further examples are set out in detail below.

The following system is used to characterize polypeptides having non-maltogenic exoamylase activity which are suitable for use according to the methods and compositions described here. This system may for example be used to characterise the PS4 parent or variant polypeptides described here.

By way of initial background information, waxy maize amylopectin (obtainable as WAXILYS 200 from Roquette, France) is a starch with a very high amylopectin content (above 90%). 20 mg/ml of waxy maize starch is boiled for 3 min. in a buffer of 50 mM MES (2-(N-morpholino)ethanesulfonic acid), 2 mM calcium chloride, pH 6.0 and subsequently incubated at 50° C. and used within half an hour.

One unit of the non-maltogenic exoamylase is defined as the amount of enzyme which releases hydrolysis products equivalent to 1 µmol of reducing sugar per min. when incubated at 50 degrees C. in a test tube with 4 ml of 10 mg/ml waxy maize starch in 50 mM MES, 2 mM calcium chloride, pH 6.0 prepared as described above. Reducing sugars are measured using maltose as standard and using the dinitrosalicylic acid method of Bernfeld, *Methods Enzymol.*, (1954), 1, 149-158 or another method known in the art for quantifying reducing sugars.

The hydrolysis product pattern of the non-maltogenic exoamylase is determined by incubating 0.7 units of non-maltogenic exoamylase for 15 or 300 min. at 50° C. in a test tube with 4 ml of 10 mg/ml waxy maize starch in the buffer prepared as described above. The reaction is stopped by immersing the test tube for 3 min. in a boiling water bath.

The hydrolysis products are analyzed and quantified by anion exchange HPLC using a Dionex PA 100 column with sodium acetate, sodium hydroxide and water as eluents, with pulsed amperometric detection and with known linear maltooligosaccharides of from glucose to maltoheptaose as standards. The response factor used for maltooctaose to maltodecaose is the response factor found for maltoheptaose.

Preferably, the PS4 parent polypeptides (and the PS4 variant polypeptides) have non-maltogenic exoamylase activity such that if an amount of 0.7 units of said non-maltogenic exoamylase were to incubated for 15 minutes at a temperature of 50° C. at pH 6.0 in 4 ml of an aqueous solution of 10 mg preboiled waxy maize starch per ml buffered solution containing 50 mM 2-(N-morpholino)ethane sulfonic acid and 2 mM calcium chloride then the enzyme would yield hydrolysis product(s) that would consist of one or more linear maltooligosaccharides of from two to ten D-glucopyranosyl units and optionally glucose; such that at least 60% %, at least 70%, at least 80% and/or at least 85% by weight of the said hydrolysis products consisting of from two to ten D-glucopyranosyl units and optionally glucose would consist of linear maltooligosaccharides of from three to ten D-glucopyranosyl units, preferably of linear maltooligosaccharides consisting of from four to eight D-glucopyranosyl units.

For ease of reference, and for the present purposes, the feature of incubating an amount of 0.7 units of the non-maltogenic exoamylase for 15 minutes at a temperature of 50° C. at pH 6.0 in 4 ml of an aqueous solution of 10 mg preboiled waxy maize starch per ml buffered solution containing 50 mM 2-(N-morpholino)ethane sulfonic acid and 2 mM calcium chloride, may be referred to as the "Waxy Maize Starch Incubation Test".

Thus, alternatively expressed, a preferred non-maltogenic exoamylase is characterised as having the ability in the waxy maize starch incubation test to yield hydrolysis product(s) that would consist of one or more linear malto-oligosaccharides of from two to ten D-glucopyranosyl units and optionally glucose; such that at least 60%, preferably at least 70%, more preferably at least 80% and most preferably at least 85% by weight of the said hydrolysis product(s) would consist of linear maltooligosaccharides of from three to ten D-glucopyranosyl units, preferably of linear maltooligosaccharides consisting of from four to eight D-glucopyranosyl units.

The hydrolysis products in the waxy maize starch incubation test include one or more linear malto-oligosaccharides of from two to ten D-glucopyranosyl units and optionally glucose. The hydrolysis products in the waxy maize starch incubation test may also include other hydrolytic products. Nevertheless, the % weight amounts of linear maltooligosaccharides of from three to ten D-glucopyranosyl units are based on the amount of the hydrolysis product that consists of one or more linear malto-oligosaccharides of from two to ten D-glucopyranosyl units and optionally glucose. In other words, the % weight amounts of linear maltooligosaccharides of from three to ten D-glucopyranosyl units are not based on the amount of hydrolysis products other than one or more linear malto-oligosaccharides of from two to ten D-glucopyranosyl units and glucose. The hydrolysis products can be analysed by any suitable means. For example, the hydrolysis products may be analysed by anion exchange HPLC using a Dionex PA 100 column with pulsed amperometric detection and with, for example, known linear maltooligosaccharides of from glucose to maltoheptaose as standards.

Preferably, the PS4 variants described here are active during baking and hydrolyse starch during and after the gelatinization of the starch granules which starts at temperatures of about 55° C. The more thermostable the non-maltogenic exoamylase is the longer time it can be active and thus the more antistaling effect it will provide. However, during baking above temperatures of about 85° C., enzyme inactivation can take place. If this happens, the non-maltogenic exoamylase may be gradually inactivated so that there is substantially no activity after the baking process in the final bread. Therefore preferentially the non-maltogenic exoamylases suitable for use as described have an optimum temperature above 50° C. and below 98° C.

Exo-specificity can usefully be measured by determining the ratio of total amylase activity to the total endoamylase activity. This ratio is referred to in this document as a "Exo-specificity index". In preferred embodiments, an enzyme is considered an exoamylase if it has a exo-specificity index of 20 or more, i.e., its total amylase activity (including exo-amylase activity) is 20 times or more greater than its endoamylase activity. In highly preferred embodiments, the exo-specificity index of exoamylases is 30 or more, 40 or more, 50 or more, 60 or more, 70 or more, 80 or more, 90 or more, or 100 or more. In highly preferred embodiments, the exo-specificity index is 150 or more, 200 or more, 300 or more, or 400 or more.

The total amylase activity and the endoamylase activity may be measured by any means known in the art. For example, the total amylase activity may be measured by assaying the total number of reducing ends released from a starch substrate. Alternatively, the use of a Betamyl assay is described in further detail in the Examples, and for convenience, amylase activity as assayed in the Examples is described in terms of "Betamyl Units" in the Tables and Figures.

Endoamylase activity may be assayed by use of a Phadebas Kit (Pharmacia and Upjohn). This makes use of a blue labelled crosslinked starch (labelled with an azo dye); only internal cuts in the starch molecule release label, while external cuts do not do so. Release of dye may be measured by spectrophotometry. Accordingly, the Phadebas Kit measures endoamylase activity, and for convenience, the results of such an assay (described in the Examples) are referred to in this document as "Phadebas units".

In a preferred embodiment, therefore, the exo-specificity index is expressed in terms of Betamyl Units/Phadebas Units.

Exo-specificity may also be assayed according to the methods described in the prior art, for example, in Publication Number WO99/50399. This measures exo-specificity by way of a ratio between the endoamylase activity to the exoamylase activity. Thus, in a preferred aspect, the PS4 variants described here will have less than 0.5 endoamylase units (EAU) per unit of exoamylase activity. Preferably the non-maltogenic exoamylases which are suitable for use according to the present invention have less than 0.05 EAU per unit of exoamylase activity and more preferably less than 0.01 EAU per unit of exoamylase activity.

The PS4 variant polypeptides, nucleic acids, host cells, expression vectors, etc, may be used in any application for which an amylase may be used. In particular, they may be used to substitute for any non-maltogenic exoamylase. They may be used to supplement amylase or non-maltogenic exoamylase activity, whether alone or in combination with other known amylases or non-maltogenic exoamylases.

The PS4 variant sequences described here may be used in various applications in the food industry—such as in bakery and drink products, they may also be used in other applications such as a pharmaceutical composition, or even in the chemical industry. In particular, the PS4 variant polypeptides and nucleic acids are useful for various industrial applications including baking (as disclosed in WO 99/50399) and flour standardisation (volume enhancement or improvement). They may be used to produce maltotetraose from starch and other substrates.

The PS4 variant polypeptides may be used to enhance the volume of bakery products such as bread. Thus, food products comprising or treated with PS4 variant polypeptides are expanded in volume when compared to products which have not been so treated, or treated with parent polypeptides. In other words, the food products have a larger volume of air per volume of food product. Alternatively, or in addition, the food products treated with PS4 variant polypeptides have a lower density, or weight (or mass) per volume ratio. In particularly preferred embodiments, the PS4 variant polypeptides are used to enhance the volume of bread. Volume enhancement or expansion is beneficial because it reduces the gumminess or starchiness of foods. Light foods are preferred by consumers, and the customer experience is enhanced. In preferred embodiments, the use of PS4 variant polypeptides enhances the volume by 10%, 20%, 30% 40%, 50% or more.

The PS4 variant polypeptides and nucleic acids described here may be used as—or in the preparation of—a food. In particular, they may be added to a food, i.e., as a food additive. In a preferred aspect, the food is for human consumption. The food may be in the form of a solution or as a solid—depending on the use and/or the mode of application and/or the mode of administration.

The PS4 variant polypeptides and nucleic acids may be used as a food ingredient. The PS4 variant polypeptides and nucleic acids disclosed here may be—or may be added to—food supplements. The PS4 variant polypeptides and nucleic acids disclosed here may be—or may be added to—functional foods.

The PS4 variant polypeptides may also be used in the manufacture of a food product or a foodstuff. Typical foodstuffs include dairy products, meat products, poultry products, fish products and dough products. The dough product may be any processed dough product, including fried, deep fried, roasted, baked, steamed and boiled doughs, such as steamed bread and rice cakes. In highly preferred embodiments, the food product is a bakery product.

Preferably, the foodstuff is a bakery product. Typical bakery (baked) products include bread—such as loaves, rolls, buns, pizza bases etc. pastry, pretzels, tortillas, cakes, cookies, biscuits, crackers etc.

The PS4 variant proteins are capable of retarding the staling of starch media, such as starch gels. The PS4 variant polypeptides are especially capable of retarding the detrimental retrogradation of starch.

Accordingly, the use of PS4 variant polypeptides as described here when added to the starch at any stage of its processing into a food product, e.g., before during or after baking into bread can retard or impede or slow down the retrogradation. Such use is described in further detail below.

For evaluation of the antistaling effect of the PS4 variant polypeptides having non-maltogenic exoamylase activity described here, the crumb firmness can be measured 1, 3 and 7 days after baking by means of an Instron 4301 Universal Food Texture Analyzer or similar equipment known in the art.

Another method used traditionally in the art and which is used to evaluate the effect on starch retrogradation of a PS4 variant polypeptide having non-maltogenic exoamylase activity is based on DSC (differential scanning calorimetry). Here, the melting enthalpy of retrograded amylopectin in bread crumb or crumb from a model system dough baked with or without enzymes (control) is measured. The DSC equipment applied in the described examples is a Mettler-Toledo DSC 820 run with a temperature gradient of 10° C. per min. from 20 to 95° C. For preparation of the samples 10-20 mg of crumb are weighed and transferred into Mettler-Toledo aluminium pans which then are hermetically sealed.

The model system doughs used in the described examples contain standard wheat flour and optimal amounts of water or buffer with or without the non-maltogenic PS4 variant exoamylase. They are mixed in a 10 or 50 g Brabender Farinograph for 6 or 7 min., respectively. Samples of the doughs are placed in glass test tubes (15*0.8 cm) with a lid. These test tubes are subjected to a baking process in a water bath starting with 30 min. incubation at 33° C. followed by heating from 33 to 95° C. with a gradient of 1.1° C. per min. and finally a 5 min. incubation at 95° C. Subsequently, the tubes are stored in a thermostat at 20° C. prior to DSC analysis.

In preferred embodiments, the PS4 variants described here have a reduced melting enthalpy, compared to the control. In highly preferred embodiments, the PS4 variants have a 10% or more reduced melting enthalpy. Preferably, they have a 20% or more, 30%, 40%, 50%, 60%, 70%, 80%, 90% or more reduced melting enthalpy when compared to the control.

TABLE 2

|  | DSC (J/g) |
| --- | --- |
| Control | 2.29 |
| 0.5 D34 | 1.91 |
| 1 D34 | 1.54 |
| 2 D34 | 1.14 |

The above Table 2 shows DSC values of model dough systems prepared with different doses of PSac-D34 after 7 days of storage. 0.5, 1 and 2 parts per million (or microgram per gram) of flour are tested.

PS4 variant polypeptides can be used in the preparation of food products, in particular, starch products. The method comprises forming the starch product by adding a non-maltogenic exoamylase enzyme such as a PS4 variant polypeptide, to a starch medium. If the starch medium is a dough, then the dough is prepared by mixing together flour, water, the non-maltogenic exoamylase which is a PS4 variant polypeptide and optionally other possible ingredients and additives.

A preferred flour is wheat flour or rye flour or mixtures of wheat and rye flour. However, dough comprising flour derived from other types of cereals such as for example from rice, maize, barley, and durra are also contemplated. Preferably, the starch product is a bakery product. More preferably, the starch product is a bread product. Even more preferably, the starch product is a baked farinaceous bread product.

Thus, if the starch product is a baked farinaceous bread product, then the process comprises mixing—in any suitable order—flour, water, and a leavening agent under dough forming conditions and further adding a PS4 variant polypeptide, optionally in the form of a premix. The leavening agent may be a chemical leavening agent such as sodium bicarbonate or any strain of *Saccharomyces cerevisiae* (Baker's Yeast).

The PS4 variant non-maltogenic exoamylase can be added together with any dough ingredient including the water or dough ingredient mixture or with any additive or additive mixture. The dough can be prepared by any conventional dough preparation method common in the baking industry or in any other industry making flour dough based products.

A preferred embodiment is a process for making a bread product comprising: (a) providing a starch medium; (b) adding to the starch medium a PS4 variant polypeptide as described in this document; and (c) applying heat to the starch medium during or after step (b) to produce a bread product. Another preferred embodiment is a process for making a bread product comprising adding to a starch medium a PS4 variant polypeptide as described.

The non-maltogenic exoamylase PS4 variant polypeptide can be added as a liquid preparation or as a dry pulverulent composition either comprising the enzyme as the sole active component or in admixture with one or more additional dough ingredients or dough additives.

Another preferred embodiment is the use of such a bread and dough improving compositions in baking. A further embodiment provides a baked product or dough obtained from the bread improving composition or dough improving composition. Another embodiment provides a baked product or dough obtained from the use of a bread improving composition or a dough improving composition.

A dough may be prepared by admixing flour, water, a dough improving composition comprising PS4 variant polypeptide (as described above) and optionally other ingredients and additives.

The dough improving composition can be added together with any dough ingredient including the flour, water or optional other ingredients or additives. The dough improving composition can be added before the flour or water or optional other ingredients and additives. The dough improving composition can be added after the flour or water, or optional other ingredients and additives. The dough can be prepared by any conventional dough preparation method common in the baking industry or in any other industry making flour dough based products.

The dough improving composition can be added as a liquid preparation or in the form of a dry powder composition either comprising the composition as the sole active component or in admixture with one or more other dough ingredients or additive.

The amount of the PS4 variant polypeptide non-maltogenic exoamylase that is added is normally in an amount which results in the presence in the finished dough of 50 to 100,000 units per kg of flour, preferably 100 to 50,000 units per kg of flour. Preferably, the amount is in the range of 200 to 20,000 units per kg of flour.

In the present context, 1 unit of the non-maltogenic exoamylase is defined as the amount of enzyme which releases hydrolysis products equivalent to 1 μmol of reducing sugar per min. when incubated at 50 degrees C. in a test tube with 4 ml of 10 mg/ml waxy maize starch in 50 mM MES, 2 mM calcium chloride, pH 6.0 as described hereinafter.

The dough as described here generally comprises wheat meal or wheat flour and/or other types of meal, flour or starch such as corn flour, corn starch, maize flour, rice flour, rye meal, rye flour, oat flour, oat meal, soy flour, sorghum meal, sorghum flour, potato meal, potato flour or potato starch. The dough may be fresh, frozen, or part-baked.

The dough may be a leavened dough or a dough to be subjected to leavening. The dough may be leavened in various ways, such as by adding chemical leavening agents, e.g., sodium bicarbonate or by adding a leaven (fermenting dough), but it is preferred to leaven the dough by adding a suitable yeast culture, such as a culture of *Saccharomyces cerevisiae* (baker's yeast), e.g. a commercially available strain of *S. cerevisiae*.

The dough may comprise fat such as granulated fat or shortening. The dough may further comprise a further emulsifier such as mono- or diglycerides, sugar esters of fatty acids, polyglycerol esters of fatty acids, lactic acid esters of monoglycerides, acetic acid esters of monoglycerides, polyoxethylene stearates, or lysolecithin.

Another embodiment is a pre-mix comprising flour together with the combination as described herein. The pre-mix may contain other dough-improving and/or bread-improving additives, e.g. any of the additives, including enzymes, mentioned herein.

In order to improve further the properties of the baked product and impart distinctive qualities to the baked product further dough ingredients and/or dough additives may be incorporated into the dough. Typically, such further added components may include dough ingredients such as salt, grains, fats and oils, sugar or sweetener, dietary fibres, protein sources such as milk powder, gluten soy or eggs and dough additives such as emulsifiers, other enzymes, hydrocolloids, flavouring agents, oxidising agents, minerals and vitamins.

The emulsifiers are useful as dough strengtheners and crumb softeners. As dough strengtheners, the emulsifiers can provide tolerance with regard to resting time and tolerance to shock during the proofing. Furthermore, dough strengtheners will improve the tolerance of a given dough to variations in the fermentation time. Most dough strengtheners also improve on the oven spring which means the increase in volume from the proofed to the baked goods. Lastly, dough strengtheners will emulsify any fats present in the recipe mixture.

Suitable emulsifiers include lecithin, polyoxyethylene stearat, mono- and diglycerides of edible fatty acids, acetic acid esters of mono- and diglycerides of edible fatty acids, lactic acid esters of mono- and diglycerides of edible fatty acids, citric acid esters of mono- and diglycerides of edible fatty acids, diacetyl tartaric acid esters of mono- and diglycerides of edible fatty acids, sucrose esters of edible fatty acids, sodium stearoyl-2-lactylate, and calcium stearoyl-2-lactylate.

The further dough additive or ingredient can be added together with any dough ingredient including the flour, water or optional other ingredients or additives, or the dough improving composition. The further dough additive or ingredient can be added before the flour, water, optional other ingredients and additives or the dough improving composition. The further dough additive or ingredient can be added after the flour, water, optional other ingredients and additives or the dough improving composition.

The further dough additive or ingredient may conveniently be a liquid preparation. However, the further dough additive or ingredient may be conveniently in the form of a dry composition.

Preferably the further dough additive or ingredient is at least 1% the weight of the flour component of dough. More preferably, the further dough additive or ingredient is at least 2%, preferably at least 3%, preferably at least 4%, preferably at least 5%, preferably at least 6%. If the additive is a fat, then typically the fat may be present in an amount of from 1 to 5%, typically 1 to 3%, more typically about 2%.

Other uses may also be found in attorney docket numbers 674510-2007 and GC806P, all of which are hereby incorporated by reference, including and drawings, references and Figures.

EXAMPLES

Example 1

Cloning of PS4

*Pseudomonas saccharophila* is grown overnight on LB media and chromosomal DNA is isolated by standard methods (Sambrook J, 1989). A 2190 bp fragment containing the PS4 open reading frame (Zhou et al., 1989) is amplified from *P. saccharophila* chromosomal DNA by PCR using the primers P1 and P2 (see Table 3). The resulting fragment is used as a template in a nested PCR with primers P3 and P4, amplifying the openreading frame of PS4 without its signal sequence and introducing a NcoI site at the 5' end of the gene and a BamHI site at the 3'end. Together with the NcoI site a codon for a N-terminal Methionine is introduced, allowing for intracellular expression of PS4. The 1605 bp fragment is cloned into pCRBLUNT TOPO (Invitrogen) and the integrity of the construct analysed by sequencing. The *E. coli Bacillus* shuttle vector pDP66K (Penninga et al., 1996) is modified to allow for expression of the PS4 under control: of the P32 promoter and the ctgase signal sequence. The resulting plasmid, pCSmta is transformed into *B. subtilis*.

A second expression construct is made in which the starch binding domain of PS4 is removed. In a PCR with primers P3 and P6 (Table 3) on pCSmta, a truncated version of the mta gene is generated. The full length mta gene in pCSmta is exchanged with the truncated version which resulted in the plasmid pCSmta-SBD.

Example 2

Site Directed Mutagenesis of PS4

Mutations are introduced into the mta gene by 2 methods. Either by a 2 step PCR based method, or by a Quick Exchange method (QE). For convenience the mta gene is split up in 3 parts; a PvuI-FspI fragment, a FspI-PstI fragment and a PstI-AspI fragment, further on referred to as fragment 1, 2 and 3 respectively.

In the 2 step PCR based method, mutations are introduced using Pfu DNA polymerase (Stratagene)., A first PCR is carried out with a mutagenesis primer (Table 4) for the coding strand plus a primer downstream on the lower strand (either 2R or 3R Table 3). The reaction product is used as a primer in a second PCR together with a primer upstream on the coding strand. The product of the last reaction is cloned into pCR-BLUNT topo (Invitrogen) and after sequencing the fragment is exchanged with the corresponding fragment in pCSmta.

Using the Quick Exchange method (Stratagene), mutations are introduced using two complementary primers in a PCR on a plasmid containing the mta gene, or part of the mta gene.

For this purpose a convenient set of plasmids is constructed, comprising of 3 SDM plasmids and 3 pCSΔ plasmids. The SDM plasmids each bear 1 of the fragments of the mta gene as mentioned above, in which the desired mutation is introduced by QE. After verification by sequencing, the fragments are cloned into the corresponding recipient pCSΔ plasmid. The pCSΔ plasmids are inactive derivatives from pCSmta. Activity is restored by cloning the corresponding fragment from the SDM plasmid, enabling easy screening.

TABLE 3

Primers used in cloning the mta gene, and standard primers used in construction of site directed mutants with the 2 step PCR method.

| Primer | Primer sequence | Introduced site |
|--------|-----------------|-----------------|
| P1 | 5'-ATG ACG AGG TCC TTG TTT TTC | |
| P2 | 5'-CGC TAG TCG TCC ATG TCG | |

TABLE 3-continued

Primers used in cloning the mta gene, and standard primers used in construction of site directed mutants with the 2 step PCR method.

| Primer | Primer sequence | Introduced site |
|---|---|---|
| P3 | 5'-GCC ATG GAT CAG GCC GGC AAG AGC CCG | NcoI |
| P4 | 5'-TGG ATC CTC AGA ACG AGC CGC TGG T | BamHI |
| P6 | 5'-GAA TTC AGC CGC CGT CAT TCC CGC C | EcoRI |
| 2L | 5'-AGA TTT ACG GCA TGT TTC GC | |
| 2R | 5'-TAG CCG CTA TGG AAG CTG AT | |
| 3L | 5'-TGA CCT TCG TCG ACA ACC AC | |
| 3R | 5'-GAT AGC TGC TGG TGA CGG TC | |

TABLE 4

Primers used to introduce site directed mutations in mta

| Mutation | Oligo Sequence | Modification | Strand | Purpose |
|---|---|---|---|---|
| G134R | CTGCCGGCCGGCCAGcGCTTCTGGCG | | + | SDM |
| G134R- | cgccagaagcgctggccggccggcag | | − | SDM |
| I157L | GACGGTGACCGCTTCcTgGGCGGCGAGTCG | | + | SDM |
| I151L- | cgactcgccgcccaggaagcggtcaccgtc | | − | SDM |
| G223A | GGCGAGCTGTGGAAAgccCCTTCTGAATATCCG | | + | SDM |
| G223A- | cggatattcagaagggggctttccacagctcgcc | | − | SDM |
| H307L | gaacGGCGGCCAGCACctgTGGGCGCTGCAG | | + | SDM |
| H307L- | ctgcagcgcccacaggtgctggccgccgttc | | − | SDM |
| S334P, D343E | GTACTGGccgCACATGTACGACTGGGGCTACGGC gaaTTCATC | | + | SDM |
| S334P, D343E- | gatgaattcgccgtagccccagtcgtacatgtgc ggccagtac | | − | SDM |

TABLE 5

Features of the SDM and pCSΔ plasmids

| Plasmid | Features/construction |
|---|---|
| SDM1 | pBlueSK + 480 bp SalI-StuI fragment mta |
| SDM2 | pBlueSK + 572 bp SacII-PstI fragment mta |
| SDM3 | pBlueSK + 471 bp SalI-StuI fragment mta |
| pCSΔ1 | FseI site filled in with Klenow ----> frameshift in mta |
| pCSΔ2 | FspI-PstI fragment of mta replaced with 'junk-DNA' |
| pCSΔ3 | PstI-AspI fragment of mta replaced with 'junk-DNA' |

Example 3

Multi SDM

The PS4 variants were generated using a QuickChange® Multi Site Directed Mutagenesis Kit (Stratagene) according to the manufactures protocol with some modifications as described.

Step 1: Mutant Strand Synthesis Reaction (PCR)

Inoculate 3 ml. LB (22 g/l Lennox L Broth Base, Sigma)+ antibiotics (0.05 μg/ml kanamycin, Sigma) in a 10 ml Falcon tube Incubate o/n 37° C., ca. 200 rpm.

Spin down the cells by centrifugation (5000 rpm/5 min)

Poor off the medium

Prepare ds-DNA template using QIAGEN Plasmid Mini Purification Protocol

1. The mutant strand synthesis reaction for thermal cycling was prepared as follow:
PCR Mix:

| | |
|---|---|
| 2.5 μl | 10X QuickChange ® Multi reaction buffer |
| 0.75 μl | QuickSolution |
| X μl | Primers (primer length 28-35 bp → 10 pmol / primer length 24-27 bp → 7 pmol / primer length 20-23 bp → 5 pmol) |
| 1 μl | dNTP mix |
| X μl | ds-DNA template (200 ng) |
| 1 μl | QuickChange ® Multi enzyme blend (2.5 U/μl) (PfuTurbo ® DNA polymerase) |
| X μl | dH$_2$O (to a final volume of 25 μl) |

Mix all components by pipetting and briefly spin down the reaction mixtures.

2. Cycle the reactions using the following parameters:
35 cycles of denaturation (96° C./1 min)
 primer annealing (62.8° C./1 min)
 elongation (65° C./15 min)
 then hold at 4° C.
Preheat the lid of the PCR machine to 105° C. and the plate to 95° C. before the PCR tubes are placed in the machine (eppendorf thermal cycler).

Step 2: Dpn I Digestion

1. Add 2 µl Dpn I restriction enzyme (10 U/µl) to each amplification reaction, mix by pipetting and spin down mixture.
2. Incubate at 37° C. for ~3 hr.

Step 3: Transformation of XL10-Gold® Ultracompetent Cells

1. Thaw XL10-Gold cells on ice. Aliquot 45 µl cells per mutagenesis reaction to prechilled Falcon tubes.
2. Turn on the waterbath (42° C.) and place a tube with NZY+ broth in the bath to preheat.
3. Add 2 µl β-mercaptoethanol mix to each tube. Swirl and tap gently and incubate 10 min on ice, swirling every 2 min.
4. Add 1.5 µl Dpn I-treated DNA to each aliquot of cells, swirl to mix and incubate on ice for 30 min.
5. Heat-pulse the tubes in 42° C. waterbath for 30 s and place on ice for 2 min.
6. Add 0.5 ml preheated NZY+ broth to each tube and incubate at 37° C. for 1 hr with shaking at 225-250 rpm.
7. Plate 200 µl of each transformation reaction on LB plates (33.6 g/l Lennox L Agar, Sigma) containing 1% starch and 0.05 µg/ml kanamycin
8. Incubate the transformation plates at 37° C. overnight.

TABLE 6

Primer table for pPD77d14:

| Mutation | Oligo Sequence | Modification | Strand | Purpose |
| --- | --- | --- | --- | --- |
| N33Y, D34N | GCGAAGCGCCCTACAACTGGTACAAC | 5' phosphate | + | MSDM |
| K71R | CCGACGGCGGCAGGTCCGGCG | 5' phosphate | + | MSDM |
| G87S | CAAGAACAGCCGCTACGGCAGCGAC | 5' phosphate | + | MSDM |
| G121D | CACATGAACCGCGACTACCCGGACAAG | 5' phosphate | + | MSDM |
| G134R | CTGCCGGCCGGCCAGcGCTTCTGGCG | 5' phosphate | + | MSDM |
| A141P | CGCAACGACTGCGCCGACCCGGG | 5' phosphate | + | MSDM |
| I157L | GACGGTGACCGCTTCcTgGGCGGCGAGTCG | 5' phosphate | + | MSDM |
| L178F, A179T | CGCGACGAGTTTACCAACCTGCG | 5' phosphate | + | MSDM |
| G223A | GGCGAGCTGTGGAAAgccCCTTCTGAATATCCG | 5' phosphate | + | MSDM |
| H307L | gaacGGCGGCCAGCACctgTGGGCGCTGCAG | 5' phosphate | + | MSDM |
| S334P, D343E | GTACTGGccgCACATGTACGACTGGGGCTACGGC gaaTTCATC | 5' phosphate | + | MSDM |

TABLE 7

Primer table for pPD77d20:

| Mutation | Oligo Sequence | Modification | Strand | Purpose |
| --- | --- | --- | --- | --- |
| N33Y, D34N | GCGAAGCGCCCTACAACTGGTACAAC | 5' phosphate | + | MSDM |
| K71R | CCGACGGCGGCAGGTCCGGCG | 5' phosphate | + | MSDM |
| G121D | CACATGAACCGCGACTACCCGGACAAG | 5' phosphate | + | MSDM |
| G134R | CTGCCGGCCGGCCAGcGCTTCTGGCG | 5' phosphate | + | MSDM |
| A141P | CGCAACGACTGCGCCGACCCGGG | 5' phosphate | + | MSDM |
| I157L | GACGGTGACCGCTTCcTgGGCGGCGAGTCG | 5' phosphate | + | MSDM |
| L178F, A179T | CGCGACGAGTTTACCAACCTGCG | 5' phosphate | + | MSDM |
| G223A | GGCGAGCTGTGGAAAgccCCTTCTGAATATCCG | 5' phosphate | + | MSDM |
| H307L | gaacGGCGGCCAGCACctgTGGGCGCTGCAG | 5' phosphate | + | MSDM |

TABLE 7-continued

Primer table for pPD77d20:

| Mutation | Oligo Sequence | Modification | Strand | Purpose |
|---|---|---|---|---|
| S334P, D343E | GTACTGGccgCACATGTACGACTGGGGCTACGGC gaaTTCATC | 5' phosphate | + | MSDM |

TABLE 8

Primer table for pPD77d34:

| Mutation | Oligo Sequence | Modification | Strand | Purpose |
|---|---|---|---|---|
| N33Y, D34N | GCGAAGCGCCCTACAACTGGTACAAC | 5' phosphate | + | MSDM |
| G121D | CACATGAACCGCGACTACCCGGACAAG | 5' phosphate | + | MSDM |
| G134R | CTGGCGGCCGGCCAGcGCTTCTGGCG | 5' phosphate | + | MSDM |
| A141P | CGCAACGACTGCGCCGACCCGGG | 5' phosphate | + | MSDM |
| I157L | GACGGTGACCGCTTCcTgGGCGGCGAGTCG | 5' phosphate | + | MSDM |
| L178F, A179T | CGCGACGAGTTTACCAACCTGCG | 5' phosphate | + | MSDM |
| G223A | GGCGAGCTGTGGAAAgccCCTTCTGAATATCCG | 5' phosphate | + | MSDM |
| H307L | gaacGGCGGCCAGCACctgTGGGCGCTGCAG | 5' phosphate | + | MSDM |
| S334P | GTACTGGccgCACATGTACGACTGGGGCTACGGC | 5' phosphate | + | MSDM |

Vector System Based on pPD77

The vector system used for pPD77 is based on pCRblunt-TOPOII (invitrogen). The zeocin resistance cassette has been removed by pmlI, 393 bp fragment removed. The expression cassette from the pCC vector (P32-ssCGTase-PS4-tt) has then been inserted into the vector.

Ligation of PS4 Variant into pCCMini

The plasmid which contain the relevant mutations (created by MSDM) is cut with restriction enzyme Nco 1 and Hind III (Biolabs):
  3 μg plasmid DNA, X μl 10× buffer 2, 10 units Nco1, 20 units HindIII,
Incubation 2 h at 37° C.

Run digestion on a 1% agarose gel. Fragments sized 1293 bp (PS4 gene) is cut out of the gel and purified using Qiagen gel purification kit.

The vector pCCMini is then cut with restriction enzymes, Nco 1 and Hind III, and the digestion is then run on a 1% agarose gel. The fragment sized 3569 bp is cut out of the gel and purified using Qiagen gel purification kit.

Ligation: Use Rapid DNA ligation kit (Roche)
Use the double amount of insert compared to vector
  e.g. 2 μl insert (PS4 gene)
  1 μl vector
  5 μl T4 DNA ligation buffer 2×conc
  1 μl dH$_2$O
  1 μl T4 DNA ligase
Ligate 5 min/RT Transform the ligation into One Shot TOPO competent cells according to manufactures protocol (Invitrogen). Use 5 μl ligation pr. transformation.

Plate 50 μl transformations mix onto LB plates (33.6 g/l Lennox L Agar, Sigma) containing 1% starch and 0.05 μg/ml kanamycin. Vectors containing insert (PS4 variants) can be recognised by halo formation on the starch plates.

Example 4

Transformation into *Bacillus subtilis* (Protoplast Transformation)

*Bacillus subtilis* (strain DB104A; Smith et al. 1988; Gene 70, 351-361) is transformed with the mutated pCS-plasmids according to the following protocol.

A. Media for Protoplasting and Transformation

| 2 × SMM | per litre: 342 g sucrose (1 M); 4.72 g sodium maleate (0.04 M); 8:12 g MgCl$_2$,6H$_2$0 (0.04 M); pH 6.5 with concentrated NaOH. Distribute in 50-ml portions and autoclave for 10 min. |
|---|---|
| 4 × YT (½ NaCl) | 2 g Yeast extract + 3.2 g Tryptone + 0.5 g NaCl per 100 ml. |
| SMMP | mix equal volumes of 2 × SMM and 4 × YT. |
| PEG | 10 g polyethyleneglycol 6000 (BDH) or 8000 (Sigma) in 25 ml 1 × SMM (autoclave for 10 min.). |

B. Media for Plating/Regeneration

| agar | 4% Difco minimal agar. Autoclave for 15 min. |
|---|---|
| sodium succinate | 270 g/l (1 M), pH 7.3 with HCl. Autoclave for 15 min. |
| phosphate buffer | 3.5 g K$_2$HPO$_4$ + 1.5 g KH$_2$PO$_4$ per 100 ml. Autoclave for 15 min. |

-continued

| | |
|---|---|
| MgCl₂ | 20.3 g MgCl₂,6H₂O per 100 ml (1 M). |
| casamino acids | 5% (w/v) solution. Autoclave for 15 min. |
| yeast extract | 10 g per 100 ml, autoclave for 15 min. |
| glucose | 20% (w/v) solution. Autoclave for 10 min. |

DM3 regeneration medium: mix at 60 C (waterbath; 500-ml bottle):

250 ml sodium succinate 50 ml casamino acids 25 ml yeast extract 50 ml phosphate buffer 15 ml glucose 10 ml MgCl₂

100 ml molten agar

Add appropriate antibiotics: chloramphenicol and tetracycline, 5 ug/ml; erythromycin, 1 ug/ml. Selection on kanamycin is problematic in DM3 medium: concentrations of 250 ug/ml may be required.

C. Preparation of Protoplasts

1. Use detergent-free plastic or glassware throughout.

2. Inoculate 10 ml of 2×YT medium in a 100-ml flask from a single colony. Grow an overnight culture at 25-30 C in a shaker (200 rev/min).

3. Dilute the overnight culture 20 fold into 100 ml of fresh 2×YT medium (250 ml flask) and grow until $OD_{600}$=0.4-0.5 (approx. 2 h) at 37C in a shaker (200-250 rev/min).

4. Harvest the cells by centrifugation (9000 g, 20 min, 4 C).

5. Remove the supernatant with pipette and resuspend the cells in 5 ml of SMMP+5 mg lysozyme, sterile filtered.

6. Incubate at 37 C in a waterbath shaker (100 rev/min).

After 30 min and thereafter at 15 min intervals, examine 25 ul samples by microscopy. Continue incubation until 99% of the cells are protoplasted (globular appearance). Harvest the protoplasts by centrifugation (4000 g, 20 min, RT) and pipette off the supernatant. Resuspend the pellet gently in 1-2 ml of SMMP.

The protoplasts are now ready for use. (Portions (e.g. 0.15 ml) can be frozen at −80 C for future use (glycerol addition is not required). Although this may result in some reduction of transformability, 106 transformants per ug of DNA can be obtained with frozen protoplasts).

D. Transformation

1. Transfer 450 ul of PEG to a microtube.

2. Mix 1-10 ul of DNA (0.2 ug) with 150 ul of protoplasts and add the mixture to the microtube with PEG. Mix immediately, but gently.

3. Leave for 2 min at RT, and then add 1.5 ml of SMMP and mix.

4. Harvest protoplasts by microfuging (10 min, 13.000 rev/min (10-12.000 g)) and pour off the supernatant. Remove the remaining droplets with a tissue.

Add 300 ul of SMMP (do not vortex) and incubate for 60-90 min at 37 C in a waterbath shaker (100 rev/min) to allow for expression of antibiotic resistance markers. (The protoplasts become sufficiently resuspended through the shaking action of the waterbath.). Make appropriate dilutions in 1× SSM and plate 0.1 ml on DM3 plates.

Example 5

Fermentation of PS4 Variants in Shake Flasks

The shake flask substrate is prepared as follows:

| Ingredient | % (w/v) |
|---|---|
| Water | — |
| Yeast extract | 2 |
| Soy Flour | 2 |
| NaCl | 0.5 |
| Dipotassium phosphate | 0.5 |
| Antifoam agent | 0.05 |

The substrate is adjusted to pH 6.8 with 4N sulfuric acid or sodium hydroxide before autoclaving. 100 ml of substrate is placed in a 500 ml flask with one baffle and autoclaved for 30 minutes. Subsequently, 6 ml of sterile dextrose syrup is added. The dextrose syrup is prepared by mixing one volume of 50% w/v dextrose with one volume of water followed by autoclaving for 20 minutes.

The shake flask are inoculated with the variants and incubated for 24 hours at 35° C./180 rpm in an incubator. After incubation cells are separate from broth by centrifugation (10.000×g in 10 minutes) and finally, the supernatant is made cell free by microfiltration at 0.2 μm. The cell free supernatant is used for assays and application tests.

Example 6

Amylase Assays

Betamyl Assay

One Betamyl unit is defined as activity degrading 0.0351 mmole per 1 min. of PNP-coupled maltopentaose so that 0.0351 mmole PNP per 1 min. can be released by excess a-glucosidase in the assay mix. The assay mix contains 50 ul 50 mM Na-citrate, 5 mM $CaCl_2$, pH 6.5 with 25 ul enzyme sample and 25 ul Betamyl substrate (Glc5-PNP and a-glucosidase) from Megazyme, Ireland (1 vial dissolved in 10 ml water). The assay mix is incubated for 30 min. at 40C and then stopped by adding 150 ul 4% Tris. Absorbance at 420 nm is measured using an ELISA-reader and the Betamyl activity is calculate based on Activity=A420*d in Betamyl units/ml of enzyme sample assayed.

Endo-Amylase Assay

The endo-amylase assay is identical to the Phadebas assay run according to manufacturer (Pharmacia & Upjohn Diagnostics AB).

Exo-Specificity

The ratio of exo-amylase activity to Phadebas activity was used to evaluate exo-specificity.

Specific Activity

For the PSac-D14, PSac-D20 and PSac-D34 variants we find an average specific activity of 10 Betamyl units per microgram of purified protein measured according to Bradford (1976; Anal. Biochem. 72, 248). This specific activity is used for based on activity to calculate the dosages used in the application trials.

Example 7

Half-Life Determination t½ is defined as the time (in minutes) during which half the enzyme activity is inactivated under defined heat conditions.

In order to determine the half-life of the enzyme, the sample is heated for 1-10 minutes at constant temperatures of 60° C. to 90° C. The half life is calculated based on the residual Betamyl assay.

Procedure: In an Eppendorf vial, 1000 µl buffer is preheated for at least 10 minutes at 60° C. or higher. The heat treatment of the sample is started addition of 100 µl of the sample to the preheated buffer under continuous mixing (800 rpm) of the Eppendorf vial in an heat incubator (Termomixer comfort from Eppendorf). After 0, 2, 4, 6, 8 and 9 minutes of incubation, the treatment is stopped by transferring 45 µl of the sample to. 1000 µl of the buffer equilibrated at 20° C. and incubating for one minute at 1500 rpm and at 20° C. The residual activity is measured with the Betamyl assay.

Calculation: Calculation of t½ is based on the slope of log10 (the base-10 logarithm) of the residual Betamyl activity versus the incubation time. t½ is calculated as Slope/0.301=t½.

Example 8

Results

TABLE 9

Biochemical properties of the PSac-variants compared to wild-type PSac-cc1

| Variant | T½-75 | T½-80 | Betamyl/phadebas | Mutations |
|---|---|---|---|---|
| Psac-cc1 | <0.5 | | 40 | None |
| Psac-D3 | 9.3 | 3 | 43 | G134R A141P I157L G223A H307L S334P D343E N33Y D34N K71R L178F A179T |
| Psac-D14 | 9.3 | 2.7 | 65 | G134R A141P I157L G223A H307L S334P D343E N33Y D34N K71R L178F A179T G121D |
| Psac-D20 | 7.1 | 2.7 | 86 | G87S G134R A141P I157L G223A H307L S334P D343E N33Y D34N K71R L178F A179T G121D |
| Psac-D34 | 8.4 | 2.9 | 100 | G134R A141P I157L G223A H307L S334P N33Y D34N L178F A179T G121D |

TABLE 10

| | | | | |
|---|---|---|---|---|
| pPD77 | 3.6 | 1.3 | 20 | G134R, A141P I157L G223A H307L S334P D343E |
| pPD77d1 | 10.3 | 4 | 20 | G134R, A141P I157L G223A H307L S334P D343E N33Y D34N K71R G158D L178F A179T |
| pPD77d2 | 4.2 | | 21 | G134R, A141P I157L G223A H307L S334P D343E G158D |
| pPD77d3 | 8.9 | 3.1 | 35 | G134R, A141P I157L G223A H307L S334P D343E N33Y D34N K71R L178F A179T |
| pPD77d5 | 10[1] | | 43 | G134R, A141P I157L G223A H307L S334P D343E N33Y D34N G158D |
| pPD77d6 | 4.2 | | 14 | G134R, A141P I157L G223A H307L S334P D343E N33Y D34N K71R G158D L178F A179T |
| pPD77d10 | 3.7 | | 61 | G134R, A141P I157L G223A H307L S334P D343E G121D |
| pPD77d11 | 2.8 | | 57 | G134R A141P I157L G223A H307L S334P D343E N33Y G121D |
| pPD77d12 | 3.8 | | 53 | G134R A141P I157L G223A H307L S334P D343E N33Y |

TABLE 11

| | | | | |
|---|---|---|---|---|
| pPD77d3 | 8.9 | 3.1 | 35 | G134R, A141P I157L G223A H307L S334P D343E N33Y D34N K71R L178F A179T |
| pPD77d14 | 9.3 | 2.8 | 66 | G134R, A141P I157L G223A H307L S334P D343E N33Y D34N K71R L178F A179T G87S G121D S214N T375A |
| pPD77d17 | 1.3 | 0.5 | 86 | G134R, A141P I157L G223A H307L S334P D343E N33Y D34N K71R L178F A179T G121D Y171S G188A N138D |
| pPD77d20 | 7.1 | 2.7 | 81 | G134R, A141P I157L G223A H307L S334P D343E N33Y D34N K71R L178F A179T G121D |

TABLE 12

| | | | | |
|---|---|---|---|---|
| pPD77d14 | 9.3 | 2.8 | 66 | G87S G121D G134R, A141P I157L G223A H307L S334P D343E N33Y D34N K71R L178F A179T |
| pPD77d25 | | 2.4 | 71 | G87S G121D G134R, A141P I157L G223A H307L S334P D343E N33Y D34N K71R L178F A179T G188A |
| pPD77d3 | 8.9 | 3.1 | 35 | G134R, A141P I157L G223A H307L S334P D343E N33Y D34N K71R L178F A179T |
| pPD77d31 | | 2.5 | 53 | G134R, A141P I157L G223A H307L S334P D343E N33Y D34N K71R L178F A179T Y33N N34D E343D |
| pPD77d32 | | 2.5 | 52 | G134R, A141P I157L G223A H307L S334P D343E N33Y D34N K71R L178F A179T Y33N N34D R71K G87S G121D E343D |
| pPD77d33 | 7.1 | 3.0 | 51 | G134R, A141P I157L G223A H307L S334P D343E N33Y D34N K71R L178F A179T R71K E343D |
| pPD77d34 | 8.4 | 2.9 | 67 | G134R, A141P I157L G223A H307L S334P D343E N33Y D34N K71R L178F A179T Y33N N34D R71K G87S G121D E343D |
| pPD77d38 | 7.9 | 2.5 | 77 | G134R, A141P I157L G223A H307L S334P D343E N33Y D34N K71R L178F A179T Y33N N34D R71K G121D E343D |
| pPD77d39 | 7.5 | 2.6 | 42 | G134R, A141P I157L G223A H307L S334P D343E N33Y D34N K71R L178F A179T E343D |
| pPD77d40 | 10.26 | 3.1 | 63 | G134R, A141P I157L G223A H307L S334P D343E N33Y D34N K71R L178F A179T G121D E343D |

TABLE 13

| | | | | |
|---|---|---|---|---|
| pPD77d14 | 9.3 | 2.8 | 66 | G87S G121D G134R, A141P I157L G223A H307L S334P D343E N33Y D34N K71R L178F A179T |
| pPD77d35 | | | 0 | G87S G121D G134R, A141P I157L G223A H307L S334P D343E N33Y D34N K71R L178F A179T Y33N N34D R71K E343D |

TABLE 13-continued

| | | | |
|---|---|---|---|
| pPD77d36 | 2.8 | 77 | G87S G121D G134R, A141P I157L G223A H307L S334P D343E N33Y D34N K71R L178F A179T Y33N N34D E343D |

TABLE 14

| | | | | |
|---|---|---|---|---|
| pPD77d20 | 7.1 | 2.7 | 81 | G134R, A141P I157L G223A H307L S334P D343E N33Y D34N K71R L178F A179T G121D |
| pPD77d37 | 7.8 | 2.9 | 78 | G134R, A141P I157L G223A H307L S334P D343E N33Y D34N K71R L178F A179T G121D Y33N N34D E343D |

TABLE 15

| Identifier | Activity (U/ml) | T½ (65B) | T½ (70B) | T½ (72B) | T½ (75B) | T½ (80B) | Mut_OverV |
|---|---|---|---|---|---|---|---|
| SSM53F6 | 123 | | | 7.5 | 4.2 | 0.7 | G87S, V113I, G134R, A141P, I157L, Y198F, G223A, V290I, H307L, S334P, D343E |
| MS18 | 101 | 11.9 | | | | | I113F, A141P, I157L, Y198F, G223A, V290I, H307L, S334P, D343E |
| MC033 | 172 | 12.9 | 4.2 | 2.6 | 1.0 | | A99V, V113I, A141P, I157L, Y198F, G223A, V290I, H307L, S334P, D343E |
| MC037 | 138 | | | | 0.1 | | V113I, I157L, Y198F, G223A, V290I, H307L, S334P, D343E |
| MC032 | 177 | 41.5 | 7.4 | 4.2 | 1.1 | | V113I, G134R, A141P, I157L, Y198F, G223A, V290I, H307L, S334P, D343E |
| MC031 | 282 | 18.6 | 4.7 | 4.8 | 1.3 | | A141P, I157L, Y198F, G223A, V290I, H307L, S334P, D343E |
| MC028 | 118 | 9.3 | 4.4 | 2.7 | | | A199V, D343E, V113I, A141P, I157L, Y198F, G223A, V290I, H307L, S334P |
| MC027 | 87 | 11.4 | 4.3 | 2.1 | 0.4 | | V113I, A141P, I157L, Y198F, G223A, V290I, S334P, D343E |
| MC045 | 73 | | | | 1.3 | | V113I, G121D, G134R, A141P, I157L, Y198F, G223A, V290I, H307L, S334P, D343E |
| MC021 | 41 | 4.9 | | | | | V113I, A141P, I157L, Y198F, G223A, V290I, H307L, S334P, D343E |
| MC051 | 86 | | 9.2 | 5.2 | 1.3 | | V113I, G121D, G134R, A141P, I157L, Y198F, G223A, V290I, H307L, S334P, D343E |
| MC023 | 170 | 8.1 | 4.6 | 2.9 | 1.0 | | V113I, A141P, I157L, Y198F, G223A, V290I, H307L, S334P, D343E |
| MC010 | 20 | | | | | | V113A, A141P, Y198W, G223A, V290I |
| MC020 | 141 | 3.7 | 0.8 | | | | V113I, A141P, Y198F, G223A, V290I, H307L |
| MC019 | 145 | 5.2 | 1.6 | | | | V113I, A141P, Y198F, G223A, V290I, S334P, D343E |
| MC018 | 73 | 3.3 | | | | | V113I, A141P, Y198F, G223A, A268P, V290I, S399P |
| MC013 | 104 | 2.9 | | | | | V113I, A141P, Y198F, G223A, V290I, S399P |
| MC011 | 50 | 7.5 | | | | | V113I, A141P, Y198W, G223A, V290I |
| MC008 | 276 | 3.5 | | | | | V113I, A141P, Y198F, G223A, V290I |
| MC005 | 20 | | | | | | V113L, A141P, Y198F, G223A, V290I |
| MC004 | 24 | | | | | | V113A, A141P, Y198F, G223A, V290I |
| MC002 | 213 | | | | | | Y198F, G223A, V290I |
| MC001 | 82 | 3.4 | | | | | Y198W, G223A, V290I |
| MC022 | 79 | 8.5 | 1.2 | | | | V113I, A141P, I157L, Y198F, G223A, V290I |
| MP11 | | | | | | | V290I |
| MP04 | 51 | | | | | | V290I |
| S298 | 90 | | | | 1.1 | | V113I, G134R, A141P, I157L, Y198F, G223A, V290I, H307L, S334P, D343E |
| S297 | 69 | | | | 1.6 | | V113I, G134R, A141P, I157L, Y198F, G223A, V290I, H307L, I315V, S334P, D343E |
| S294 | 121 | | | 5.7 | 2.1 | | D34N, V113I, G134R, A141P, I157L, Y198F, G223A, V290I, H307L, S334P, D343E |
| S263 | 81 | | | 5.3 | 2.1 | | V113I, G134R, A141P, I157L, G188S, Y198F, G223A, V290I, H307L, S334P, D343E |
| S260 | 58 | | | 5.8 | 1.8 | | D34N, V113I, G134R, A141P, I157L, Y198F, G223A, V290I, H307L, G313G, S334P, D343E |
| S259 | 106 | | | 5.9 | 1.8 | | V113I, G134R, A141P, I157L, Y198F, S214G, G223A, V290I, H307L, S334P, D343E |
| S290 | 141 | | | 5.5 | 1.5 | | V113I, G134R, A141P, I157L, A179V, Y198F, G223A, V290I, H307L, S334P, D343E |
| S286 | 150 | | 12.0 | 6.6 | 1.8 | | V113I, G134R, A141P, I157L, A179V, Y198F, G223A, V290I, H307L, G313G, S334P, D343E |
| SSM53E9 | 121 | | | | 3.1 | | G87S, V113I, G134R, A141P, I157L, Y198F, G223A, V290I, H307L, S334P, D343E |

TABLE 15-continued

| Identifier | Activity (U/ml) | T½ (65B) | T½ (70B) | T½ (72B) | T½ (75B) | T½ (80B) | Mut_OverV |
|---|---|---|---|---|---|---|---|
| S242 | 83 | | 7.4 | 3.2 | 1.1 | | V113I, G134R, A141P, I157L, Y198F, G223A, V290I, H307L, G313G, S334P, D343E |
| SSM884F6 | 31 | | 6.9 | 4.1 | | | V113I, G134R, A141P, I157L, Y198F, G223A, V290I, H307L, S334P, D343E, G400G, A405S |
| SSM884E6 | 31 | | 6.0 | 3.7 | | | V113I, G134R, A141P, I157L, Y198F, G223A, V290I, H307L, S334P, D343E, A405E |
| SSM884E4 | 27 | | 6.6 | 4.0 | | | V113I, G134R, A141P, I157L, Y198F, G223A, V290I, H307L, S334P, D343E, A398A, A405F |
| SSM884A11 | 92 | | 8.3 | 4.0 | | | V113I, G134R, A141P, I157L, Y198F, G223A, V290I, H307L, S334P, D343E, A405V |
| S220 | 129 | 17.0 | 5.4 | 3.2 | 1.2 | | A141P, I157L, Y198F, G223A, V290I, H307L, S334P, D343E |
| S241 | 166 | | 9.0 | 5.7 | 1.8 | | V113I, G134R, A141P, I157L, Y198F, G223A, V290I, H307L, S334P, D343E |
| S240 | 115 | | 10.4 | 3.4 | | | V113I, G134R, A141P, I157L, Y198F, G223A, V290I, H307L, S334P, D343E |
| S239 | 71 | | 9.7 | 4.6 | 1.6 | | K71R, V113I, G134R, A141P, I157L, Y198F, G223A, V290I, H307L, S334P, D343E |
| S237 | 72 | | 10.2 | 4.4 | 1.3 | | K108R, V113I, G134R, A141P, I157L, Y198F, G223A, V290I, H307L, S334P, D343E |
| S231 | 55 | | 9.7 | 4.5 | 1.6 | | D34G, V113I, G134R, A141P, I157L, Y198F, G223A, V290I, H307L, S334P, D343E |
| S219 | 99 | 16.7 | 5.2 | 2.6 | 1.1 | | G4D, V113I, A141P, I157L, Y198F, G223A, V290I, H307L, S334P, D343E |
| S227 | 107 | | 9.7 | 5.5 | 2.0 | | A141P, G134R, G223A, H307L, I157L, V113I, V290I, Y198F, G188A |
| S226 | 107 | | | 3.1 | | | A141P, G134R, G223A, H307L, I157L, V113I, V290I, Y198F, S183N? |

Example 9

Model System Baking Tests

The doughs are made in the Farinograph at 30.0° C. 10.00 g reformed flour is weighed out and added in the Farinograph; after 1 min. mixing the reference/sample (reference=buffer or water, sample=enzyme+buffer or water) is added with a sterile pipette through the holes of the kneading vat. After 30 sec. the flour is scraped off the edges—also through the holes of the kneading vat. The sample is kneaded for 7 min.

A test with buffer or water is performed on the Farinograph before the final reference is run. FU should be 400 on the reference, if it is not, this should be adjusted with, for example, the quantity of liquid. The reference/sample is removed with a spatula and placed in the hand (with a disposable glove on it), before it is filled into small glass tubes (of approx. 4.5 cm's length) that are put in NMR tubes and corked up. 7 tubes per dough are made.

When all the samples have been prepared, the tubes are placed in a (programmable) water bath at 33° C. (without corks) for 25 min. and hereafter the water bath is set to stay for 5 min. at 33° C., then to heated to 98° C. over 56 min. (1.1° C. per minute) and finally to stay for 5 min. at 96° C.

Figure 2:
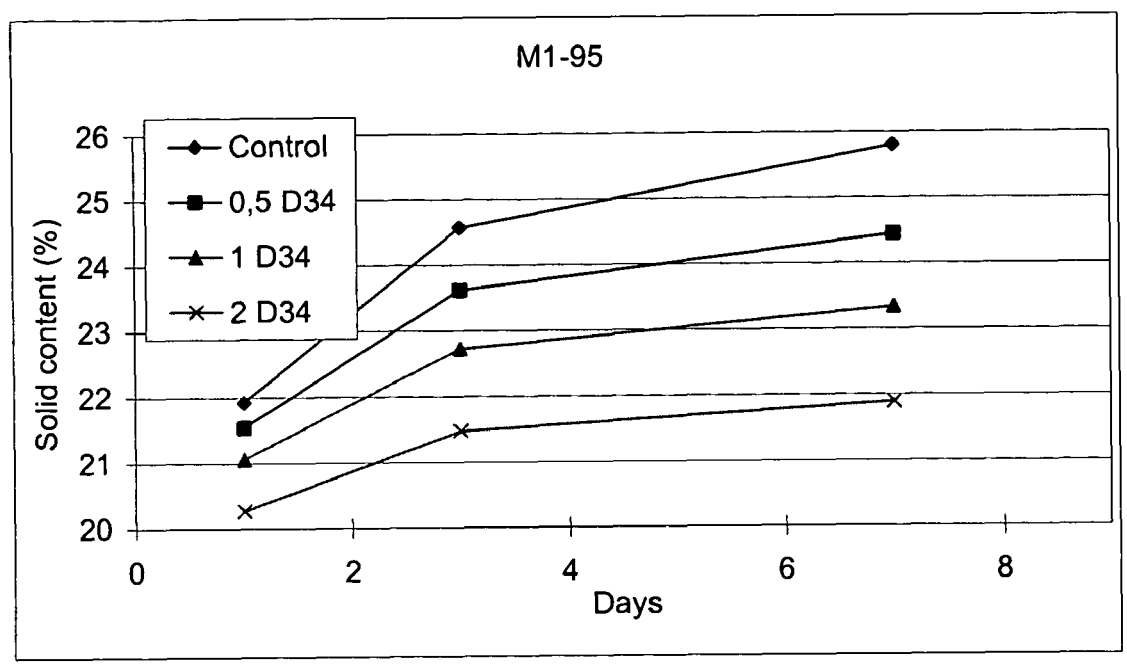
FIG. 2 is a graph showing dosage effect of PSac-D34 in a model dough system trial. Solid content of crumb was measured by NMR. Firmness measured by solid content is plotted against days after baking for control, 0.5, 1, 2 ppm of D34.

The tubes are stored at 20.0° C. in a thermo cupboard. The solid content of the crumb was measured by proton NMR using a Bruker NMS 120 Minispec NMR analyser at day 1, 3 and 7 as shown for crumb samples prepared with 0, 0.05, 1 abnd 2: ppm PSacD34 in FIG. 2. The lower increase in solid content over time represents the reduction in amylopectin retrogradation. After 7 days of storage at 20.0° C. in a thermo cupboard 10-20 mg samples of crumb weighed out and placed in 40 μl aluminium standard DSC capsules and kept at 20° C.

The capsules are used for Differential Scanning Calorimetry on a Mettler Toledo DSC 820 instrument. As parameters are used a heating cycle of 20-95° C. with 10° C. per min. heating and Gas/flow: $N_2$/80 ml per min. The results are analysed and the enthalpy for melting of retrograded amylopectin is calculated in J/g.

Example 10

Antistaling Effects

Model bread crumbs are prepared and measured according to Example 8. As shown in Table 2, PS4 variants show a strong reduction of the amylopectin retrogradation after baking as measured by Differential Scanning Calorimetry in comparison to the control. The PS4 variants shows a clear dosage effect.

Example 11

Firmness Effects in Baking Trials

Baking trials were carried out with a standard white bread sponge and dough recipe for US toast. The sponge dough is prepared from 1600 g of flour "All Purpose Classic" from Sisco Mills, USA", 950 g of water, 40 g of soy bean oil and 32 g of dry yeast. The sponge is mixed for 1 min. at low speed and subsequently 3 min. at speed 2 on a Hobart spiral mixer. The sponge is subsequently fermented for 2.5 hours at 35° C., 85% RH followed by 0.5 hour at 5° C.

Thereafter 400 g of flour, 4 g of dry yeast, 40 g of salt, 2.4 g of calcium propionate, 240 g of high fructose corn syrup (Isosweet), 5 g of the emulsifier PANODAN 205, 5 g of enzyme active soy flour, 30 g of non-active soy flour, 220 g of water and 30 g of a solution of ascorbic acid (prepared from 4 g ascorbic acid solubilised in 500 g of water) are added to the sponge. The resulting dough is mixed for 1 min. at low speed and then 6 min. on speed 2 on a Diosna mixer. Thereafter the dough is rested for 5 min. at ambient temperature, and then 550 g dough pieces are scaled, rested for 5 min. and then sheeted on Glimek sheeter with the settings 1:4, 2:4, 3:15, 4:12 and 10 on each side and transferred to a baking form. After 60 min. proofing at 43° C. at 90% RH the doughs are baked for 29 min. at 218° C.

Figure 3:
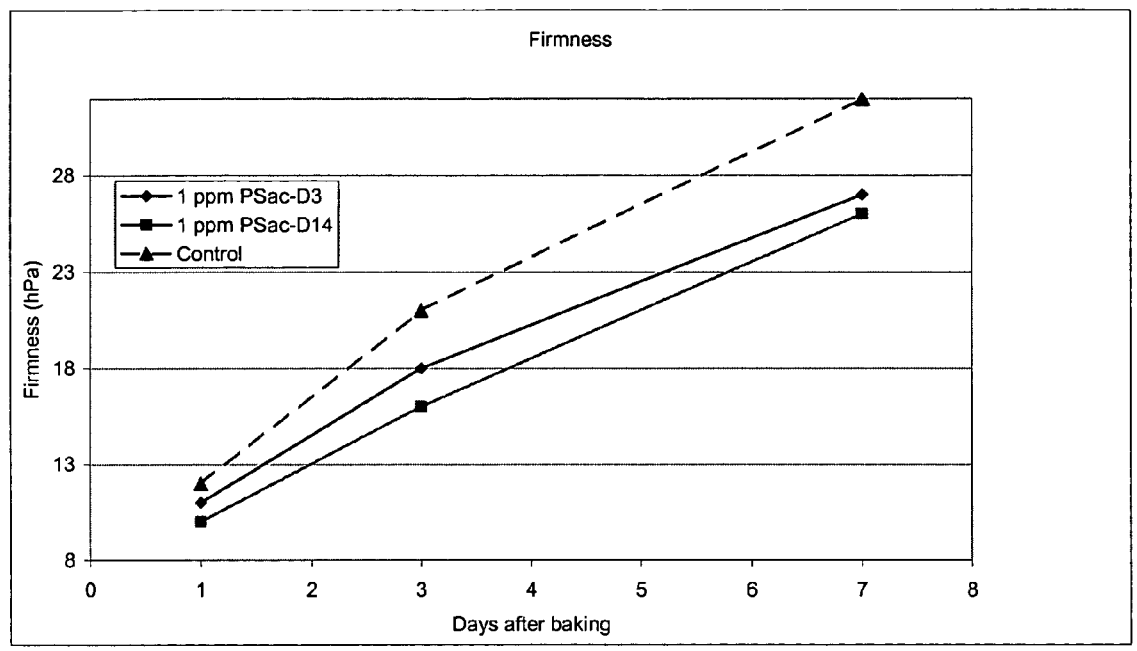
FIG. 3 is a graph shows the results of a baking trial showing reduced firmness and firming rate upon adding PSac-D3 and Psac-D14 in a dosage of 1 mg per kg of flour. Firmness measured by hPa is plotted against days after baking for control.
Figure 4:
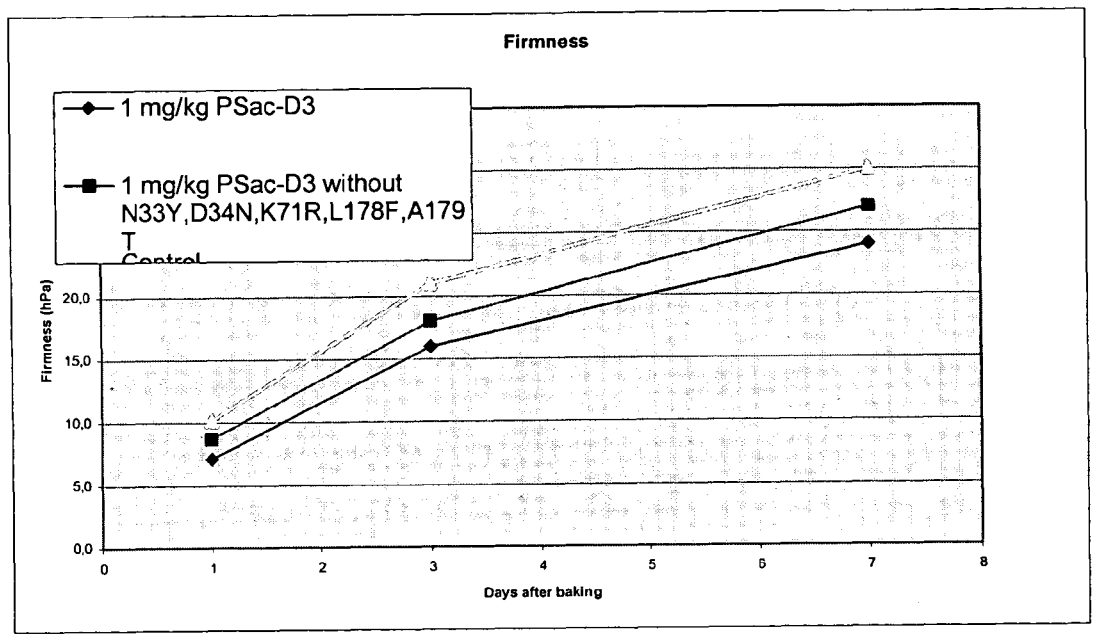
FIG. 4 shows a baking trial showing the increased softening effect of PSac-D3 (G134R, A141P, I157L, G223A, A307L, S334P, K71R, D343E, N33Y, D34N, L178F, A179T) compared to Psac-D3 without N33Y, D34N, K71R, L178F, A179T, which has $t_{1/2}$-75 of 3.6 in contrast to that of PSac-D3 being 9.3 min at 75C.

Firmness and resilience were measured with a TA-XT 2 texture analyser. The Softness, cohesiveness and resilience is determined by analysing bread slices by Texture Profile Analysis using a Texture Analyser From Stable Micro Systems, UK. The following settings were used:

Pre Test Speed: 2 mm/s
Test Speed: 2 mm/s
Post Test Speed: 10 mm/s
Rupture Test Distance: 1%
Distance: 40%
Force: 0.098 N
Time: 5.00 sec
Count: 5
Load Cell: 5 kg
Trigger Type: Auto—0.01 N
Results are shown in FIGS. 3 and 4.

Example 12

Control of Volume of Danish Rolls

Danish Rolls are prepared from a dough based on 2000 g Danish reform flour (from Cerealia), 120 g compressed yeast, 32 g salt, and 32 g sucrose. Water is added to the dough according to prior water optimisation.

The dough is mixed on a Diosna mixer (2 min. at low speed and 5 min. at high speed). The dough temperature after mixing is kept at 26° C. 1350 g dough is scaled and rested for 10 min. in a heating cabinet at 30° C. The rolls are moulded on a Fortuna molder and proofed for 45 min. at 34° C. and at 85% relative humidity. Subsequently the rolls are baked in a Bago 2 oven for 18 min. at 250° C. with steam in the first 13 seconds. After baking the rolls are cooled for 25 min. before weighing and measuring of volume.

The rolls are evaluated regarding crust appearances crumb homogeneity, capping of the crust, ausbund and specific volume (measuring the volume with the rape seed displacement method).

Based on these criteria it is found that the PS4 variants increase the specific volume and improve the quality parameters of Danish rolls. Thus PS4 variants are able to control the volume of baked products.

Each of the applications and patents mentioned in this document, and each document cited or referenced in each of the above applications and patents, including during the prosecution of each of the applications and patents ("application cited documents") and any manufacturer's instructions or catalogues for any products cited or mentioned in each of the applications and patents and in any of the application cited documents, are hereby incorporated herein by reference. Furthermore, all documents cited in this text, and all documents cited or referenced in documents cited in this text, and any manufacturer's instructions or catalogues for any products cited or mentioned in this text, are hereby incorporated herein by reference.

Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the claims.

The invention claimed is:

1. A non-naturally occurring enzyme having at least 95% identity to the polypeptide of SEQ ID NO: 1 and including at least one substitution of the amino acid residue at a position corresponding to a position of SEQ ID NO: 1 selected from the group consisting of 4, 33, 34, 70, 71, 87, 99, 108, 113, 121, 134, 141, 157, 158, 171, 178, 179,188,198, 199, 223, 290, 307, 315, 334, 343, 399 and 405, wherein the enzyme is an exo-specific non-maltogenic exoamylase.

2. The enzyme of claim 1, wherein said at least one substitution is selected from the group consisting of G4D, N33Y, D34N, G70D, K71R, G87S, A99V, K108R, V113I, G121D, G134R, A141P, I157L, G158D, Y171S, L178F, A179T, G188A, Y198F, Y198L, A199V, G223A, V290I, H307L, I315V, S334P, D343E, S399P, A405F and A405E.

3. The enzyme of claim 1, wherein said at least one substitution is at a position corresponding to a position of SEQ ID NO: 1 selected from the group consisting of 33, 34, 71, 87, 121, 134, 141, 157, 178, 179, 223, 307, 334 or 343.

4. The enzyme of claim 3, wherein said at least one substitution is selected from the group consisting of N33Y, D34N, K71R, G87S, G121D, G134R, A141P, I157L, L178F, A179T, G223A, H307L, S334P and D343E.

5. The enzyme of claim 1, further comprising at least one additional substitution at a position corresponding to a position of SEQ ID NO: 1 selected from the group consisting of 108, 158, 171 and 188.

6. The enzyme of claim 5, wherein said at least one additional substitution is selected from K108R, G158D, Y171S, and G188A.

7. The enzyme of claim 1, wherein said enzyme comprises one or more substitutions selected from the group consisting of:

G134R, A141P, I157L, G223A, H307L, S334P, D343E and G121D;
G134R, A141P, I157L, G223A, H307L, S334P, D343E, N33Y and G121D;
G134R, A141P, I157L, G223A, H307L, S334P, D343E and N33Y;
G134R, A141P, I157L, G223A, H307L, S334P, D343E, N33Y, D34N, K71R, L178F, A179T, G87S and G121D;
G134R, A141P, I157L, G223A, H307L, S334P, D343E, N33Y, D34N, K71R, L178F, A179T, G121D, Y171S and G188A;
G134R, A141P, I157L, G223A, H307L, S334P, D343E, N33Y, D34N, K71R, L178F, A179T and G121D;
G87S, G121D, G134R, A141P, I157L, G223A, H307L, S334P, D343E, N33Y, D34N, K71R, L178F and A179T;
G87S, G121D, G134R, A141P, I157L, G223A, H307L, S334P, D343E, N33Y, D34N, K71R, L178F, A179T and G188A;
G134R, A141P, I157L, G223A, H307L, S334P, K71R, L178F and A179T;
G134R, A141P, I157L, G223A, H307L, S334P, L178F and A179T;
G134R, A141P, I157L, G223A, H307L, S334P, N33Y, D34N, L178F and A179T;
G134R, A141P, I157L, G223A, H307L, S334P, L178F, A179T, G87S and G121D;
G134R, A141P, I157L, G223A, H307L, S334P, L178F, A179T and G121D;
G134R, A141P, I157L, G223A, H307L, S334P, D343E, N33Y, D34N, K71R, L178F, A179T, G121D and E343D;
G87S, G121D, G134R, A141P, I157L, G223A, H307L, S334P, D343E, N33Y, D34N, K71R, L178F and A179T;
G87S, G121D, G134R, A141P, I157L, G223A, H307L, S334P, D343E, N33Y, D34N, K71R, L178F, A179T, Y33N, N34D and E343D;
G134R, A141P, I157L, G223A, H307L, S334P, D343E, N33Y, D34N, K71R, L178F, A179T and G121D;
G134R, A141P, I157L, G223A, H307L, S334P, K71R, L178F, A179T and G121D; G87S, V113I, G134R, A141P, I157L, Y198F, G223A, V290I, H307L, S334P and D343E;
I13F, A141P, I157L, Y198F, G223A, V290I, H307L, S334P and D343E;
A99V, V113I, A141P, I157L, Y198F, G223A, V290I, H307L, S334P and D343E; V113I, I157L, Y198F, G223A, V290I, H307L, S334P and D343E; V113I, G134R, A141P, I157L, Y198F, G223A, V290I, H307L, S334P and D343E;
A141P, I157L, Y198F, G223A, V290I, I1307L, S334P and D343E;
A199V, D343E, V113I, A141P, I157L, Y198F, G223A, V290I, H307L and S334P;
V113I, A141P, I157L, Y198F, G223A, V290I, S334P and D343E;
V113I, G121D, G134R, A141P, I157L, Y198F, G223A, V290I, H307L, S334P and D343E;
V113I, G121D, G134R, A141P, I157L, Y198F, G223A, V290I, H307L, S334P and D343E;
V113I, A141P, I157L, Y198F, G223A, V290I, H307L, S334P and D343E;
V113I, A141P, Y198F, G223A, V290I and H307L;
V113I, A141P, Y198F, G223A, V290I, S334P and D343E;
V113I, A141P, Y198F, G223A, A268P, V290I and S399I)
V113I, A141P, Y198F, G223A, V290I and S399P;
V113I, A141P, Y198W, G223A and V290I;
V113I, A141P, Y198F, G223A and V290I;
Y198F, G223A and V290I;
Y198W, G223A and V290I;
V113I, A141P, I157L, Y198F, G223A and V290I;
V113M;
V113A;
V113I, G134R, A141P, I157L, Y198F, G223A, V290I, H307L, S334P and D343E;
V113I, G134R, A141P, I157L, Y198F, G223A, V290I, H307L, I315V, S334P and D343E;
D34N, V113I, G134R, A141P, I157L, Y198F, G223A, V290I, H307L, S334P and D343E;
V113I, G134R, A141P, I157L, G188S, Y198F, G223A, V290I, H307L, S334P and D343E;

K71R, V113I, G134R, A141P, I157L, L178L, Y198F, G223A, V290I, H307L, S334P and D343E;

D34N, V113I, G134R, A141 P, I157L, Y198F, G223A, V290I, H307L, S334P and D343E;

V113I, G134R, A141P, I157L, A179V, Y198F, G223A, V290I, H307L, S334P and D343E;

V113I, G134R, A141P, I157L, I170I, Y198F, G223A, V290I, H307L, S334P and D343E;

V113I, G134R, A141P, I157L, A179V, Y198F, G223A, V290I, H307L, S334P and D343E;

G87S, V113I, G134R, A141P, I157L, Y198F, G223A, V290I, H307L, S334P and D343E;

V113I, G134R, A141P, I157L, Y198F, G223A, V290I, H307L, S334P, D343E and A405E;

V113I, G134R, A141P, I157L, Y198F, G223A, V290I, H307L, S334P, D343E and A405V;

A141P, I157L, Y198F, G223A, V290I, H307L, S334P and D343E;

V113I, G134R, A141P, I157L, Y198L, G223A, V290I, H307L, S334P and D343E;

V113I, G134R, A141P, I157L, Y198F, G223A, V290I, H307L, S334P and D343E;

K71R, V113I, G134R, A141P, I157L, Y198F, G223A, V290I, H307L, S334P and D343E;

K108R, V113I, G134R, A141P, I157L, Y198F, G223A, V290I, H307L, S334P and D343E;

D34G, V113I, G134R, A141P, I157L, Y198F, G223A, V290I, H307L, S334P and D343E;

G4D, V113I, A141P, I157L, Y198F, G223A, V290I, H307L, S334P and D343E; and

A141P, G134R, G223A, H307L, I157L, V113I, V290I, Y198F and G188A.

8. The enzyme of claim 1, wherein said enzyme is derived from a *Pseudomonas sp.*

9. The enzyme of claim 8, wherein said *Pseudomonas sp.* is *Pseudomonas saccharophila* or *Pseudomonas stutzeri*.

10. The enzyme of claim 3, wherein said at least one substitution is at the position corresponding to position 178 of SEQ ID NO: 1.

11. The enzyme of claim 1, wherein the substitutions include substitutions at positions corresponding to positions 33, 34, 121, 134, 141, 157, 178, 179, 223, 307 and 334 of SEQ ID NO: 1.

12. A method for preparing a food product comprising: (a) providing a starch medium; (b) adding to the starch medium the exoamylase according to any one of claims 1 and 2 to 11.

13. A process for making a bread product comprising: (a) providing a dough medium; (b) adding to the dough medium the exoamylase of any one of claims 1 and 2 to 11;

and (c) applying heat to the starch medium during or after step (b) to produce a bread product.

* * * * *